(12) United States Patent
Parent et al.

(10) Patent No.: US 8,735,419 B2
(45) Date of Patent: *May 27, 2014

(54) FORMS OF RIFAXIMIN AND USES THEREOF

(75) Inventors: Stephan D. Parent, West Lafayette, IN (US); Lisa L. McQueen, West Lafayette, IN (US); Patricia Andres, West Lafayette, IN (US); Paul Schields, West Lafayette, IN (US); Yiduo Wu, North Brunswick, NJ (US); Fei Ding, Overland Park, KS (US); Jared P. Smit, Lafayette, IN (US)

(73) Assignee: Salix Pharmaceuticals, Ltd., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/371,238

(22) Filed: Feb. 10, 2012

(65) Prior Publication Data

US 2012/0207833 A1    Aug. 16, 2012

Related U.S. Application Data

(60) Provisional application No. 61/441,902, filed on Feb. 11, 2011, provisional application No. 61/530,905, filed on Oct. 18, 2011, provisional application No. 61/556,649, filed on Nov. 7, 2011, provisional application No. 61/583,024, filed on Jan. 4, 2012.

(51) Int. Cl.
*C07D 498/12* (2006.01)
*A61K 31/395* (2006.01)

(52) U.S. Cl.
USPC .......................................... 514/279; 540/456

(58) Field of Classification Search
USPC .......................................... 514/279; 540/456
See application file for complete search history.

(56) References Cited

U.S. PATENT DOCUMENTS

| 4,341,785 | A | 7/1982 | Marchi et al. |
|---|---|---|---|
| 4,557,866 | A | 12/1985 | Cannata et al. |
| 7,045,620 | B2 | 5/2006 | Viscomi et al. |
| 7,612,199 | B2 | 11/2009 | Viscomi et al. |
| 7,709,634 | B2 | 5/2010 | Kothakonda et al. |
| 7,915,275 | B2 | 3/2011 | Viscomi et al. |
| 8,067,429 | B2 | 11/2011 | Gushurst et al. |
| 2005/0272754 | A1 | 12/2005 | Viscomi et al. |
| 2006/0210592 | A1 | 9/2006 | Kodsi |
| 2008/0262232 | A1 | 10/2008 | Viscomi et al. |
| 2009/0028940 | A1 | 1/2009 | Jahagirdar et al. |
| 2009/0130201 | A1 | 5/2009 | Viscomi et al. |
| 2009/0312357 | A1 | 12/2009 | Rao et al. |
| 2010/0174064 | A1 | 7/2010 | Gushurst et al. |

FOREIGN PATENT DOCUMENTS

| EP | 0161534 A2 | 11/1985 |
|---|---|---|
| IT | MI-2005A000345 | 3/2005 |
| WO | WO-2006094662 A1 | 9/2006 |
| WO | WO-2008035109 A1 | 3/2008 |
| WO | WO-2008155728 A1 | 12/2008 |
| WO | WO-2009008005 A1 | 1/2009 |
| WO | WO-2009047801 A1 | 4/2009 |
| WO | WO-2009108730 A2 | 9/2009 |
| WO | WO-2010033179 A1 | 3/2010 |
| WO | WO-2010067072 A1 | 6/2010 |
| WO | WO-2011051971 A2 | 5/2011 |

OTHER PUBLICATIONS

Rossi, C. et al., "NMR Investigation of a New Semisynthetic Bioactive Compound," Bulletin of Magnetic Resonance, 1996, vol. 18, No. 1-2, pp. 87-90.
Viscomi, G. et al., "Crystal Forms of Rifaximin and Their Effect on Pharmaceutical Properties," CrystEngComm, 2008, 10, 1074-1081.
Brufani, M. et al., "X-Ray Crystal Structure of 4-Deoxy-3'-bromopyrido[1,2'-1,2]imidazo[5,4-c]rifamycin S," The Journal of Antibiotics, 37:12, 1623-1627 (Dec. 1984).

*Primary Examiner* — Bruck Kifle
(74) *Attorney, Agent, or Firm* — McCarter & English, LLP; Jonathan M. Sparks

(57) ABSTRACT

Embodiments relate to Rifaximin polymorphic, salt, and hydrate forms, methods of producing polymorphic forms and to their use in medicinal preparations and to therapeutic methods using them.

12 Claims, 55 Drawing Sheets

Figure 1. Representative XRPD patterns of rifaximin Form μ.

Figure 2. List of observed peaks for rifaximin Form μ.

Figure 3. List of observed peaks for rifaximin Form μ.

Figure 4. Tentative indexing solution for rifaximin Form μ.    bars indicate allowed reflections based on the unit cell dimensions and the assigned space group.

Figure 5. Tentative indexing solution for rifaximin Form μ.    bars indicate allowed reflections based on the unit cell dimensions and the assigned space group (P2₁, #4).

Figure 6. DSC and TGA thermograms of rifaximin Form µ.

Figure 7. Moisture sorption of rifaximin Form µ.

Figure 8. Post-Moisture sorption XRPD of rifaximin Form µ.
Top: before moisture sorption;
Bottom: after moisture sorption (Form γ).

Figure 11 Summary of Results of Drying Experiments.

Figure 12: XRPD patterns of samples of Rifaximin Unknown Pi.

Figure 13. List of observed peaks for Rifaximin Pi,

Figure 14. List of observed peaks for Rifaximin Pi,

Figure 15. Comparison of XRPD patterns of Rifaximin

Figure 16. Thermal analysis of Rifaximin Pi

Figure 17. Dynamic vapor sorption isotherm of a sample of Rifaximin Pi

Figure 18. Proton NMR spectrum of Rifaximin Pi

Figure 19. ATR-IR spectrum of Rifaximin Pi

Figure 20. Raman spectrum of Rifaximin Pi

Figure 21. Solid state carbon NMR spectrum of Rifaximin Pi

Figure 22  XRPD Pattern of Rifaximin Form Xi (ξ).

Figure 23 List of Observed Peaks for Rifaximin Form Xi (ξ)

Figure 24  DSC Thermogram of Rifaximin Form Xi (ξ).

Figure 25  TGA Thermogram of Rifaximin Form Xi (ξ).

Figure 26    Moisture Sorption Isotherm of Rifaximin Form Xi (ξ).

Figure 27 XRPD pattern of Rifaximin Form Xi (ξ) Before and After the Moisture Sorption Experiment Figure 29   Solid State NMR Spectrum of Rifaximin Form Xi(ξ).

Figure 30  Infrared (IR) Spectrum of Rifaximin Form Xi(ξ).

Figure 31 Raman Spectrum of Rifaximin Form Xi(ξ).

Figure 33. Indexed unit cell parameters of Rifaximin

|  | Rifaximin |
|---|---|
| Bravais Type | Primitive Orthorhombic |
| a [Å] | 12.636 |
| b [Å] | 18.461 |
| c [Å] | 26.003 |
| α [deg] | 90 |
| β [deg] | 90 |
| γ [deg] | 90 |
| Volume [Å³/cell] | 6,065.7 |
| Chiral Contents? | Chiral |
| Extinction Symbol | P - 21 21 |
| Space Group(s) | $P22_12_1$ (18)* |
| Source | Triads Algorithm |

* = Unconventional space group setting.

Figure 34. List of observed peaks for Rifaximin, Form Omicron
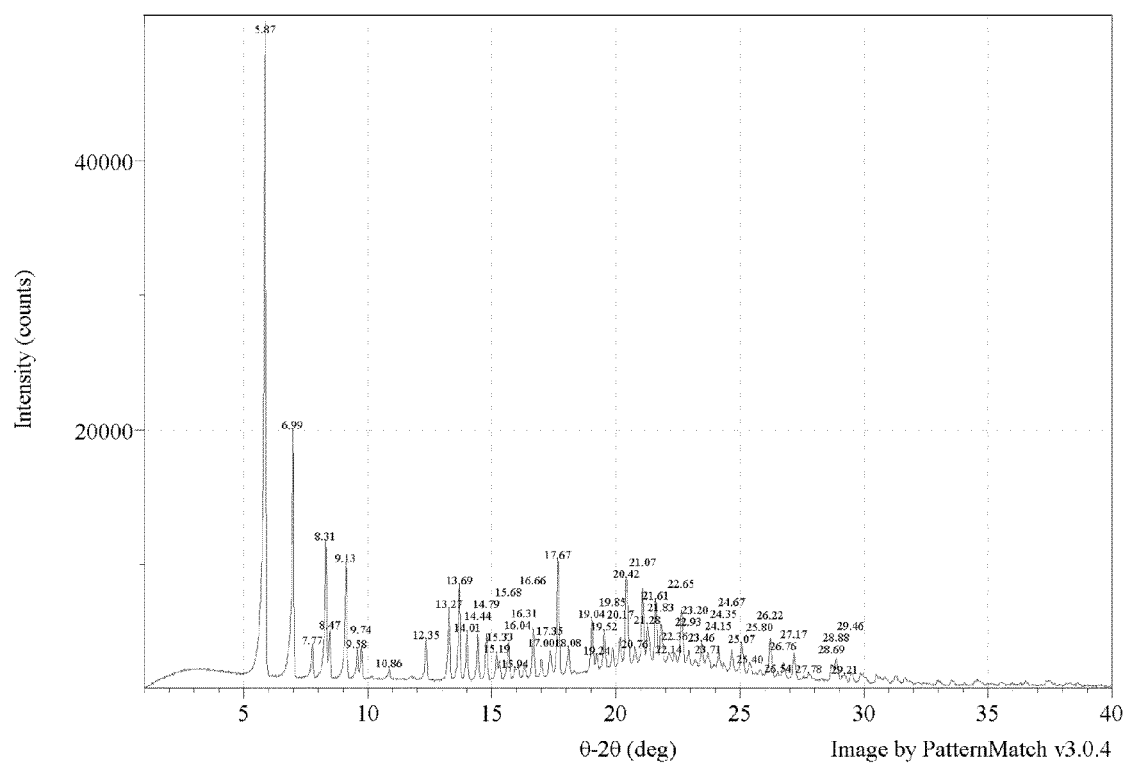

Figure 35. Thermal analysis of Rifaximin Form Omicron,
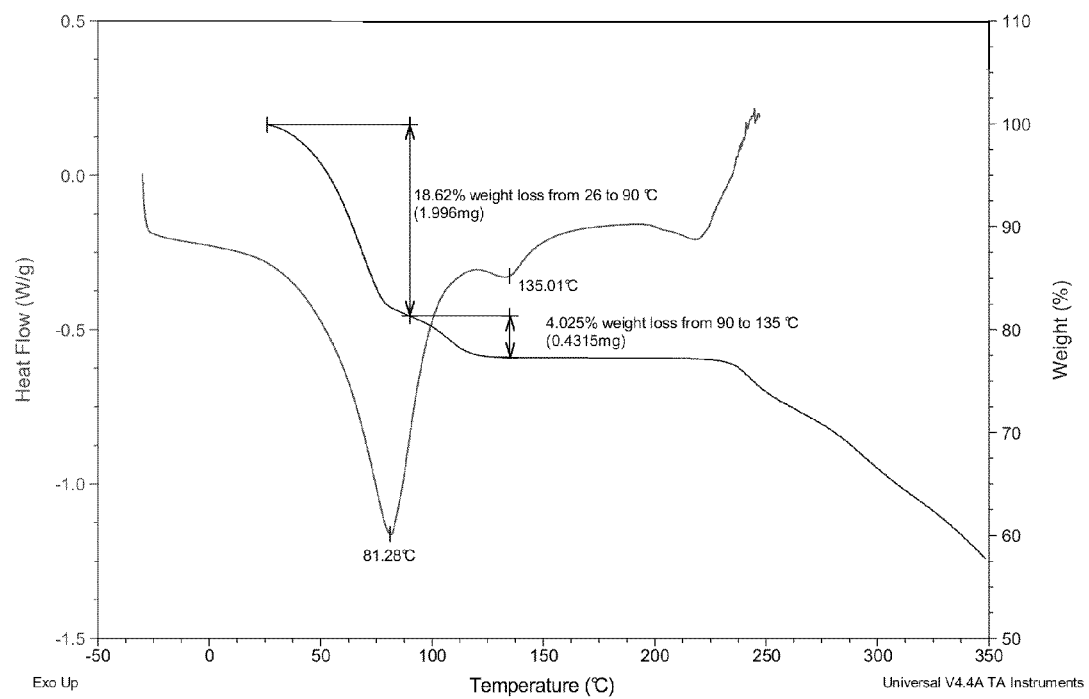

Figure 36. Dynamic vapor sorption isotherm of a sample of Rifaximin Form Omicron
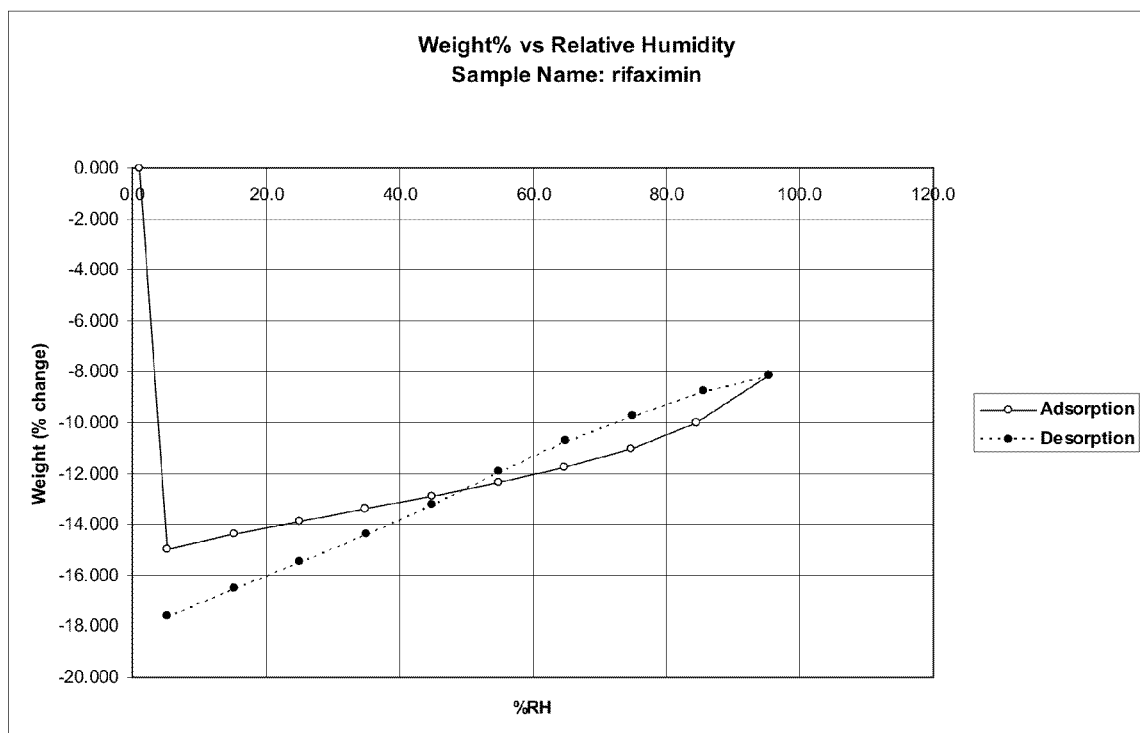

Figure 37. Comparison of XRPD patterns of Rifaximin Form Omicron and the post-DVS sample, Form Iota.
Top: Form Iota
Bottom: Form Omicron
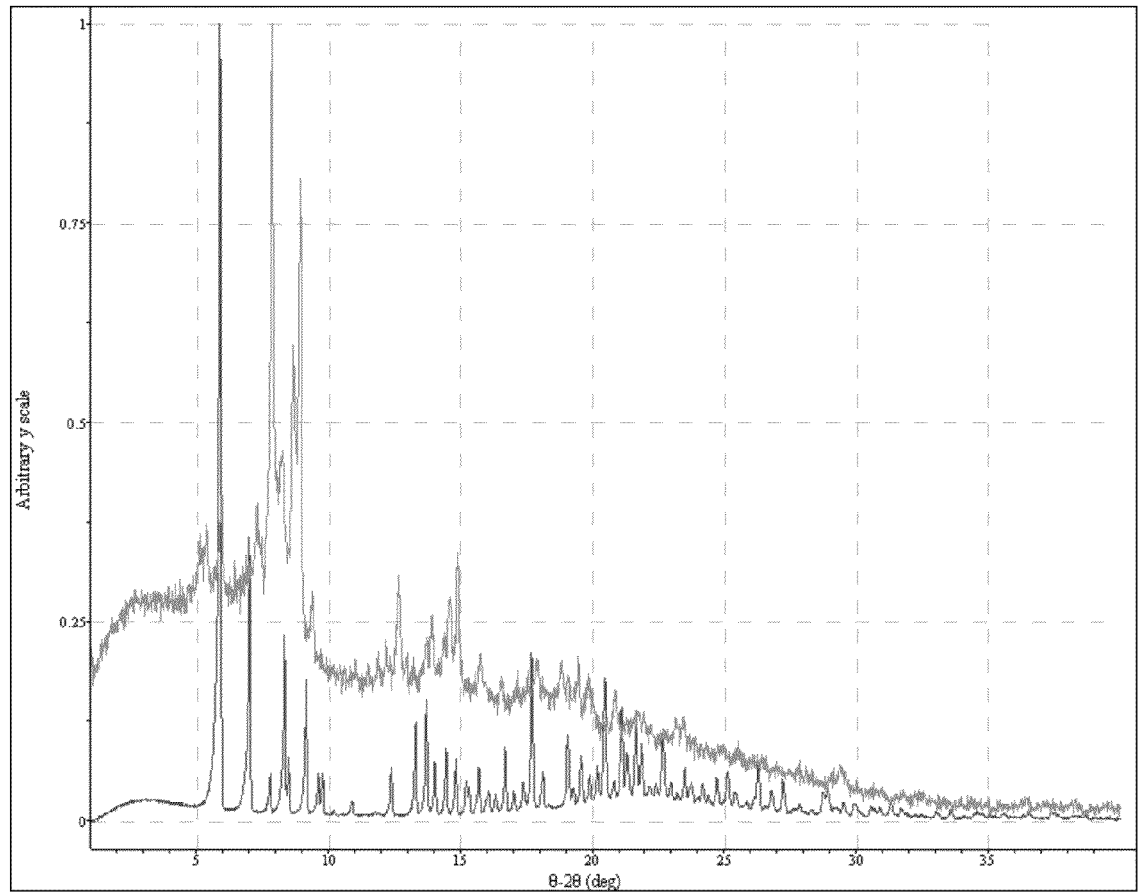

Figure 38. ATR-IR spectrum of Rifaximin Form Omicron,
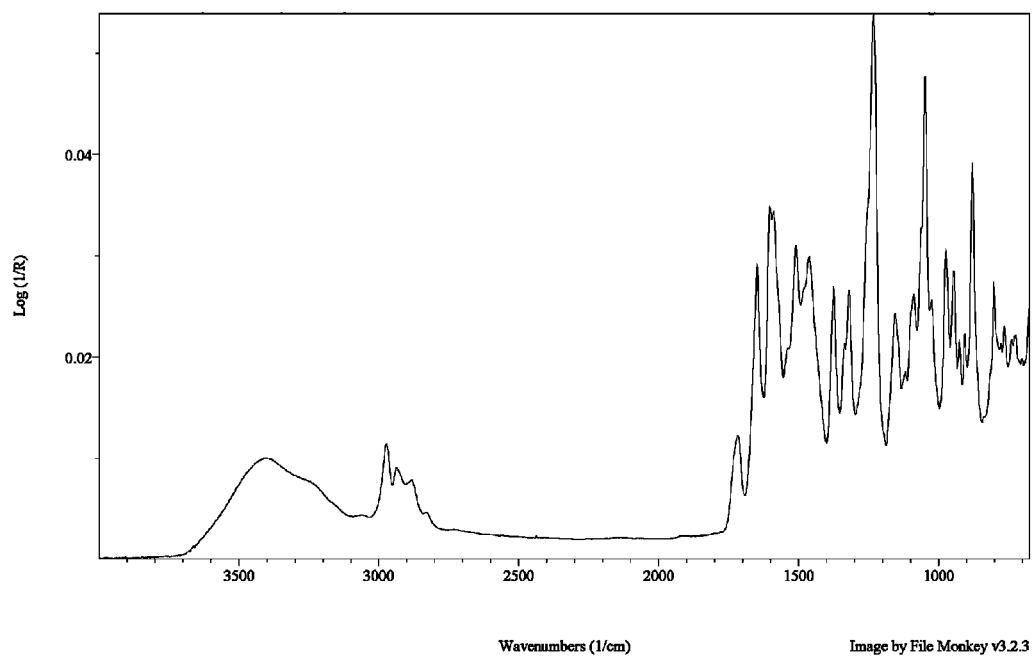

Figure 39. Raman spectrum of Rifaximin Form Omicron,
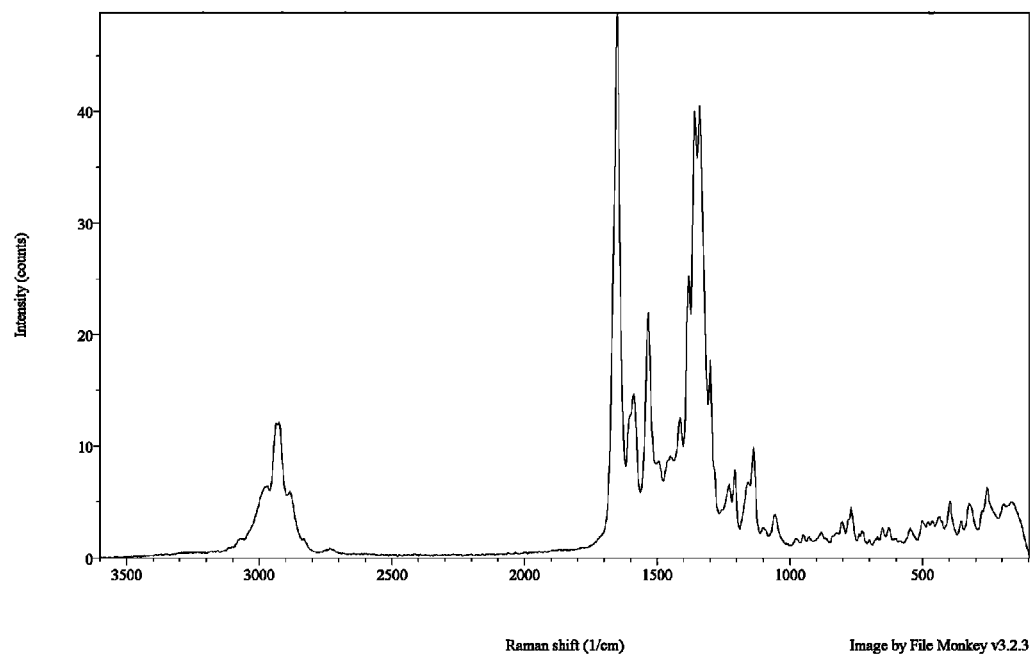

Figure 40. Solution ¹H NMR spectrum of Rifaximin Form Omicron
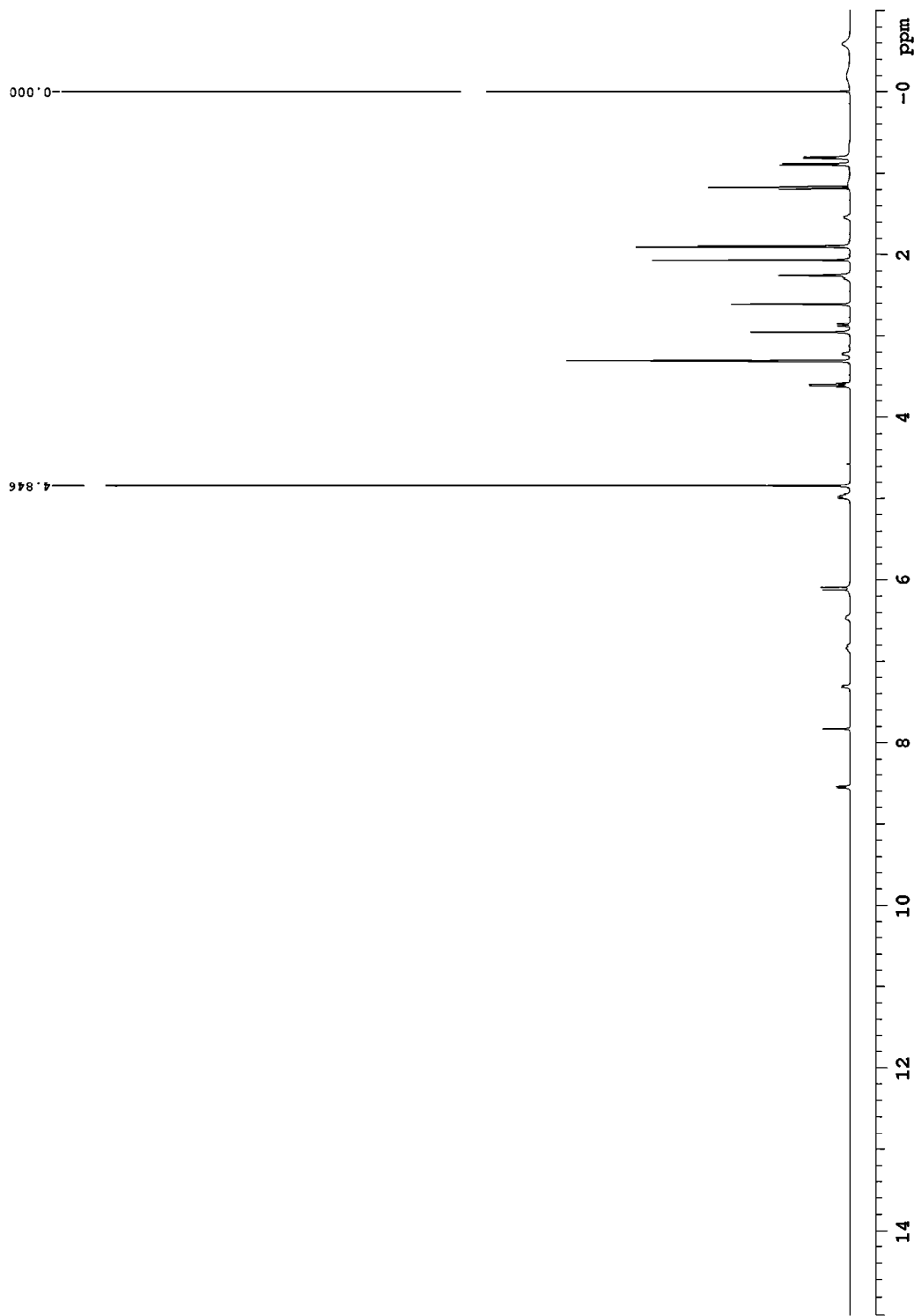

Figure 41. Solid state 13C NMR spectrum of Rifaximin Form Omicron
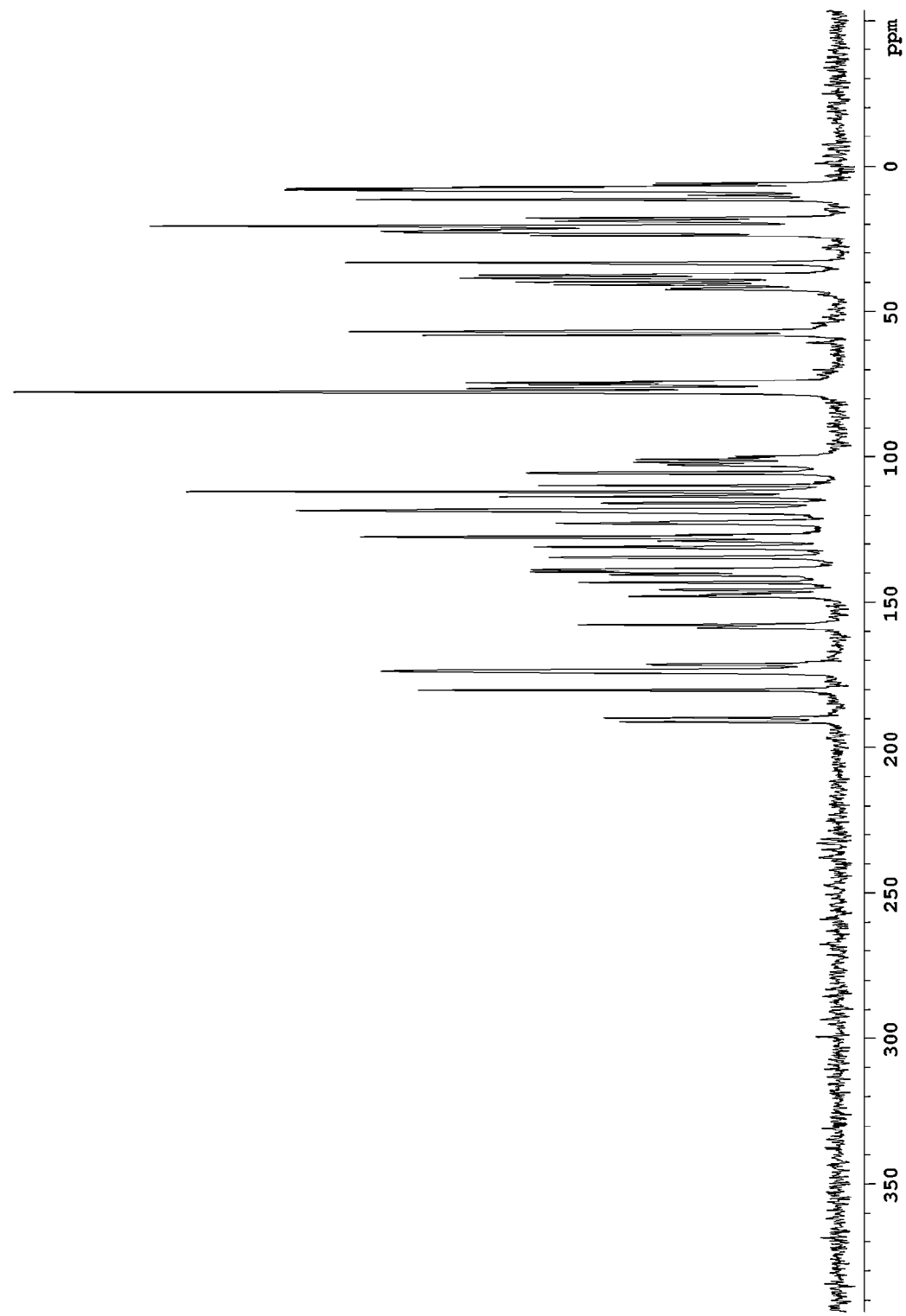

XRPD Pattern of Rifaximin Form η

Figure 49A

Observed peaks for Rifaximin, Form Iota

| °2θ | d space (Å) | Intensity (%) |
|---|---|---|
| 5.3 ± 0.1 | 16.550 ± 0.316 | 17 |
| 5.9 ± 0.1 | 15.031 ± 0.260 | 54 |
| 6.5 ± 0.1 | 13.683 ± 0.215 | 9 |
| 7.4 ± 0.1 | 12.011 ± 0.165 | 20 |
| 7.9 ± 0.1 | 11.220 ± 0.144 | 100 |
| 8.2 ± 0.1 | 10.757 ± 0.132 | 16 |
| 9.0 ± 0.1 | 9.870 ± 0.111 | 44 |
| 9.4 ± 0.1 | 9.449 ± 0.102 | 24 |
| 11.1 ± 0.1 | 7.957 ± 0.072 | 2 |
| 11.5 ± 0.1 | 7.695 ± 0.067 | 5 |
| 11.9 ± 0.1 | 7.450 ± 0.063 | 5 |
| 12.2 ± 0.1 | 7.231 ± 0.059 | 9 |
| 12.7 ± 0.1 | 6.992 ± 0.055 | 37 |
| 13.9 ± 0.1 | 6.371 ± 0.046 | 34 |
| 14.9 ± 0.1 | 5.930 ± 0.040 | 27 |
| 15.8 ± 0.1 | 5.602 ± 0.035 | 12 |
| 16.2 ± 0.1 | 5.478 ± 0.034 | 7 |
| 16.5 ± 0.1 | 5.360 ± 0.032 | 14 |
| 17.2 ± 0.1 | 5.162 ± 0.030 | 7 |
| 18.0 ± 0.1 | 4.928 ± 0.027 | 5 |
| 18.9 ± 0.1 | 4.700 ± 0.025 | 8 |
| 19.3 ± 0.1 | 4.604 ± 0.024 | 10 |
| 20.0 ± 0.1 | 4.448 ± 0.022 | 17 |
| 20.9 ± 0.1 | 4.250 ± 0.020 | 17 |
| 21.7 ± 0.1 | 4.099 ± 0.019 | 15 |
| 23.4 ± 0.1 | 3.795 ± 0.016 | 16 |
| 23.8 ± 0.1 | 3.733 ± 0.015 | 6 |
| 24.3 ± 0.1 | 3.663 ± 0.015 | 5 |
| 25.0 ± 0.1 | 3.559 ± 0.014 | 3 |
| 25.5 ± 0.1 | 3.488 ± 0.013 | 8 |
| 26.2 ± 0.1 | 3.401 ± 0.013 | 5 |
| 26.9 ± 0.1 | 3.310 ± 0.012 | 4 |
| 28.1 ± 0.1 | 3.176 ± 0.011 | 7 |
| 29.7 ± 0.1 | 3.010 ± 0.010 | 6 |

Figure 49B

Prominent peaks for Rifaximin, Form Iota

| °2θ | d space (Å) | Intensity (%) |
|---|---|---|
| 5.9 ± 0.1 | 15.031 ± 0.260 | 54 |
| 7.9 ± 0.1 | 11.220 ± 0.144 | 100 |
| 9.0 ± 0.1 | 9.870 ± 0.111 | 44 |
| 12.7 ± 0.1 | 6.992 ± 0.055 | 37 |
| 13.9 ± 0.1 | 6.371 ± 0.046 | 34 |
| 14.9 ± 0.1 | 5.930 ± 0.040 | 27 |

Figure 51A
Hot Stage microscopy of Rifaximin, Form i.
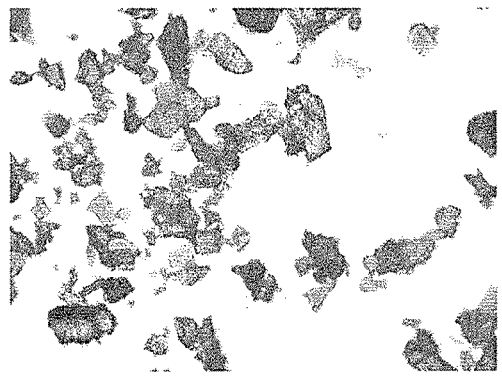
T= 30°C
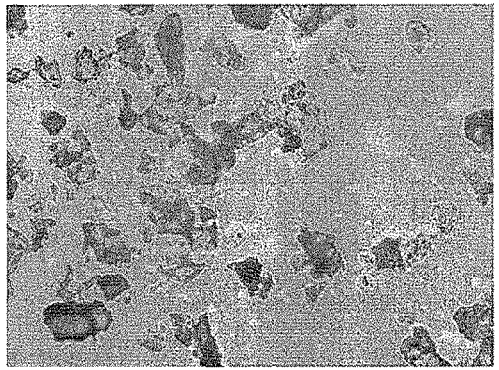
T= 30°C
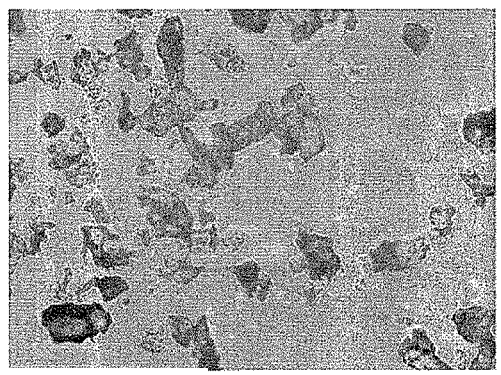
T= 80°C
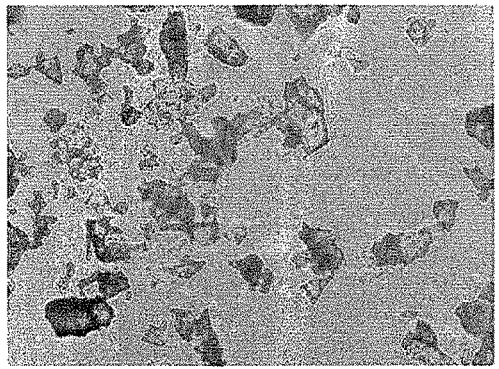
T= 120°C
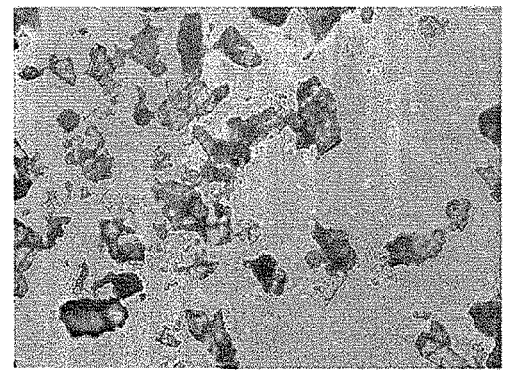
T= 190°C
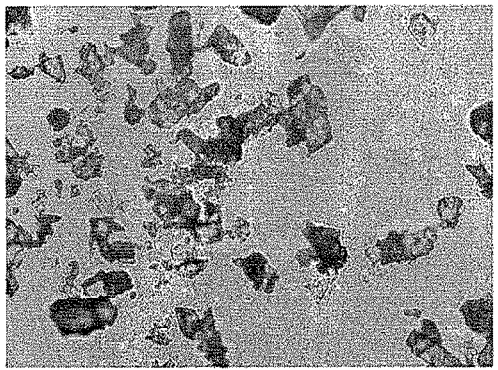
T= 204°C Figure 51B
Hot Stage microscopy of Rifaximin, Form i.
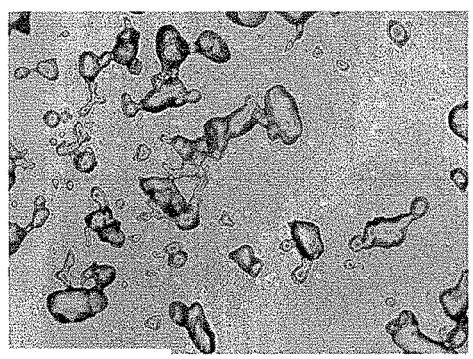
T= 218°C
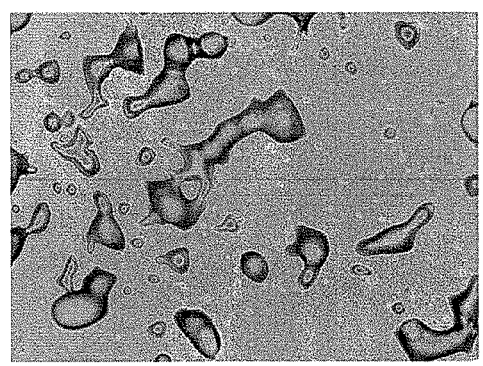
T= 222°C
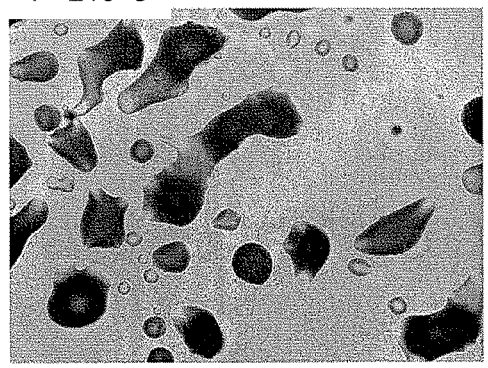
T= 250°C

FORMS OF RIFAXIMIN AND USES THEREOF

RELATED APPLICATIONS

This application claims the benefit of U.S. provisional application Nos. 61/441,902, filed Feb. 11, 2011; 61/530,905, filed Sep. 2, 2011; 61/556,649, filed Nov. 7, 2011; and 61/583,024, filed Jan. 4, 2012, each of which are incorporated by reference herein in their entirety.

BACKGROUND

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res*, 14 (2), 51-56, (1994)).

Rifaximin is described in Italian Patent IT 1154655 and EP 0161534, both of which are incorporated herein by reference in their entirety for all purposes. EP 0161534 discloses a process for rifaximin production using rifamycin O as the starting material (The Merck Index, XIII Ed., 8301). U.S. Pat. No. 7,045,620 B1 and PCT Publication WO 2006/094662 A1 disclose polymorphic forms of rifaximin, both of which are incorporated herein by reference. U.S. Patent Publication US 2010-0239664 and US 2010-0174064 and PCT Publication WO 2009/108730 also A1 disclose polymorphic forms of Rifaximin, both of which are incorporated herein by reference The forms of rifaximin disclosed herein can be advantageously used as pure and homogeneous products in the manufacture of medicinal preparations containing rifaximin.

SUMMARY

Embodiments described herein relate to the discovery of new polymorphic forms of rifaximin and the use of those forms as antibiotics. In some embodiments, polymorphic Forms of rifaximin of the antibiotic known as rifaximin (INN), in the manufacture of medicinal preparations for the oral or topical route is contemplated. Embodiments described herein also relate to administration of such medicinal preparations to a subject in need of treatment with antibiotics.

According to one aspect, provided herein are polymorphic forms of rifaximin, including Form Mu, Form Pi, Form Omicron, Form Zeta, Form Eta, Form Iota, and salt forms and hydrates of rifaximin.

According to one aspect, the polymorphic forms of rifaximin described herein are selected from one or more of Form Mu, Form Pi, Form Omicron, Form Zeta, Form Eta, Form Iota, salt forms, or hydrate forms, or combinations thereof.

According to one aspect, the polymorphic form of rifaximin is Form Mu. In another aspect, the polymorphic form of rifaximin is Form Pi. In another aspect, the polymorphic form of rifaximin is Form Omicron. In another aspect, the polymorphic form of rifaximin is Form Zeta. In another aspect, the polymorphic form of rifaximin is Form Eta. In another aspect, the polymorphic form of rifaximin is Form Iota. In another aspect, the rifaximin is a salt form. In another aspect, rifaximin is a hydrate form.

According to one aspect, provided herein are pharmaceutical compositions comprising at least one Form of rifaximin as described herein, with one or more pharmaceutically acceptable carriers.

According to one aspect, provided herein are processes for producing the Forms of rifaximin as described herein.

According to one aspect, provided herein are methods of treating, preventing, or alleviating diseases and disorders described herein, e.g., a bowel related disorder by administering at least one Form of rifaximin as described herein.

According to one aspect, provided herein are packaged compositions comprising at least one Form of rifaximin as described herein.

BRIEF DESCRIPTION OF THE DRAWINGS

FIG. 33 shows the index unit cell parameters of rifaximin Form Omicron.

FIG. 34 shows an XRPD pattern of the observed peaks for rifaximin Form Omicron.

FIG. 35 shows DSC and TGA thermograms of rifaximin Form Omicron.

FIG. 36 shows moisture sorption (DVS) data of rifaximin Form Omicron.

FIG. 37 shows a XRPD pattern of rifaximin Form Omicron and post-DVS sample, Form Iota (ι).

FIG. 38 shows an ATR-IR spectrum of rifaximin Form Omicron.

FIG. 39 shows a Raman spectrum of rifaximin Form Omicron.

FIG. 40 shows solution proton NMR spectrum of rifaximin Form Omicron.

FIG. 41 shows a solid state carbon NMR spectrum of rifaximin Form Omicron.

FIG. 49A depicts peaks for rifaximin, Form Iota and 49B depicts prominent peaks for rifaximin, Form Iota.

FIGS. 51A and 51B depict exemplary results of hot stage microscopy of rifaximin, Form Iota.

DETAILED DESCRIPTION

Figure 1:
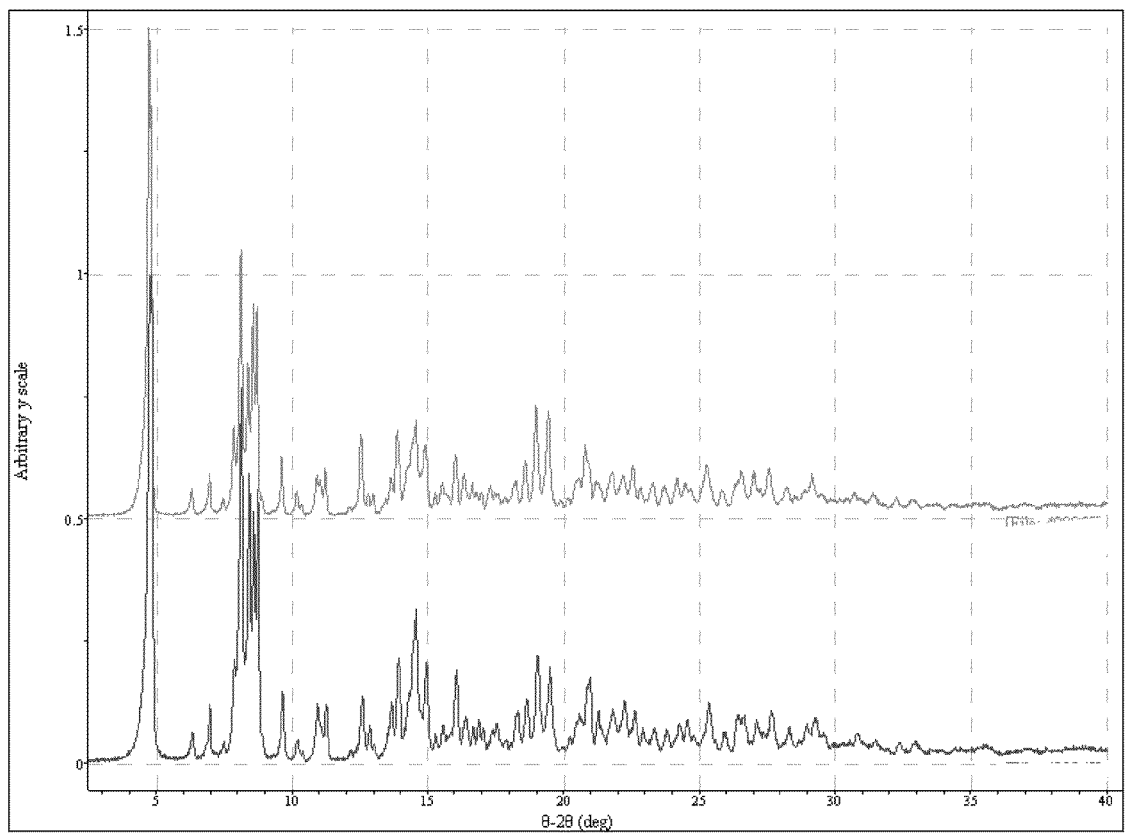
FIG. 1 shows a XRPD pattern of rifaximin Form Mu.

Rifaximin is a compound of the rifamycin class of antibiotics. Rifaximin is a compound having the structure of Formula I:

(Formula I)

Rifaximin is observed to crystallize in multiple crystalline forms, many of which are variable multi-component crystals. The majority of the forms have been identified as variable and non-stoichiometric systems, where the unit cell volume can change to accommodate varying amounts of solvent and/or water.

Rifaximin is approved for the treatment of pathologies caused by non-invasive strains of *Escherichia coli*, a microorganism which is not able to penetrate into GI mucosa and therefore remains in contact with gastrointestinal fluids. In respect to possible adverse events coupled to the therapeutic use of rifaximin, the induction of bacterial resistance to the antibiotics is of particular relevance.

From this point of view, any differences found in the systemic absorption of the forms of rifaximin disclosed herein can be significant, because at sub-inhibitory concentration of rifaximin, such as in the range from about 0.1 to about 1 mg/ml, selection of resistant mutants has been demonstrated to be possible (Marchese A. et al. "In vitro activity of rifaximin, metronidazole and vancomycin against *clostridium difficile* and the rate of selection of spontaneously resistant mutants against representative anaerobic and aerobic bacteria, including ammonia-producing species." *Chemotherapy*, 46(4), 253-266 (2000)).

Polymorphs of rifaximin have been found to have differing in vivo bioavailability properties. Thus, the polymorphs disclosed herein can be useful in the preparation of pharmaceuticals with different characteristics for the treatment of infections. This allows generation of rifaximin preparations that have significantly different levels of adsorption with $C_{max}$ values from about 0.0 ng/ml to about 5.0 μg/ml. This leads to preparation of rifaximin compositions that are from negligibly to significantly adsorbed by subjects undergoing treatment.

Thus, in one aspect, a method of modulating the therapeutic action of rifaximin is provided, comprising selecting the proper polymorphic form, or mixture of forms, for treatment of a patient. For example, in the case of invasive bacteria, the most bioavailable polymorphic form can be selected from those disclosed herein, whereas in the case of non-invasive pathogens, less adsorbed forms of rifaximin can be selected since they can be safer for the subject undergoing treatment. Forms of rifaximin can determine solubility, which can also determine bioavailability.

As used herein, "rifaximin Form x," "Form x" "Form x of rifaximin," "polymorph x," "Form x (y)," "Form y" and "rifaximin x" and variations thereof, where x is Mu, Pi, Omicron, Zeta, Eta, Xi, or Iota, and y represents the corresponding Greek characters (μ), (π), (ο), (ζ), (η), (ξ), and (ι), are used interchangeably to denote the polymorphic forms of rifaximin as further described herein by, for example, one or more peaks of an x-ray diffractogram or differential scanning calorimetry data. Forms of rifaxmin as described herein comprise x-ray powder diffraction pattern peak positions as denoted in the Tables, Examples and Figures disclosed herein.

As used herein, the term polymorph is occasionally used as a general term in reference to the forms of rifaximin and includes within the context, salt, hydrate, and polymorph co-crystal forms of rifaximin. This use depends on context and will be clear to one of skill in the art.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, and/or the instrumentation used. In this case the measurement variability of the instrument was about ±0.2 degrees 2-θ, which is consistent with the USP definition for peak position error. A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word "about."

As used herein, "similar" in reference to a form exhibiting characteristics similar to, for example, an XRPD, an IR, a Raman spectrum, a DSC, TGA, NMR, SSNMR, etc, indicates that the polymorph is identifiable by that method and could range from similar to substantially similar, so long as the material is identified by the method with variations expected by one of skill in the art according to the experimental variations, including, for example, instruments used, time of day, humidity, season, pressure, room temperature, etc.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph can have distinct physical properties. Therefore, a single compound can give rise to a variety of polymorphic forms where each form has different and distinct physical properties, such as solubility profiles, melting point temperatures, hygroscopicity, particle shape, density, flowability, compactibility and/or x-ray diffraction peaks. The solubility of each polymorph can vary, thus, identifying the existence of pharmaceutical polymorphs is desirable for providing pharmaceuticals with consistent and reproducible solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffractometry and by other methods such as infrared spectroscopy. For a general review of polymorphs and the pharmaceutical applications of polymorphs see G. M. Wall, *Pharm Manuf.* 3, 33 (1986); J. K. Haleblian and W. McCrone, *J. Pharm. Sci.,* 58, 911 (1969); and J. K. Haleblian, *J. Pharm. Sci.,* 64, 1269 (1975), each of which is incorporated herein by reference in its entirety.

As used herein, "subject" includes organisms which are capable of suffering from a bowel disorder or other disorder treatable by rifaximin or who could otherwise benefit from the administration of a rifaximin as described herein, such as human and non-human animals. Preferred human animals include human subjects. The term "non-human animals" includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder infection, e.g., subjects suffering from one or more of an immune suppression, subjects that have been exposed to other subjects with a bacterial infection, physicians, nurses, subjects traveling to remote areas known to harbor bacteria that causes travelers' diarrhea, subjects who drink amounts of alcohol that damage the liver, subjects with a history of hepatic dysfunction, etc.

The language "a prophylactically effective amount" of a compound refers to an amount of a Form of rifaximin described herein, or otherwise as described herein which is effective, upon single or multiple dose administration to the subject, in preventing or treating a bacterial infection.

The language "therapeutically effective amount" of a compound refers to an amount of an agent which is effective, upon single or multiple dose administration to the subject to provide a therapeutic benefit to the subject. In some embodiments, the therapeutic benefit is inhibiting a virus, or in prolonging the survivability of a subject with such a viral infection. In some embodiments, the therapeutic benefit is inhibiting a bacterial infection or prolonging the survival of a subject with such a bacterial infection beyond that expected in the absence of such treatment.

For XRPD analysis, accuracy and precision associated with measurements on independently prepared samples on different instruments can lead to variability which is greater than ±0.2° 2θ.

The rifaximin Forms described herein may also be characterized by unit cell volume. One of skill in the art would be able to determine major peaks and uniquely identifying peaks of the polymorphs of rifaximin using the information set forth herein as well as the peak lists and XPRD patterns and data.

Figure 2:
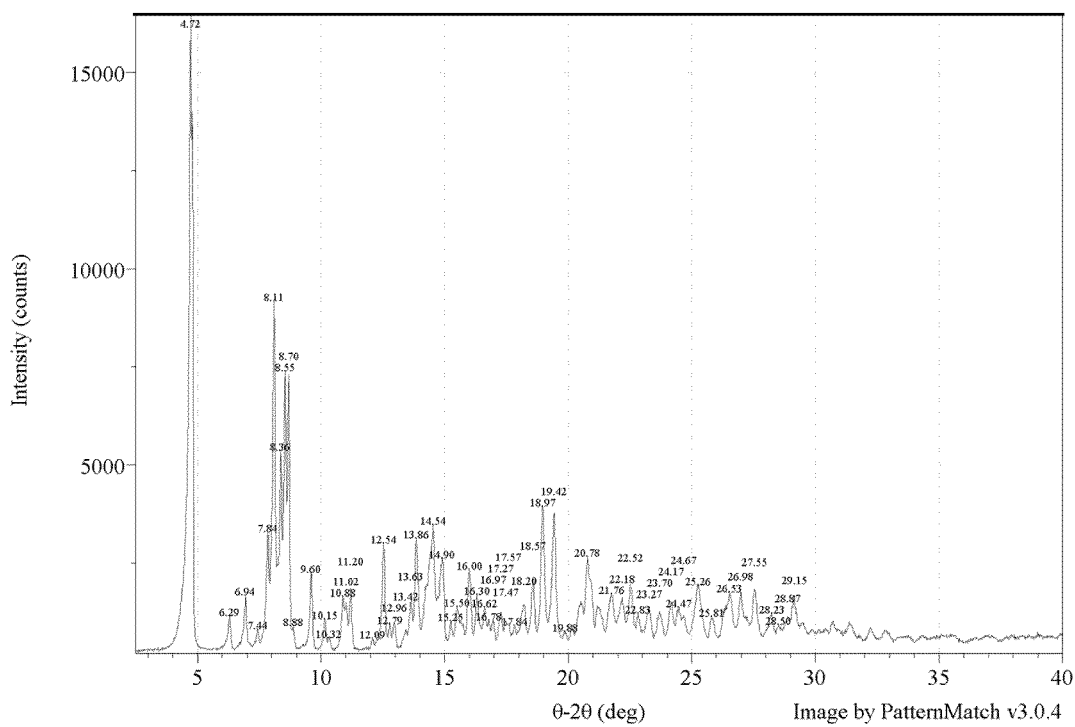
FIG. 2 shows a XRPD pattern of rifaximin Form Mu with Observed Peaks listed.
Figure 3:
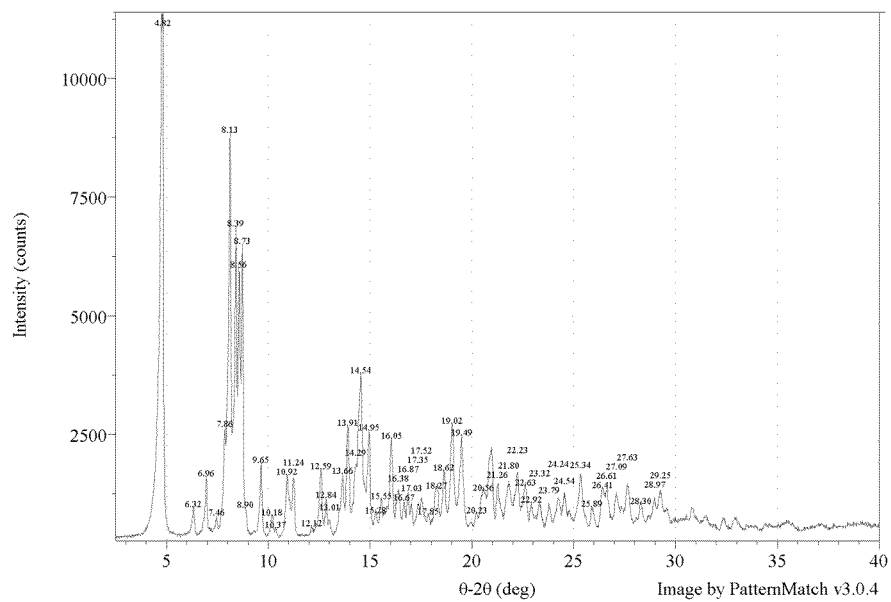
FIG. 3 shows a XRPD pattern of rifaximin Form Mu with Observed Peaks listed.

In one embodiment, Form Mu of rifaximin comprises an XRPD substantially similar to one or more of FIGS. 1-3.

Figure 6:
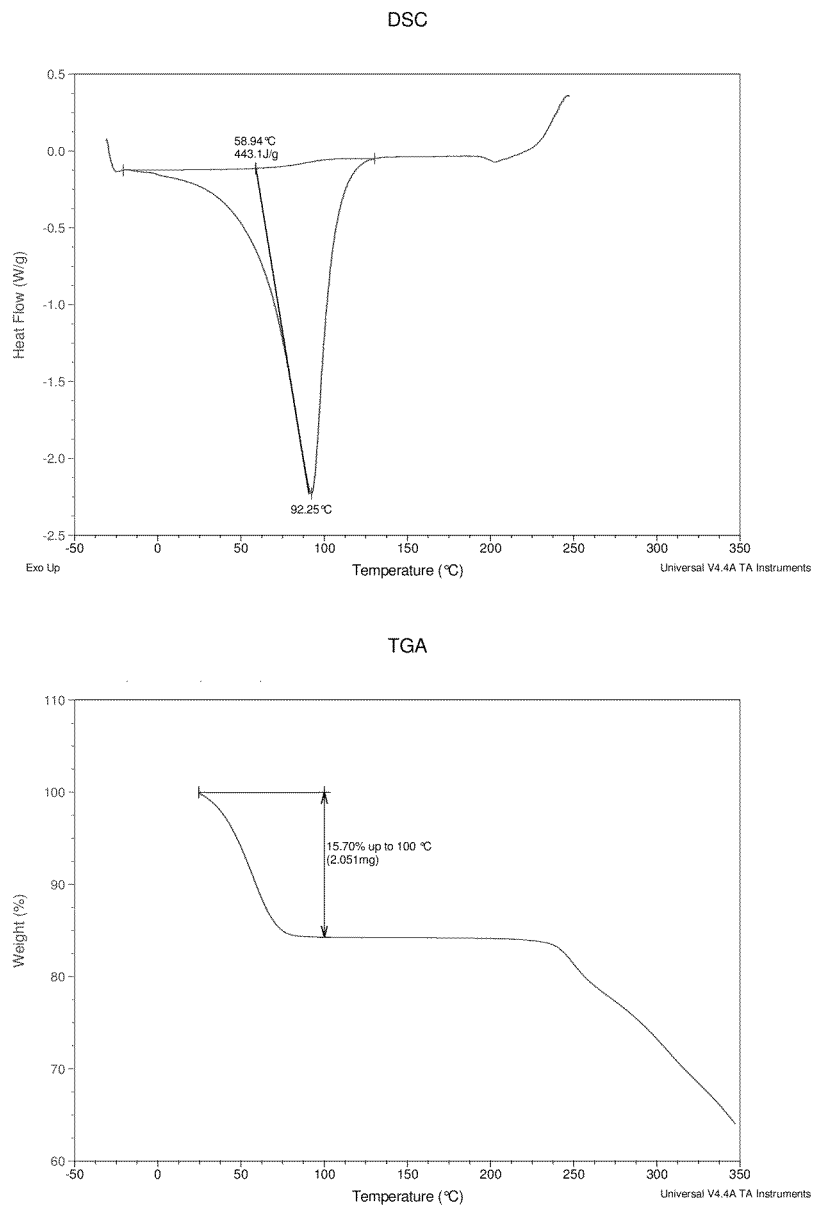
FIG. 6 shows DSC and TGA thermograms for rifaximin Form Mu.

In one embodiment, Form Mu of rifaximin comprises a DSC or TGA thermogram substantially similar to FIG. 6.

In one embodiment, Form Mu of rifaximin comprises the peaks listed in Tables 12-15.

In one embodiment, Form Mu of rifaximin exhibits an X-ray powder diffraction pattern comprising peaks expressed in degrees 2θ comprising one or more peaks listed in FIG. 2 and/or FIG. 3.

In one embodiment, Form Mu of rifaximin exhibits an X-ray powder diffraction pattern comprising peaks expressed in degrees 2θ at two more of about 4.72, about 4.79, about 6.29, about 6.94, about 7.44, about 7.84, about 8.11, about 8.36, about 8.55, about 8.70, about 8.88, about 9.60, about 10.15, about 10.32, about 10.88, about 11.02, about 11.20, about 12.09, about 12.54, about 12.79, about 12.96, about 13.42, about 13.63, about 13.86, about 14.54, about 14.90, about 15.25, about 15.50, about 16.00, about 16.30, about 16.62, about 16.78, about 16.97, about 17.27, about 17.47, about 17.57, about 17.84, about 18.20, about 18.57, about 18.97, about 19.42, about 19.88, about 20.78, about 21.76, about 22.18, about 22.52, about 22.83, about 23.27, about 23.70, about 24.17, about 24.47, about 24.67, about 25.26, about 25.81, about 26.53, about 26.98, about 27.55, about 28.23, about 28.50, about 28.87, and about 29.15.

In one embodiment, Form Mu of rifaximin exhibits an X-ray powder diffraction pattern comprising peaks expressed in degrees 2θ at two more of about 4.72, about 4.79, and about 6.29.

In one embodiment, Form Mu of rifaximin exhibits an X-ray powder diffraction pattern comprising peaks expressed in degrees 2θ at two more of about 4.72, about 4.79, and about 7.44.

In one embodiment, Form Mu of rifaximin exhibits an X-ray powder diffraction pattern comprising peaks expressed in degrees 2θ at two more of about 4.72, about 4.79, and about 8.11.

In one embodiment, Form Mu of rifaximin exhibits an X-ray powder diffraction pattern comprising peaks expressed in degrees 2θ at two more of about 4.72, about 8.11, and about 10.32.

In one embodiment, Form Mu of rifaximin exhibits an X-ray powder diffraction pattern comprising peaks expressed in degrees 2θ at two more of about 4.72, about 6.94, and about 11.20.

In one embodiment, Form Mu of rifaximin exhibits an X-ray powder diffraction pattern comprising peaks expressed in degrees 2θ at two more of about 4.72, about 4.79, and about 12.09.

In one embodiment, Form Mu of rifaximin exhibits an X-ray powder diffraction pattern comprising peaks expressed in degrees 2θ at about 4.72, about 4.79, about 7.84, about 8.11, about 8.36, about 8.55, about 8.70, about 9.60, and about 12.54.

In one embodiment, Form Mu of rifaximin exhibits an X-ray powder diffraction pattern comprising peaks expressed in degrees 2θ at two more of about 4.72, about 4.79, about 6.29, about 6.94, about 7.44, about 7.84, about 8.11, about 8.36, about 8.55, about 8.70, about 8.88, and about 9.60.

In one embodiment, Form Mu of rifaximin exhibits an X-ray powder diffraction pattern comprising peaks expressed in degrees 2θ at two more of about 4.72, about 4.79, about 6.29, about 6.94, about 7.44, about 7.84, about 8.11, about 8.36, about 8.55, about 8.70, about 8.88, about 9.60, about 10.15, about 10.32, about 10.88, about 11.02, and about 11.20.

Figure 9:
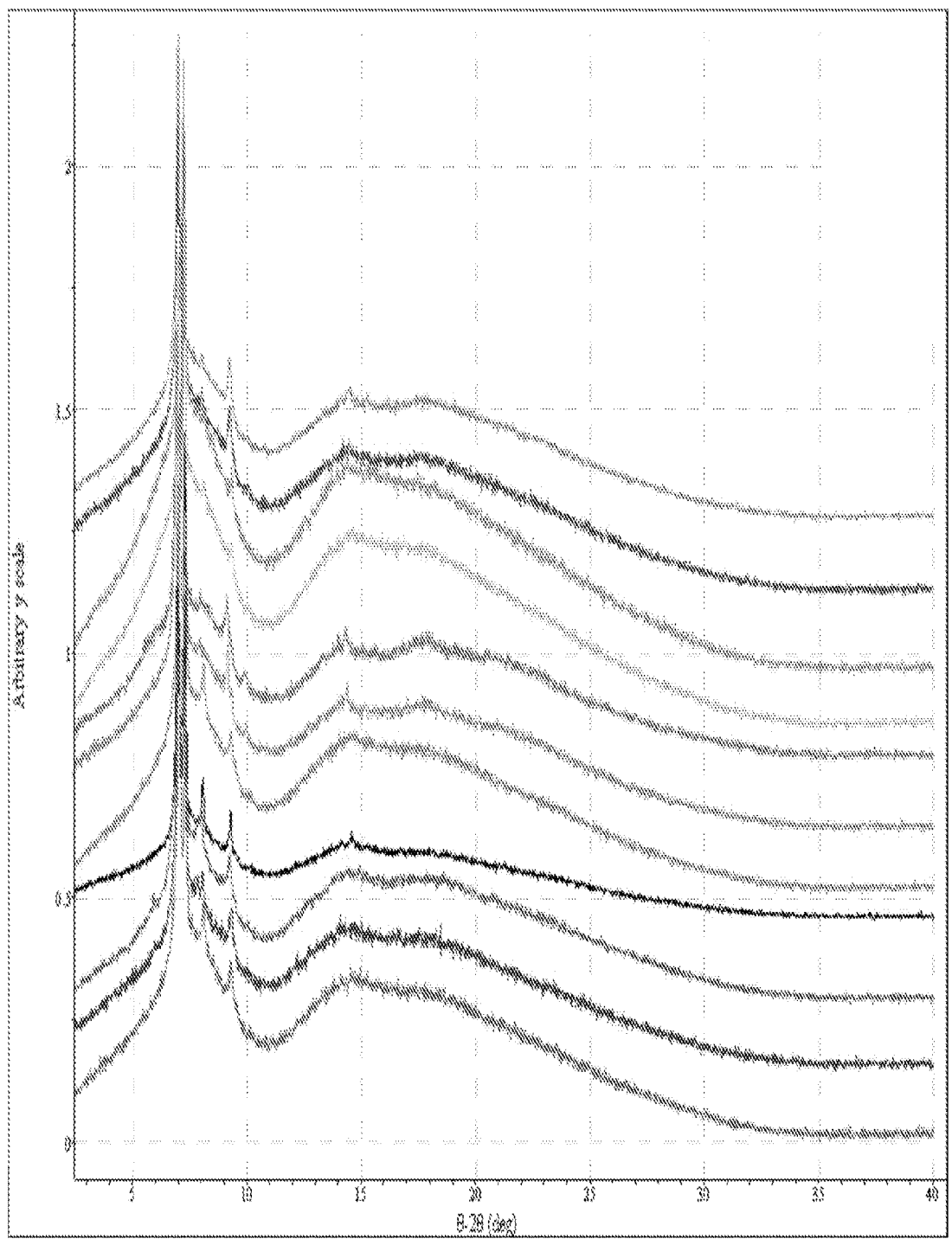
FIG. 9 is an XRPD pattern illustrating the consistency of the pattern for rifaximin Form Pi.
Figure 10:
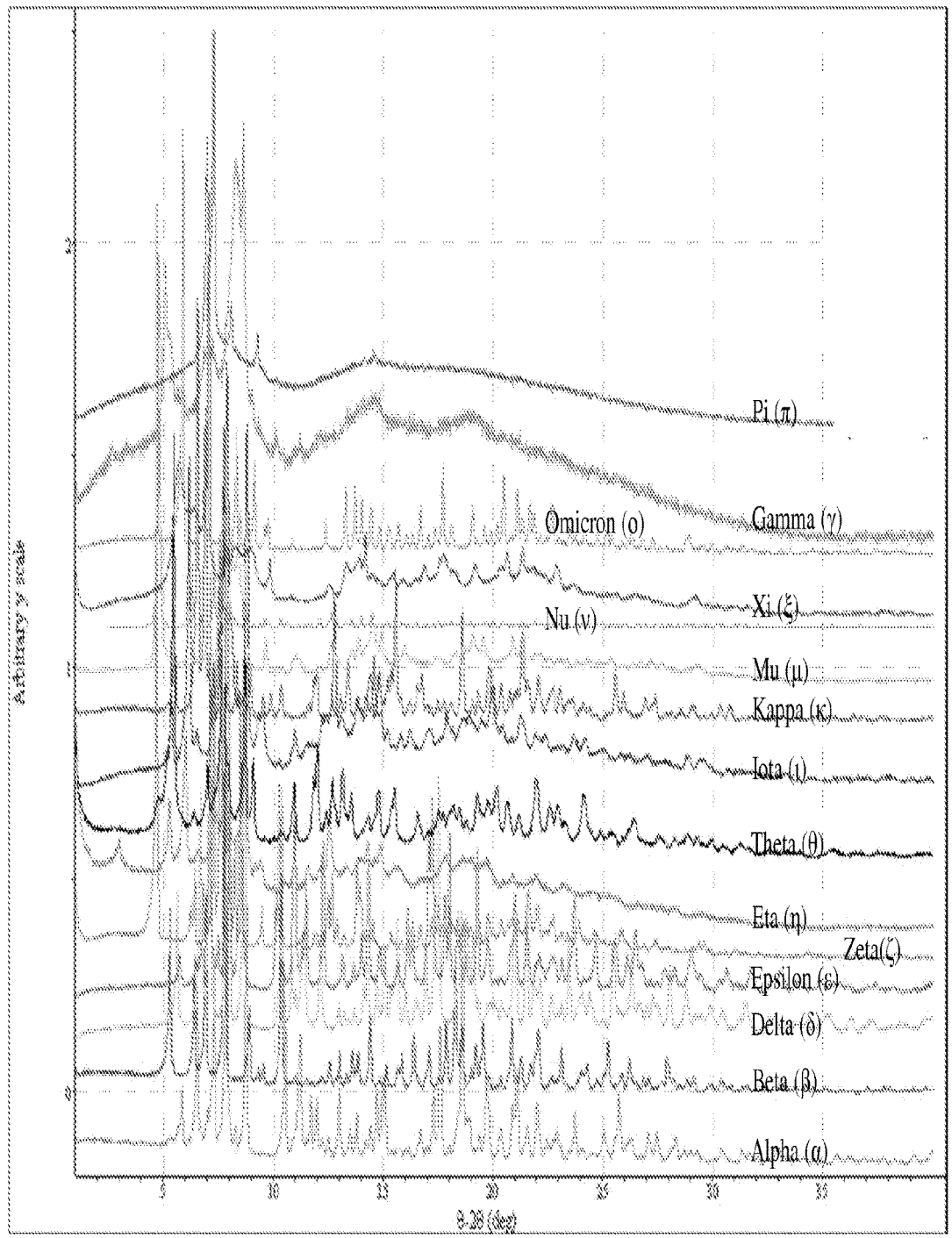
FIG. 10 is a comparison of the XRPD pattern for rifaximin Form Pi relative to that of the other polymorphs of rifaximin.

In one embodiment, Form Pi of rifaximin comprises an X-ray powder diffraction pattern substantially similar to that of FIG. 9.

Figure 12:
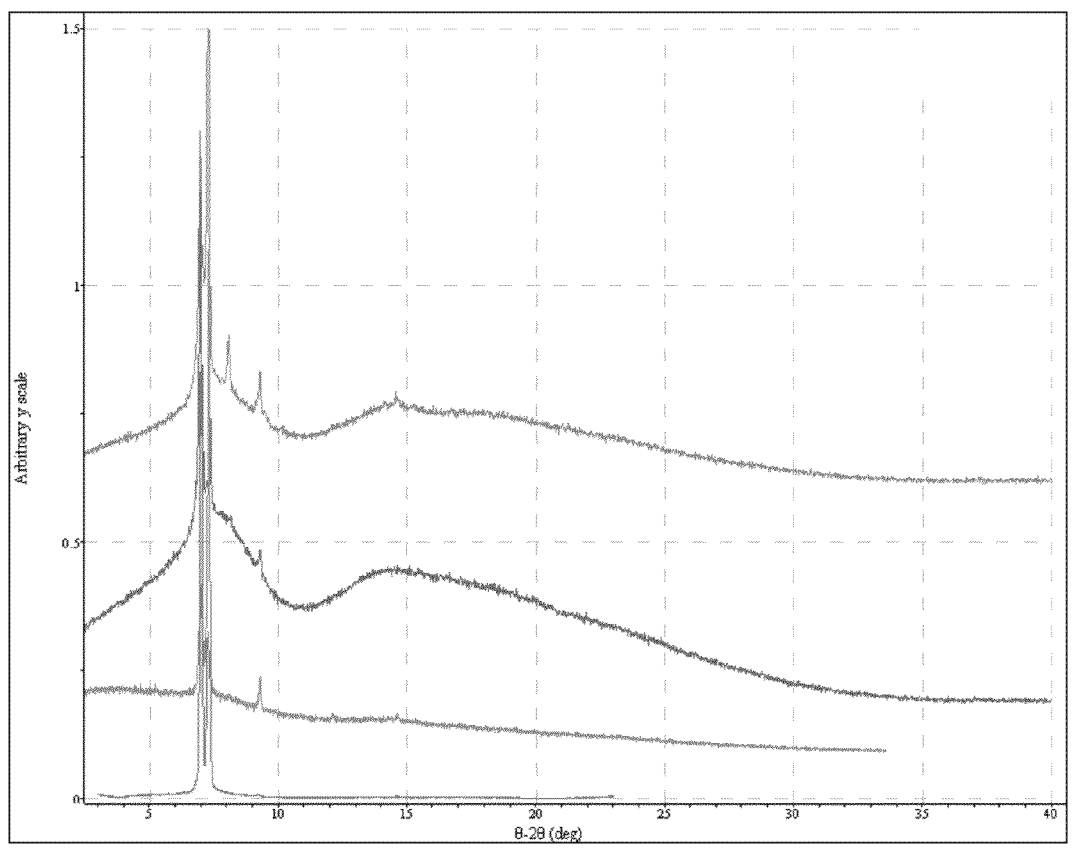
FIG. 12 is an XRPD pattern of different samples of rifaximin Form Pi.

In one embodiment, Form Pi of rifaximin comprises an X-ray powder diffraction pattern substantially similar to that of FIG. 12.

Figure 13:
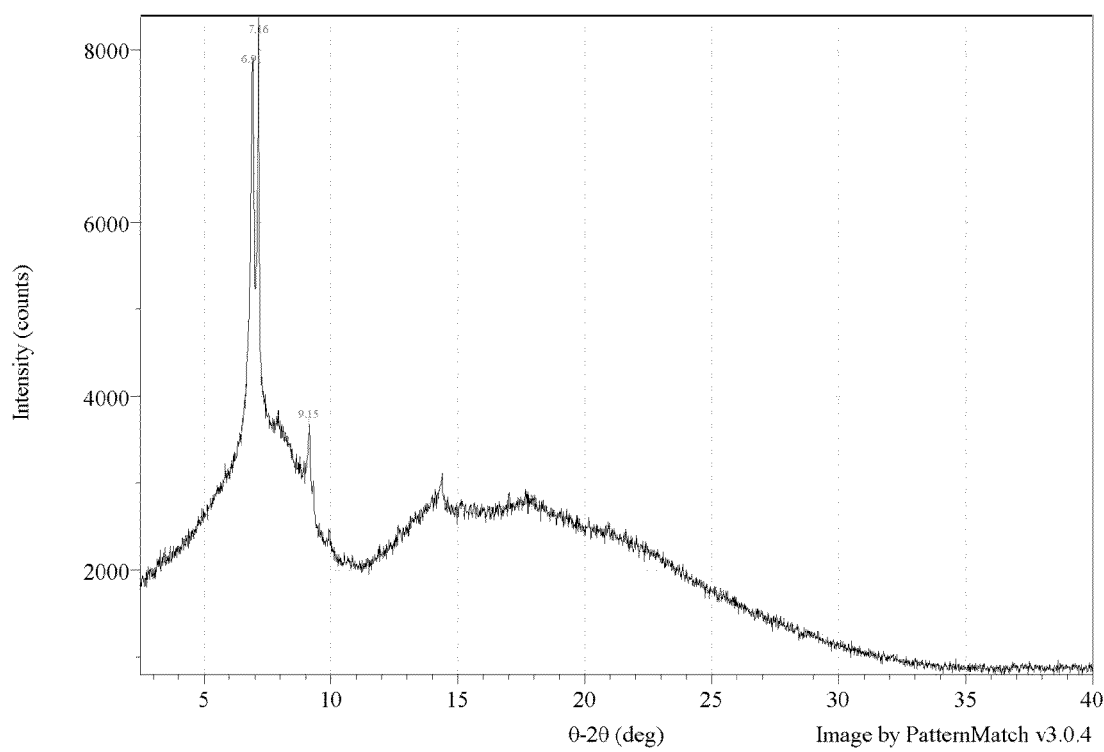
FIG. 13 is an XRPD pattern of observed peaks for rifaximin Form Pi.

In one embodiment, Form Pi of rifaximin comprises an X-ray powder diffraction pattern substantially similar to that of FIG. 13.

Figure 14:
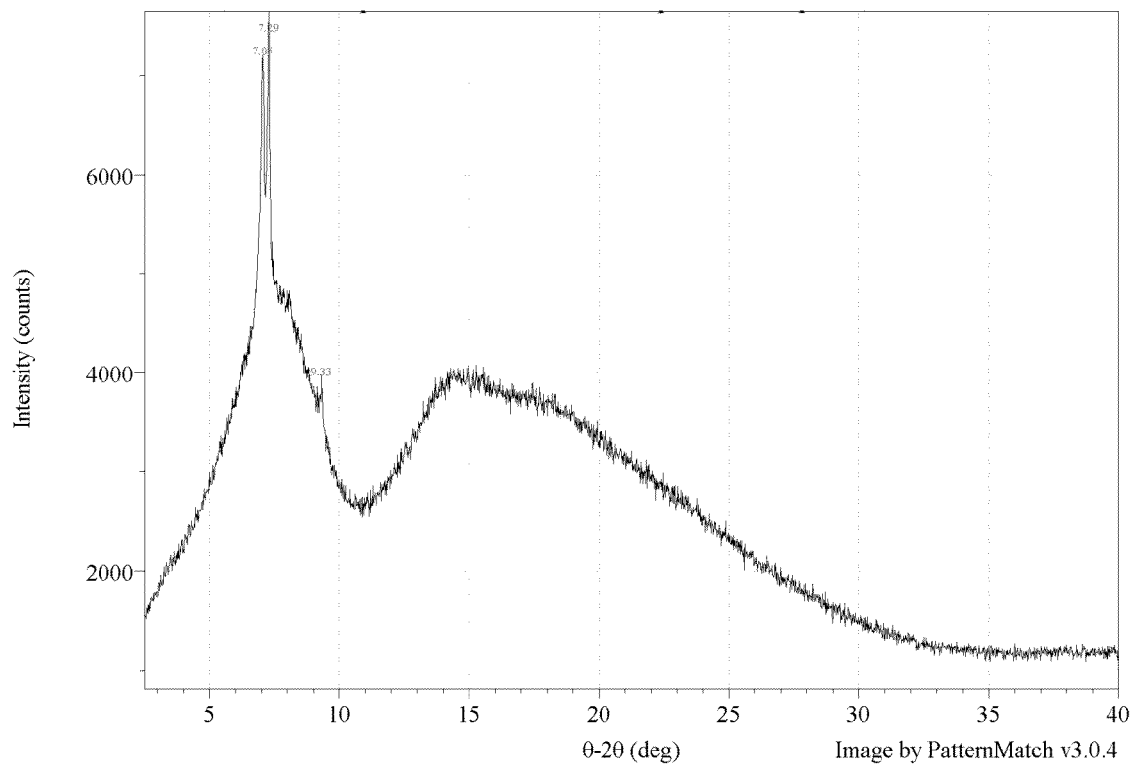
FIG. 14 is an XRPD pattern of observed peaks for rifaximin Form Pi.

In one embodiment, Form Pi of rifaximin comprises an X-ray powder diffraction pattern substantially similar to that of FIG. 14.

Figure 15:
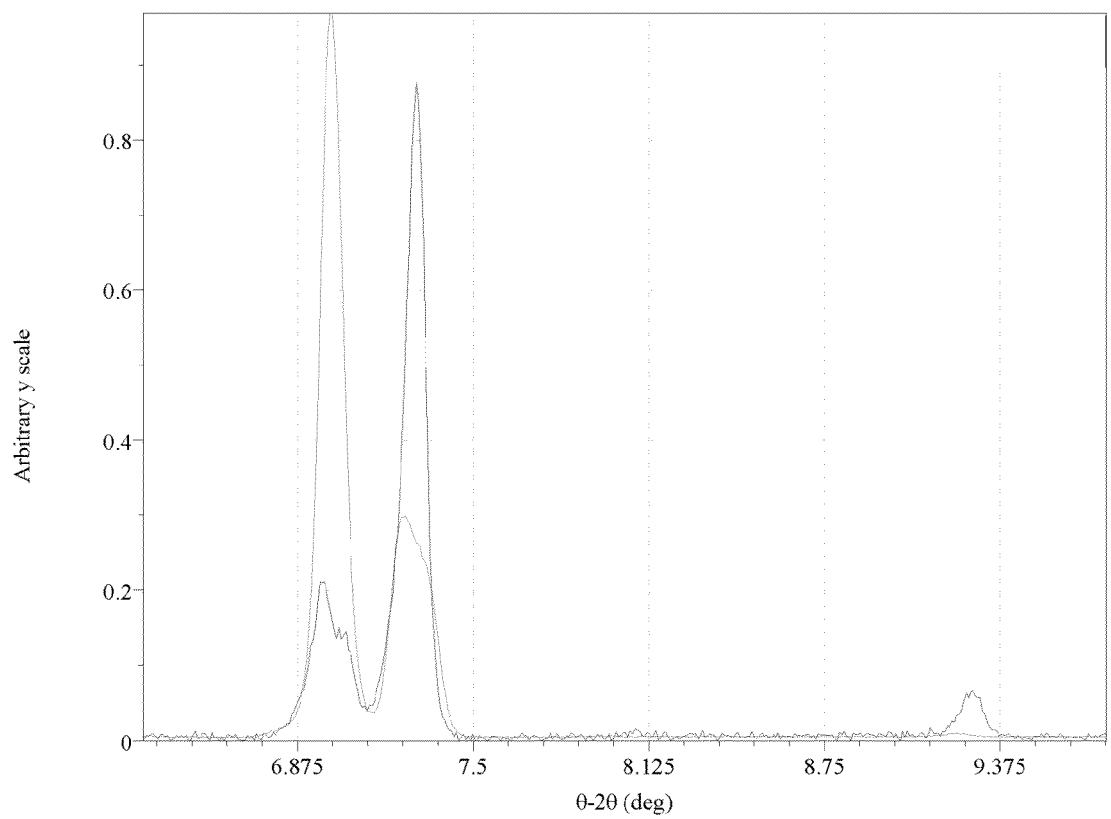
FIG. 15 shows the variation between the relative intensities and peak positions of the two prominent Bragg peaks of rifaximin Form Pi, due to preferred orientation of the faceted crystals.

In one embodiment, Form Pi of rifaximin comprises relative intensities and peak positions of two prominent Bragg peaks substantially similar to that of FIG. 15.

Figure 16:
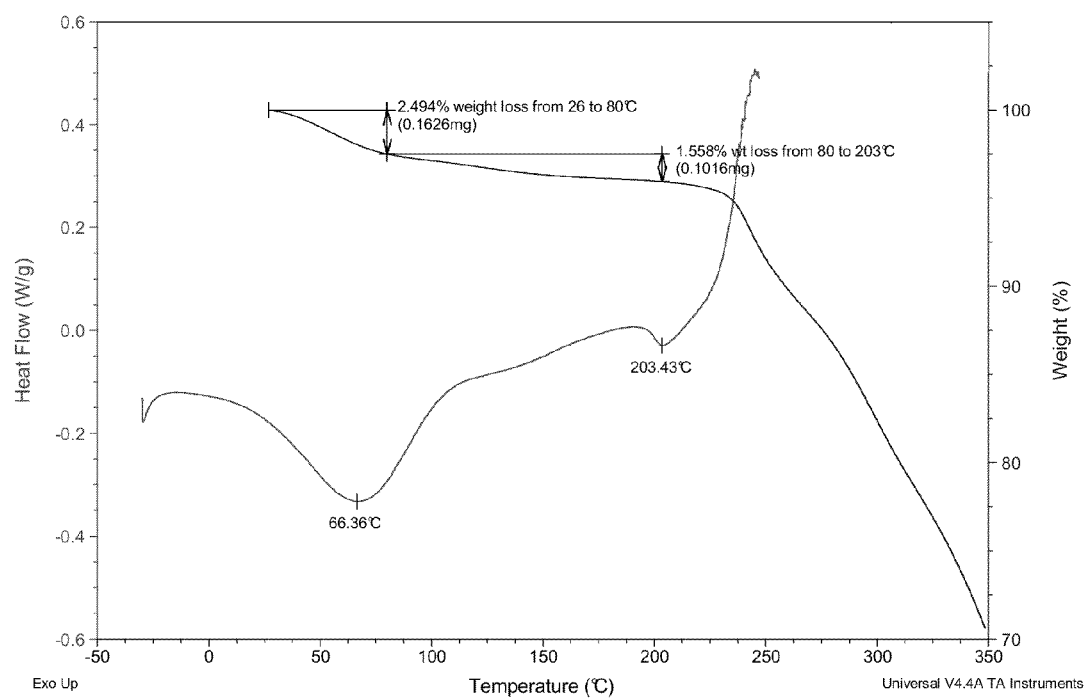
FIG. 16 shows DSC and TGA thermograms of rifaximin Form Pi.

In one embodiment, Form Pi of rifaximin comprises a DSC thermogram substantially similar to that of FIG. 16.

Figure 17:
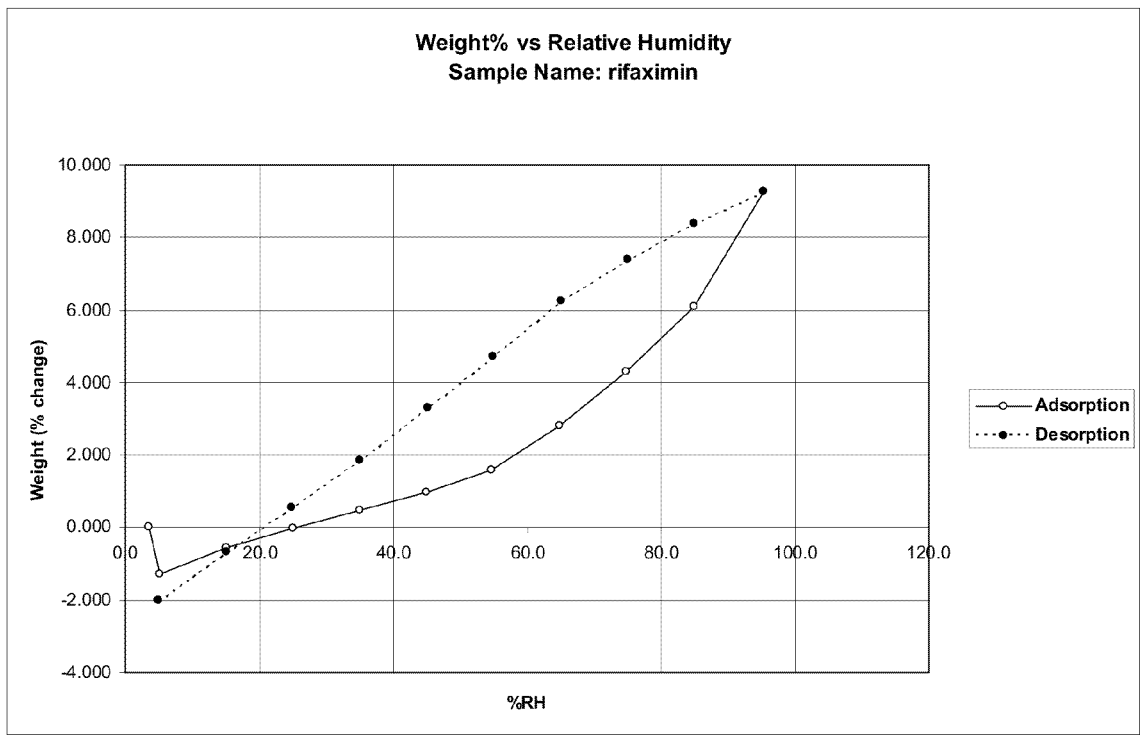
FIG. 17 shows moisture sorption (DVS) data of rifaximin Form Pi.

In one embodiment, Form Pi of rifaximin comprises moisture sorption data (DVS) substantially similar to that of FIG. 17.

Figure 18:
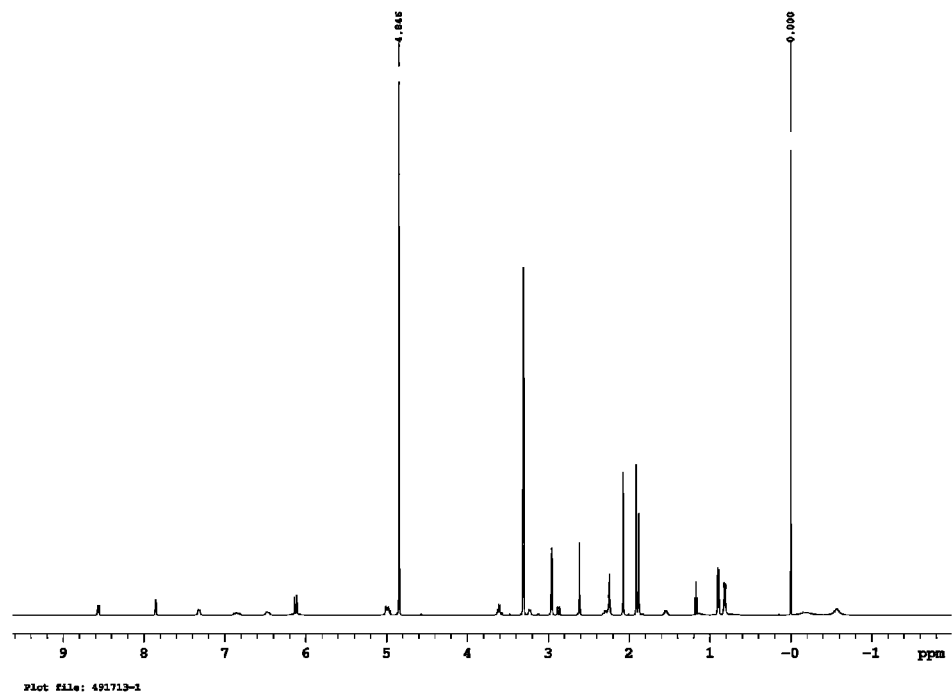
FIG. 18 shows the solution proton NMR spectrum of rifaximin Form Pi.

In one embodiment, Form Pi of rifaximin comprises a solution proton NMR spectra substantially similar to that of FIG. 18.

Figure 19:
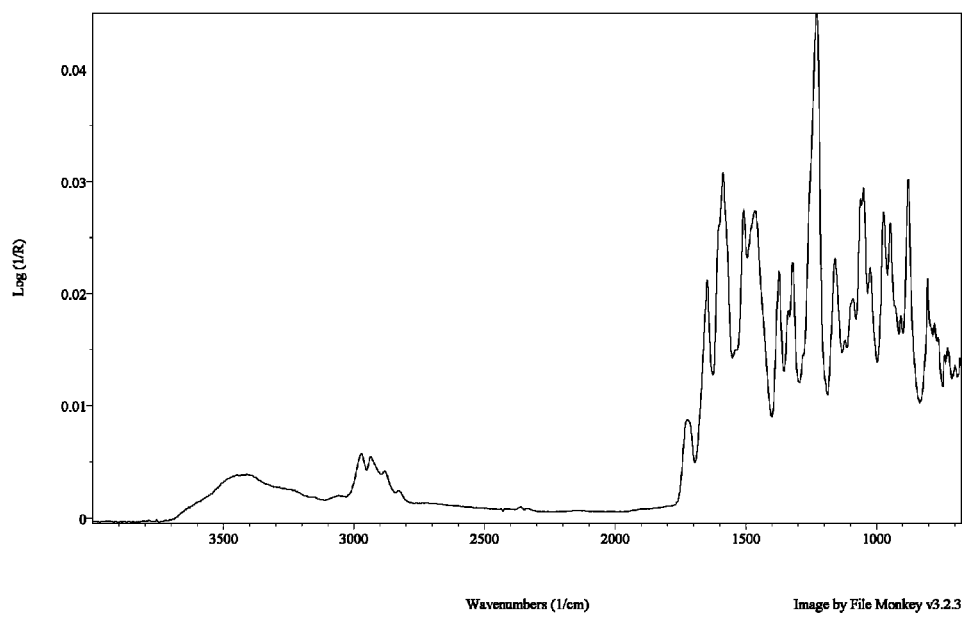
FIG. 19 shows the ATR-IR spectrum rifaximin Form Pi.

In one embodiment, Form Pi of rifaximin comprises an ATR-IR spectrum substantially similar to that of FIG. 19.

Figure 20:
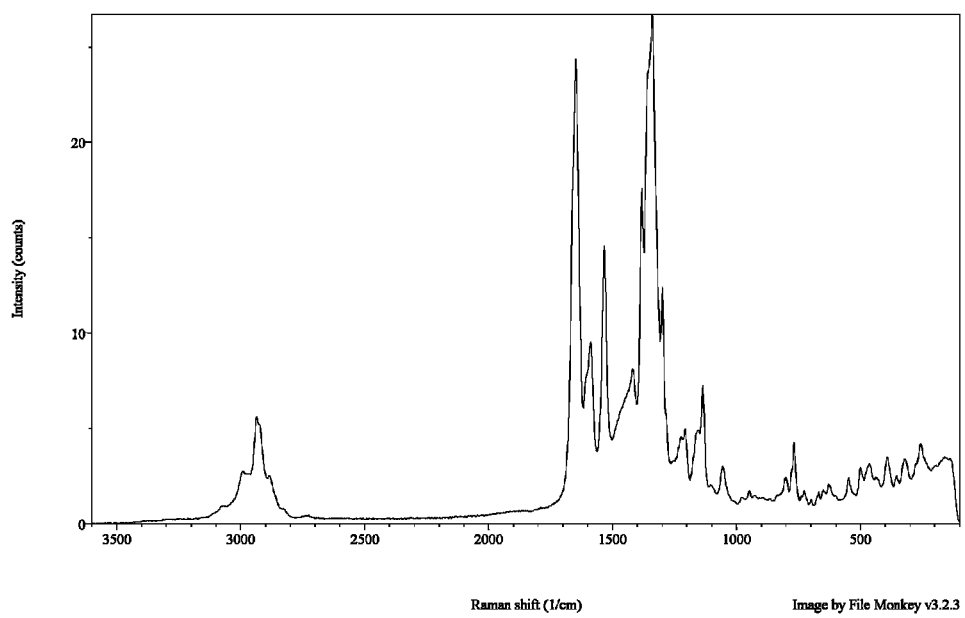
FIG. 20 shows the Raman spectrum of rifaximin Form Pi.

In one embodiment, Form Pi of rifaximin comprises a Raman spectrum substantially similar to that of FIG. 20.

Figure 21:
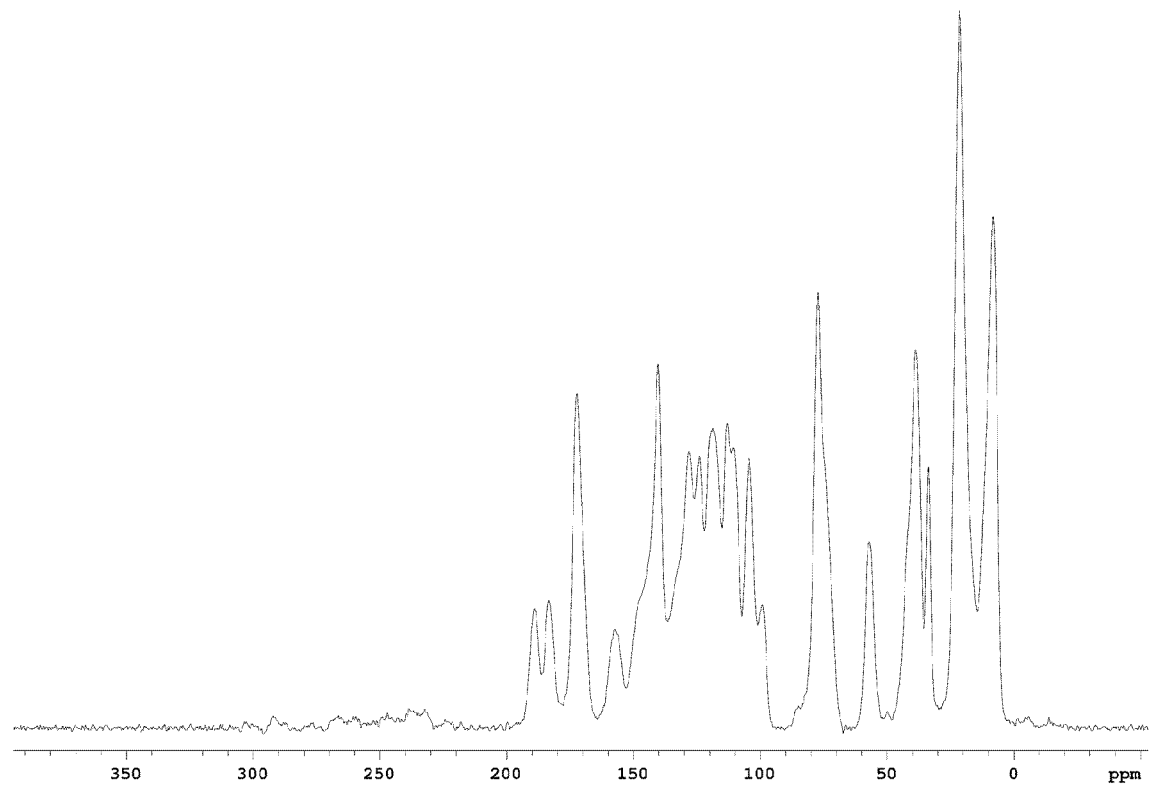
FIG. 21 shows the solid state carbon NMR spectrum of rifaximin Form Pi.

In one embodiment, Form Pi of rifaximin comprises a solid state carbon NMR spectrum substantially similar to that of FIG. 21.

In one embodiment, Form Pi of rifaximin exhibits an X-ray powder diffraction pattern comprising peaks expressed in degrees 2θ at about 6.91 and about 7.16.

In one embodiment, Form Pi of rifaximin exhibits an X-ray powder diffraction pattern comprising peaks expressed in degrees 2θ at about 6.91, about 7.16, and about 9.15.

In one embodiment, Form Pi of rifaximin exhibits an X-ray powder diffraction pattern comprising peaks expressed in degrees 2θ at about 7.05 and about 7.29.

In one embodiment, Form Pi of rifaximin exhibits an X-ray powder diffraction pattern comprising peaks expressed in degrees 2θ at about 7.05, about 7.29, and about 9.33.

In one embodiment, Form Pi of rifaximin exhibits an X-ray powder diffraction pattern comprising peaks expressed in degrees 2θ at about 6.91-7.05 and about 7.16-7.29.

In one embodiment, Form Pi of rifaximin exhibits an X-ray powder diffraction pattern comprising peaks expressed in degrees 2θ at about 6.91-7.05, about 7.16-7.29, and about 9.15-9.33.

Figure 32:
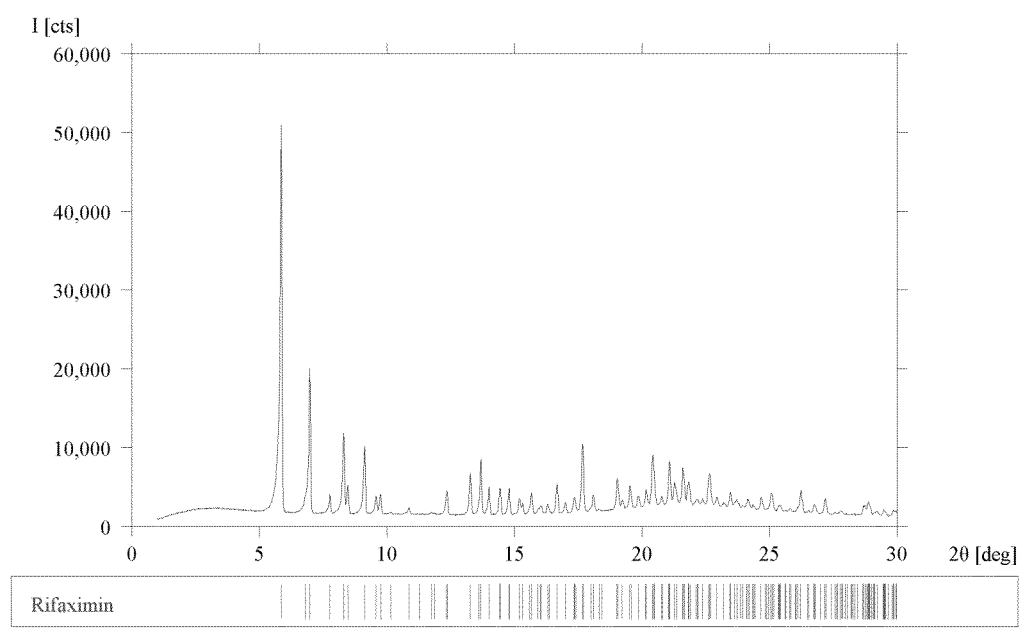
FIG. 32 shows an indexing solution of rifaximin Form Omicron.

In one embodiment, Form Omicron of rifaximin comprises an XRPD substantially similar to FIG. 32.

In one embodiment, Form Omicron of rifaximin comprises an XRPD substantially similar to FIG. 34.

In one embodiment, Form Omicron of rifaximin comprises index unit cell parameters substantially similar to that of FIG. 33.

In one embodiment, Form Omicron of rifaximin comprises DSC and TGA thermograms substantially similar to that of FIG. 35.

In one embodiment, Form Omicron of rifaximin comprises moisture sorption data (DVS) substantially similar to that of FIG. 36.

In one embodiment, Form Omicron of rifaximin comprises moisture sorption data (DVS) of rifaximin Form Omicron and post-DVS sample, Form Iota substantially similar to that of FIG. 37.

In one embodiment, Form Omicron of rifaximin comprises an ATR-IR spectrum substantially similar to that of FIG. 38.

In one embodiment, Form Omicron of rifaximin comprises a Raman spectrum substantially similar to that of FIG. 39.

In one embodiment, Form Omicron of rifaximin comprises a solution proton NMR spectrum substantially similar to that of FIG. 40.

In one embodiment, Form Omicron of rifaximin comprises a solid state carbon NMR spectrum substantially similar to that of FIG. 41.

In one embodiment, Form Omicron of rifaximin exhibits an X-ray powder diffraction pattern comprising peaks expressed in degrees 2θ at two or more of about 5.87, about 6.99, and about 7.77.

In one embodiment, Form Omicron of rifaximin exhibits an X-ray powder diffraction pattern comprising peaks expressed in degrees 2θ at two or more of about 5.87, about 6.99, and about 8.31.

In one embodiment, Form Omicron of rifaximin exhibits an X-ray powder diffraction pattern comprising peaks expressed in degrees 2θ at two or more of about 5.87, about 6.99, and about 8.47.

In one embodiment, Form Omicron of rifaximin exhibits an X-ray powder diffraction pattern comprising peaks expressed in degrees 2θ at two or more of about 5.87, about 6.99, and about 9.13.

In one embodiment, Form Omicron of rifaximin exhibits an X-ray powder diffraction pattern comprising peaks expressed in degrees 2θ at two or more of about 5.87, about 6.99, and about 9.58.

In one embodiment, Form Omicron of rifaximin exhibits an X-ray powder diffraction pattern comprising peaks expressed in degrees 2θ at two or more of about 5.87, about 6.99, and about 9.74.

In one embodiment, Form Omicron of rifaximin exhibits an X-ray powder diffraction pattern comprising peaks expressed in degrees 2θ at two or more of about 5.87, about 6.99, and about 12.35.

In one embodiment, Form Omicron of rifaximin exhibits an X-ray powder diffraction pattern comprising peaks expressed in degrees 2θ at two or more of about 5.87, about 6.99, and about 13.27.

In one embodiment, Form Omicron of rifaximin exhibits an X-ray powder diffraction pattern comprising peaks expressed in degrees 2θ at two or more of about 5.87, about 6.99, and about 13.69.

In one embodiment, Form Omicron of rifaximin exhibits an X-ray powder diffraction pattern comprising peaks expressed in degrees 2θ at two or more of about 5.87, about 6.99, about 8.31, about 9.13, and about 13.27.

In one embodiment, Form Omicron of rifaximin exhibits an X-ray powder diffraction pattern comprising peaks expressed in degrees 2θ at two or more of about 5.87, about 6.99, about 8.31, about 9.13, about 13.27, and about 13.69.

In one embodiment, Form Omicron of rifaximin exhibits an X-ray powder diffraction pattern comprising peaks expressed in degrees 2θ at two or more of about 5.87, about 6.99, about 8.31, about 9.13, about 13.27, about 13.69, and about 17.67.

In one embodiment, Form Omicron of rifaximin exhibits an X-ray powder diffraction pattern comprising peaks expressed in degrees 2θ at two or more of about 5.87, about 6.99, about 7.77, about 8.31, about 9.13, about 13.27, about 13.69, and about 17.67.

In one embodiment, Form Omicron of rifaximin exhibits an X-ray powder diffraction pattern comprising peaks expressed in degrees 2θ at two or more of about 5.87, about 6.99, about 8.31, about 9.13, about 9.58, about 9.74, about 13.27, about 13.69, and about 17.67.

In one embodiment, Form Omicron of rifaximin exhibits an X-ray powder diffraction pattern comprising peaks expressed in degrees 2θ at two or more of about 5.87, about 6.99, about 7.77, about 8.31, about 8.47, about 9.13, about 9.58, about 9.74, about 10.86, about 12.35, about 13.27, about 13.69, about 14.01, about 14.44, about 14.79, about 15.19, about 15.33, about 15.68, about 15.94, about 16.04, about 16.31, about 16.66, about 17.00, about 17.35, about 17.67, about 18.08, about 19.04, about 19.24, about 19.52, about 19.85, about 20.17, about 20.42, about 20.76, about 21.07, about 21.28, about 21.61, about 21.83, about 22.14, about 22.36, about 22.65, about 22.93, about 23.20, about 23.46, about 23.71, about 24.15, about 24.35, about 24.67, about 25.07, about 25.40, about 25.80, about 26.22, about 26.54, about 26.76, about 27.17, about 27.78, about 28.69, about 28.88, about 29.21, about 29.46, about 23.71, about 24.15, about 24.35, about 24.67, about 25.07, about 25.40, about 25.80, about 26.22, about 26.54, about 26.76, about 27.17, about 27.78, about 28.69, about 28.88, about 29.21, and about 29.46.

Figure 42:
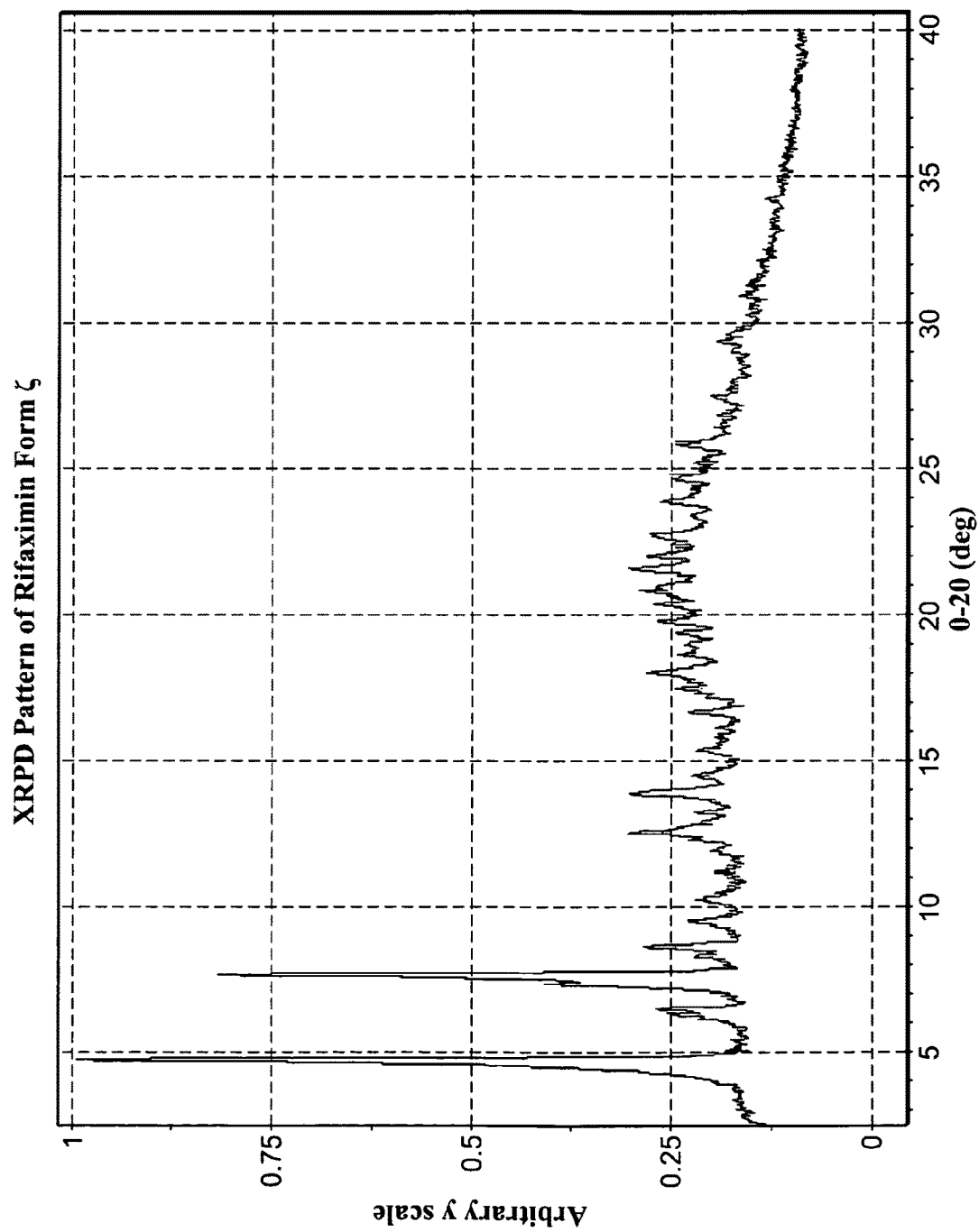
FIG. 42 is an exemplary XRPD Pattern of rifaximin Form Zeta.
Figure 43:
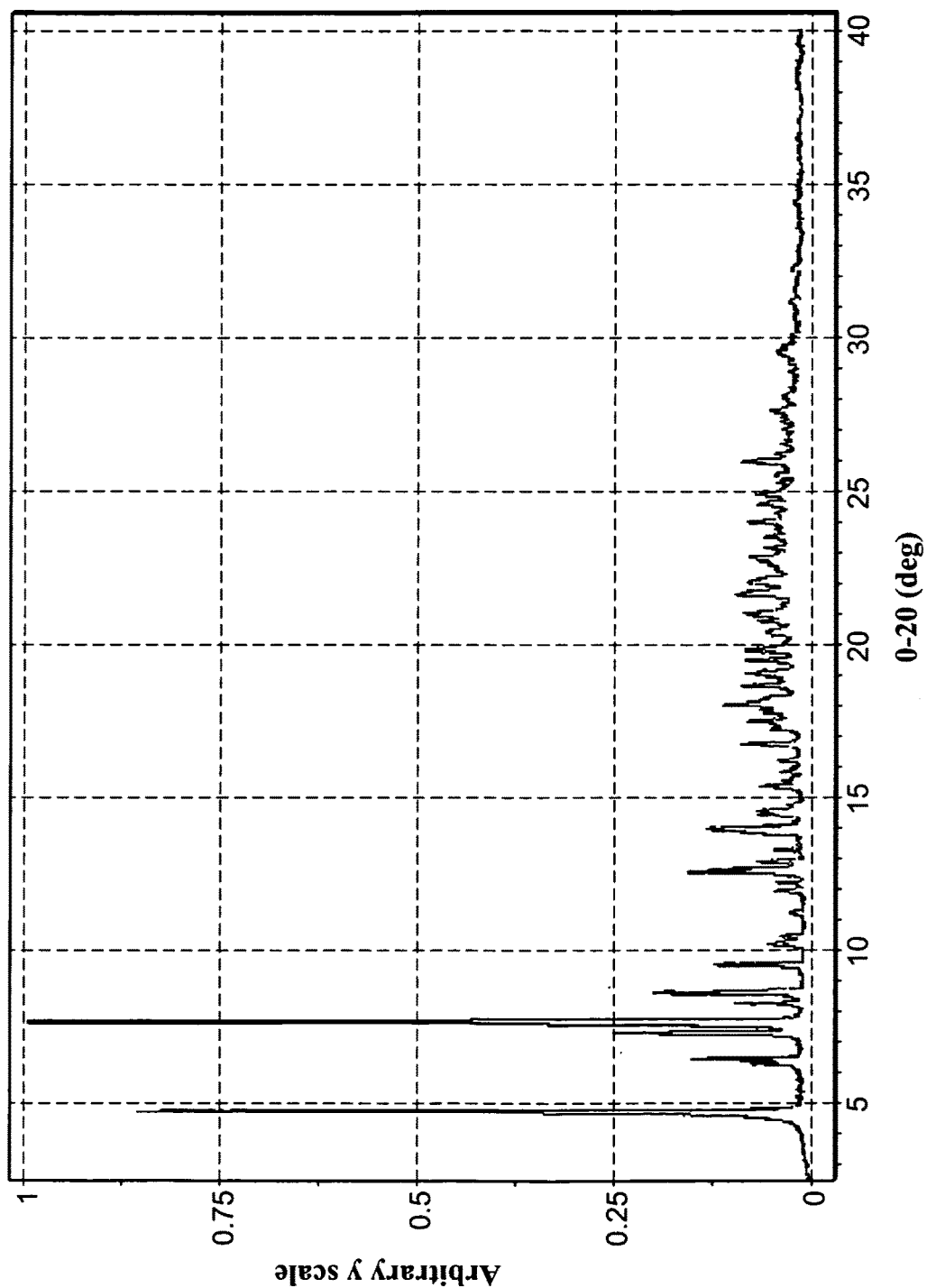
FIG. 43 depicts an exemplary XRPD pattern of rifaximin Form Zeta.

In one embodiment, Form Zeta of rifaximin comprises an X-ray powder diffraction pattern substantially similar to FIG. 42, and/or FIG. 43.

In one embodiment, Form Zeta of rifaximin exhibits an X-ray powder diffraction pattern comprising peaks expressed in degrees 2θ at two or more of about 4.7, about 7.6, and about 9.5; or about 4.7, about 7.3, and about 8.2; or about 7.6, about 8.6, and about 10.5; or about 8.2, about 8.6, and about 9.5; or about 10.2, about 12.6, and about 13.2; or about 7.3, about 10.5, and about 12.9; or about 7.3, about 7.6, about 8.2, about 8.6; or about 4.7, about 7.3, about 7.6, about 9.5, and about 10.5; or about 8.2, about 8.6, about 9.5, about 10.2, and about 10.5; or about 8.6, about 9.5, about 10.2, about 10.5, and about 11.2; or about 4.7, about 6.3, about 6.4, about 7.3, about 7.6, about 8.2, about 8.6, about 9.5, about 10.2, about 10.5, about 11.2, about 11.9, about 12.2, about 12.6, about 12.9, about 13.2.

In one embodiment, Form Zeta of rifaximin exhibits an X-ray powder diffraction pattern comprising peaks expressed in degrees 2θ at two or more of about 4.7 (doublet), about 7.6 (doublet), and about 9.5; or about 4.7 (doublet), about 7.3, and about 8.2; or about 7.6 (doublet), about 8.6, and about 10.5; or about 8.2, about 8.6, and about 9.5; or about 10.2 (triplet), about 12.6 (quintet), and about 13.2 (doublet); or about 7.3, about 10.5, and about 12.9 (doublet); or about 7.3, about 7.6 (doublet), about 8.2, about 8.6; or about 4.7 (doublet), about 7.3, about 7.6 (doublet), about 9.5, and about 10.5; or about 8.2, about 8.6, about 9.5, about 10.2 (triplet), and about 10.5; or about 8.6, about 9.5, about 10.2 (triplet), about 10.5, and about 11.2 (doublet); or about 4.7 (doublet), about 6.3, about 6.4, about 7.3, about 7.6 (doublet), about 8.2, about 8.6, about 9.5, about 10.2 (triplet), about 10.5, about 11.2 (doublet), about 11.9 (doublet), about 12.2 (weak), about 12.6 (quintet), about 12.9 (doublet), about 13.2 (doublet).

In one embodiment, Form Zeta of rifaximin exhibits an X-ray powder diffraction pattern comprising peaks expressed in degrees 2θ at two or more of about 4.7, about 7.6, and about 9.5; or about 4.7, about 7.3, and about 8.2.

In one embodiment, Form Zeta of rifaximin exhibits an X-ray powder diffraction pattern comprising peaks expressed in degrees 2θ at two or more of about 4.7 (doublet), about 7.6 (doublet), and about 9.5; or about 4.7 (doublet), about 7.3, and about 8.2.

In one embodiment, Form Zeta of rifaximin exhibits an X-ray powder diffraction pattern comprising peaks expressed in degrees 2θ at two or more of about 7.6, about 8.6, and about 10.5.

In one embodiment, Form Zeta of rifaximin exhibits an X-ray powder diffraction pattern comprising peaks expressed in degrees 2θ at two or more of about 7.6 (doublet), about 8.6, and about 10.5.

In one embodiment, Form Zeta of rifaximin exhibits an X-ray powder diffraction pattern comprising peaks expressed in degrees 2θ at two or more of about 8.2, about 8.6, and about 9.5.

In one embodiment, Form Zeta of rifaximin exhibits an X-ray powder diffraction pattern comprising peaks expressed in degrees 2θ at two or more of about 10.2, about 12.6, and about 13.2.

In one embodiment, Form Zeta of rifaximin exhibits an X-ray powder diffraction pattern comprising peaks expressed in degrees 2θ at two or more of about 10.2 (triplet), about 12.6 (quintet), and about 13.2 (doublet).

In one embodiment, Form Zeta of rifaximin exhibits an X-ray powder diffraction pattern comprising peaks expressed in degrees 2θ at two or more of about 7.3, about 10.5, and about 12.9.

In one embodiment, Form Zeta of rifaximin exhibits an X-ray powder diffraction pattern comprising peaks expressed in degrees 2θ at two or more of about 7.3, about 10.5, and about 12.9 (doublet).

In one embodiment, Form Zeta of rifaximin exhibits an X-ray powder diffraction pattern comprising peaks expressed in degrees 2θ at two or more of about 7.3, about 7.6, about 8.2, and about 8.6.

In one embodiment, Form Zeta of rifaximin exhibits an X-ray powder diffraction pattern comprising peaks expressed in degrees 2θ at two or more of about 7.3, about 7.6 (doublet), about 8.2, and about 8.6.

In one embodiment, Form Zeta of rifaximin exhibits an X-ray powder diffraction pattern comprising peaks expressed in degrees 2θ at two or more of about 4.7, about 7.3, about 7.6, about 9.5, and about 10.5.

In one embodiment, Form Zeta of rifaximin exhibits an X-ray powder diffraction pattern comprising peaks expressed in degrees 2θ at two or more of about 4.7 (doublet), about 7.3, about 7.6 (doublet), about 9.5, and about 10.5.

In one embodiment, Form Zeta of rifaximin exhibits an X-ray powder diffraction pattern comprising peaks expressed in degrees 2θ at two or more of about 8.2, about 8.6, about 9.5, about 10.2, and about 10.5.

In one embodiment, Form Zeta of rifaximin exhibits an X-ray powder diffraction pattern comprising peaks expressed in degrees 2θ at two or more of about 8.2, about 8.6, about 9.5, about 10.2 (triplet), and about 10.5.

In one embodiment, Form Zeta of rifaximin exhibits an X-ray powder diffraction pattern comprising peaks expressed in degrees 2θ at two or more of about 8.6, about 9.5, about 10.2, about 10.5, and about 11.2.

In one embodiment, Form Zeta of rifaximin exhibits an X-ray powder diffraction pattern comprising peaks expressed in degrees 2θ at two or more of about 8.6, about 9.5, about 10.2 (triplet), about 10.5, and about 11.2 (doublet).

In one embodiment, Form Zeta of rifaximin exhibits an X-ray powder diffraction pattern comprising peaks expressed in degrees 2θ at two or more of about 4.7, about 6.3, about 6.4, about 7.3, about 7.6, about 8.2, about 8.6, about 9.5, about 10.2, about 10.5, about 11.2, about 11.9, about 12.2, about 12.6, about 12.9, and about 13.2.

In one embodiment, Form Zeta of rifaximin exhibits an X-ray powder diffraction pattern comprising peaks expressed in degrees 2θ at two or more of about 4.7 (doublet), about 6.3, about 6.4, about 7.3, about 7.6 (doublet), about 8.2, about 8.6, about 9.5, about 10.2 (triplet), about 10.5, about 11.2 (doublet), about 11.9 (doublet), about 12.2 (weak), about 12.6 (quintet), about 12.9 (doublet), and about 13.2 (doublet).

Figure 44:
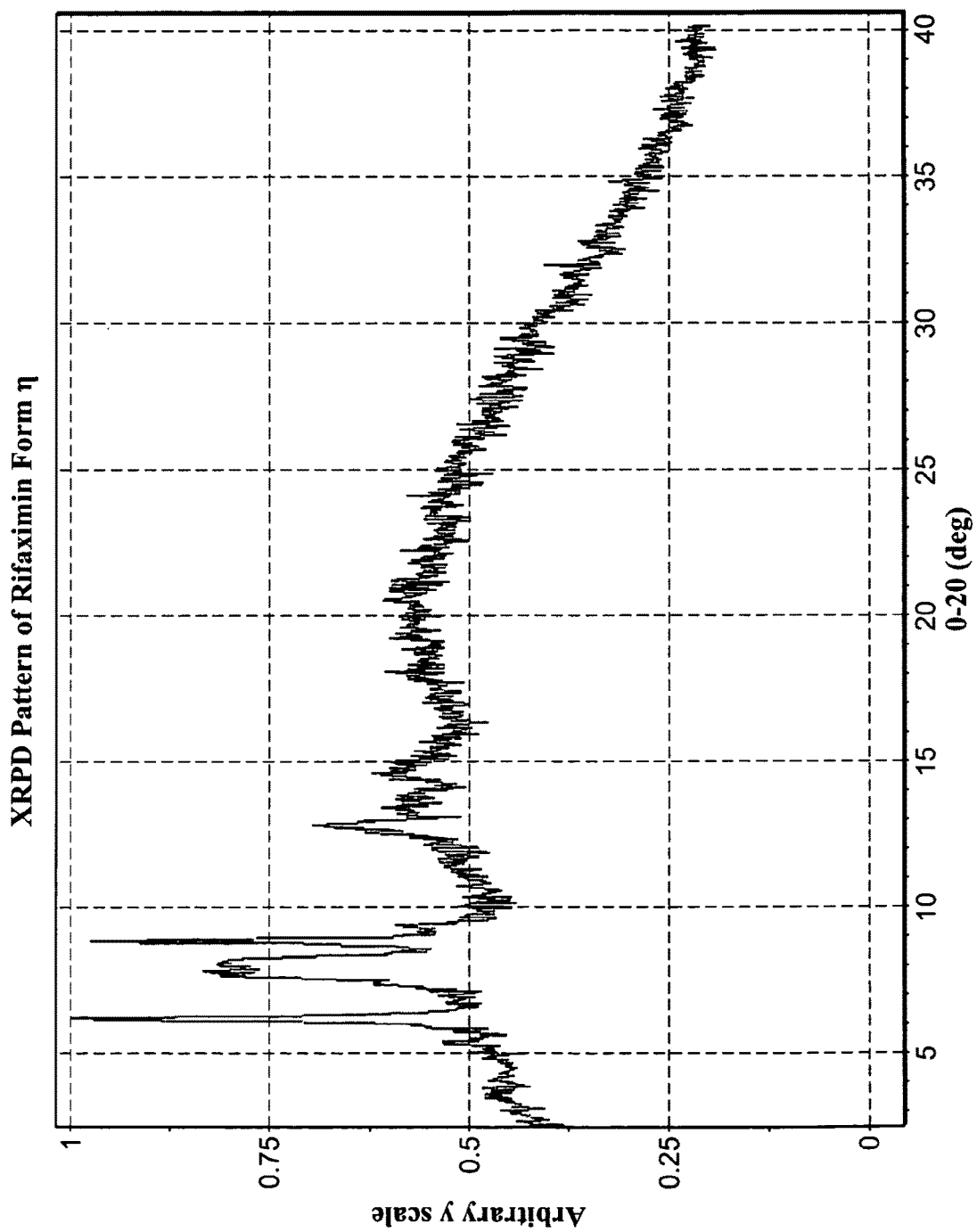
FIG. 44 is an exemplary XRPD pattern of rifaximin Form Eta.
Figure 45:
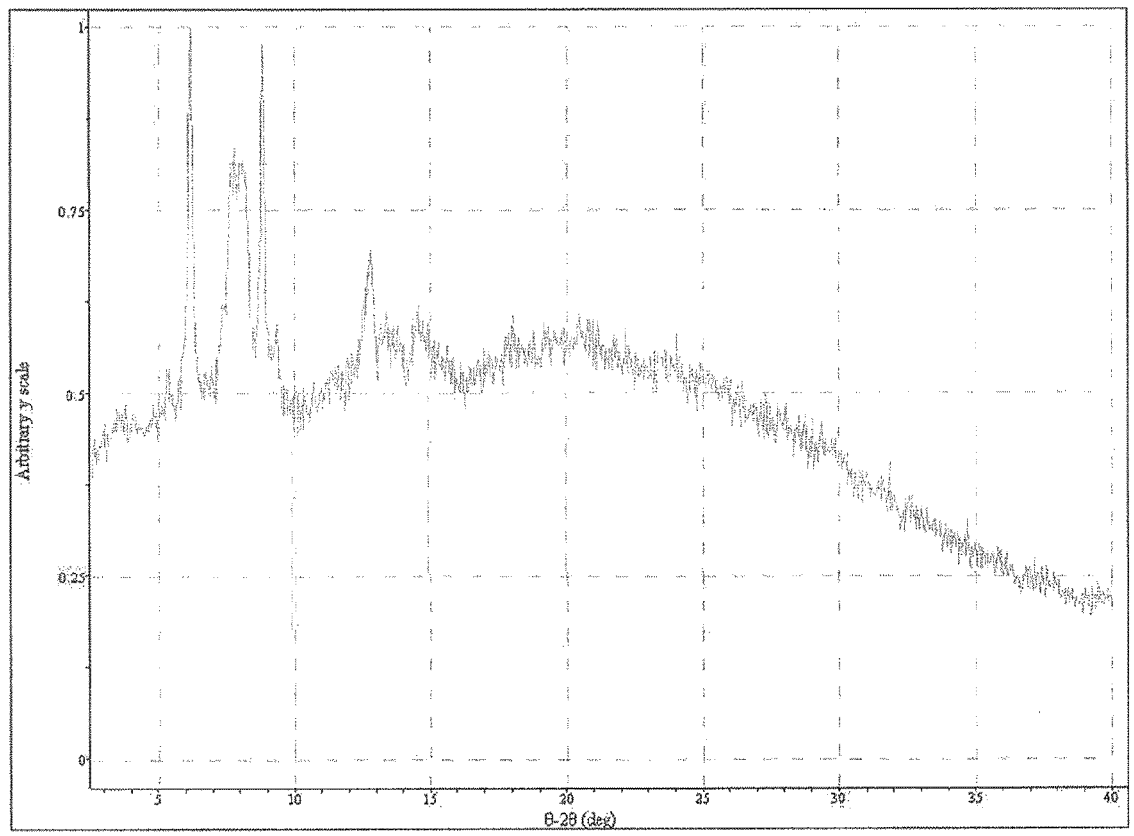
FIG. 45 depicts an exemplary XRPD pattern of rifaximin Form Eta.

In one embodiment, Form Eta of rifaximin comprises an X-ray powder diffraction pattern substantially similar to FIG. 44 and/or FIG. 45.

In one embodiment, Form Eta of rifaximin exhibits an X-ray powder diffraction pattern comprising peaks expressed in degrees 2θ, at two or more of about 6.1, about 7.3, and about 7.5; or about 6.1, about 7.3, and about 7.9; or about 6.1, about 7.3, and about 8.8; or about 6.1, about 7.3, and about 12.7; or about 6.1, about 7.5, and about 8.8; or about 6.1, about 7.5, and about 7.9; or about 5.3, about 6.1, and about 7.3; or about 5.3, about 6.1, and about 7.9; or about 5.3, about 6.1, and about 12.7; or about 5.3, about 6.1, and about 7.5; or about 5.3, about 6.1, and about 8.8; or about 6.1, about 7.3, about 7.5, about 7.9, about 8.8, and about 12.7; or about 5.3, about 6.1, about 7.3, about 7.5, about 7.9, about 8.8, and about 12.7; or about 5.3, about 6.1, about 7.3, about 7.9, about 8.8, and about 12.7; or about 5.3, about 6.1, about 7.3, about 7.5, about 8.8, and about 12.7; or about 5.3, about 6.1, about 7.3, about 7.5, about 7.9, about 8.8, and about 12.7.

In one embodiment, Form Eta of rifaximin exhibits an X-ray powder diffraction pattern comprising peaks expressed in degrees 2θ at two or more of about 6.1, about 7.3, and about 7.5; or about 6.1, about 7.3, and about 7.9.

In one embodiment, Form Eta of rifaximin exhibits an X-ray powder diffraction pattern comprising peaks expressed in degrees 2θ at two or more of about 6.1, about 7.3, and about 8.8.

In one embodiment, Form Eta of rifaximin exhibits an X-ray powder diffraction pattern comprising peaks expressed in degrees 2θ at two or more of about 6.1, about 7.3, and about 12.7.

In one embodiment, Form Eta of rifaximin exhibits an X-ray powder diffraction pattern comprising peaks expressed in degrees 2θ at two or more of about 6.1, about 7.5, and about 8.8.

In one embodiment, Form Eta of rifaximin exhibits an X-ray powder diffraction pattern comprising peaks expressed in degrees 2θ at two or more of about 6.1, about 7.5, and about 7.9.

In one embodiment, Form Eta of rifaximin exhibits an X-ray powder diffraction pattern comprising peaks expressed in degrees 2θ at two or more of about 5.3, about 6.1, and about 7.3.

In one embodiment, Form Eta of rifaximin exhibits an X-ray powder diffraction pattern comprising peaks expressed in degrees 2θ at two or more of about 5.3, about 6.1, and about 7.9.

In one embodiment, Form Eta of rifaximin exhibits an X-ray powder diffraction pattern comprising peaks expressed in degrees 2θ at two or more of about 5.3, about 6.1, and about 12.7.

In one embodiment, Form Eta of rifaximin exhibits an X-ray powder diffraction pattern comprising peaks expressed in degrees 2θ at two or more of about 5.3, about 6.1, and about 7.5.

In one embodiment, Form Eta of rifaximin exhibits an X-ray powder diffraction pattern comprising peaks expressed in degrees 2θ at two or more of about 5.3, about 6.1, and about 8.8; or about 6.1, about 7.3, about 7.5, about 7.9, about 8.8, and about 12.7.

In one embodiment, Form Eta of rifaximin exhibits an X-ray powder diffraction pattern comprising peaks expressed in degrees 2θ at two or more of about 5.3, about 6.1, about 7.3, about 7.5, about 7.9, about 8.8, and about 12.7.

In one embodiment, Form Eta of rifaximin exhibits an X-ray powder diffraction pattern comprising peaks expressed in degrees 2θ at two or more of about 5.3, about 6.1, about 7.3, about 7.9, about 8.8, and about 12.7.

In one embodiment, Form Eta of rifaximin exhibits an X-ray powder diffraction pattern comprising peaks expressed in degrees 2θ at two or more of about 5.3, about 6.1, about 7.3, about 7.5, about 8.8, and about 12.7.

In one embodiment, Form Eta of rifaximin exhibits an X-ray powder diffraction pattern comprising peaks expressed in degrees 2θ at two or more of about 5.3, about 6.1, about 7.3, about 7.5, about 7.9, about 8.8, and about 12.7.

Figure 46:
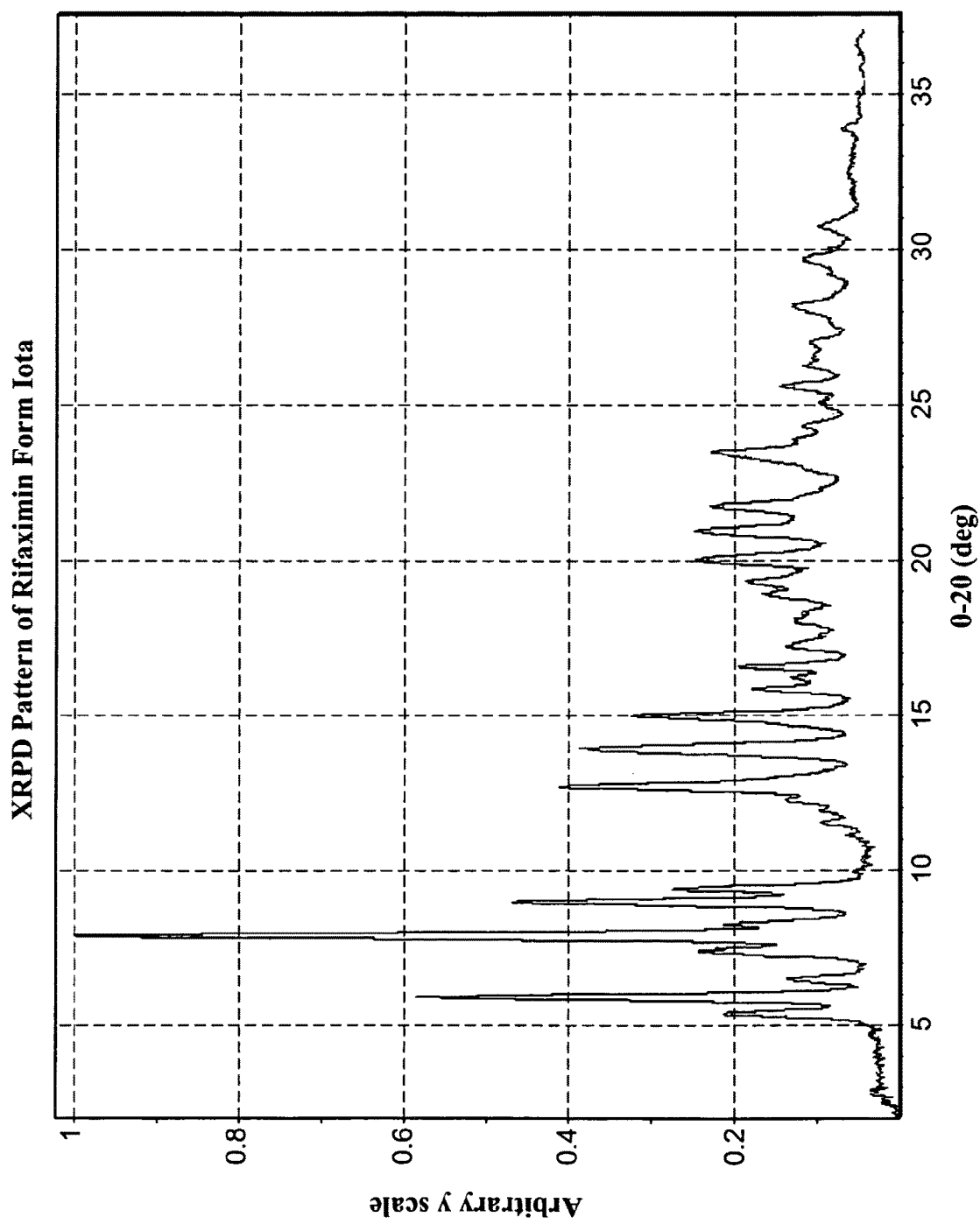
FIG. 46 depicts an exemplary XRPD pattern of rifaximin Form Iota.
Figure 47:
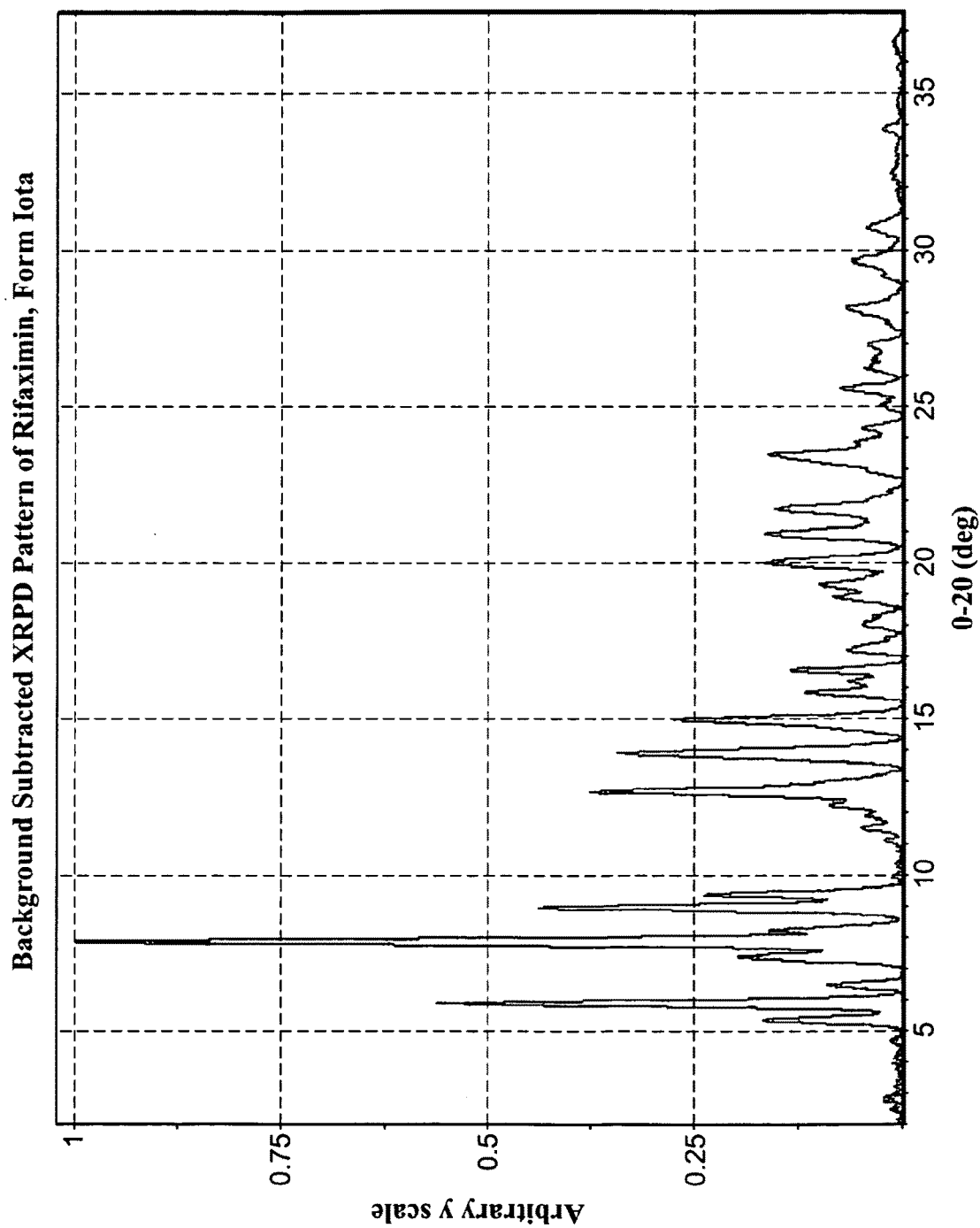
FIG. 47 depicts an exemplary background subtracted XRPD pattern of rifaximin, Form Iota.
Figure 48:
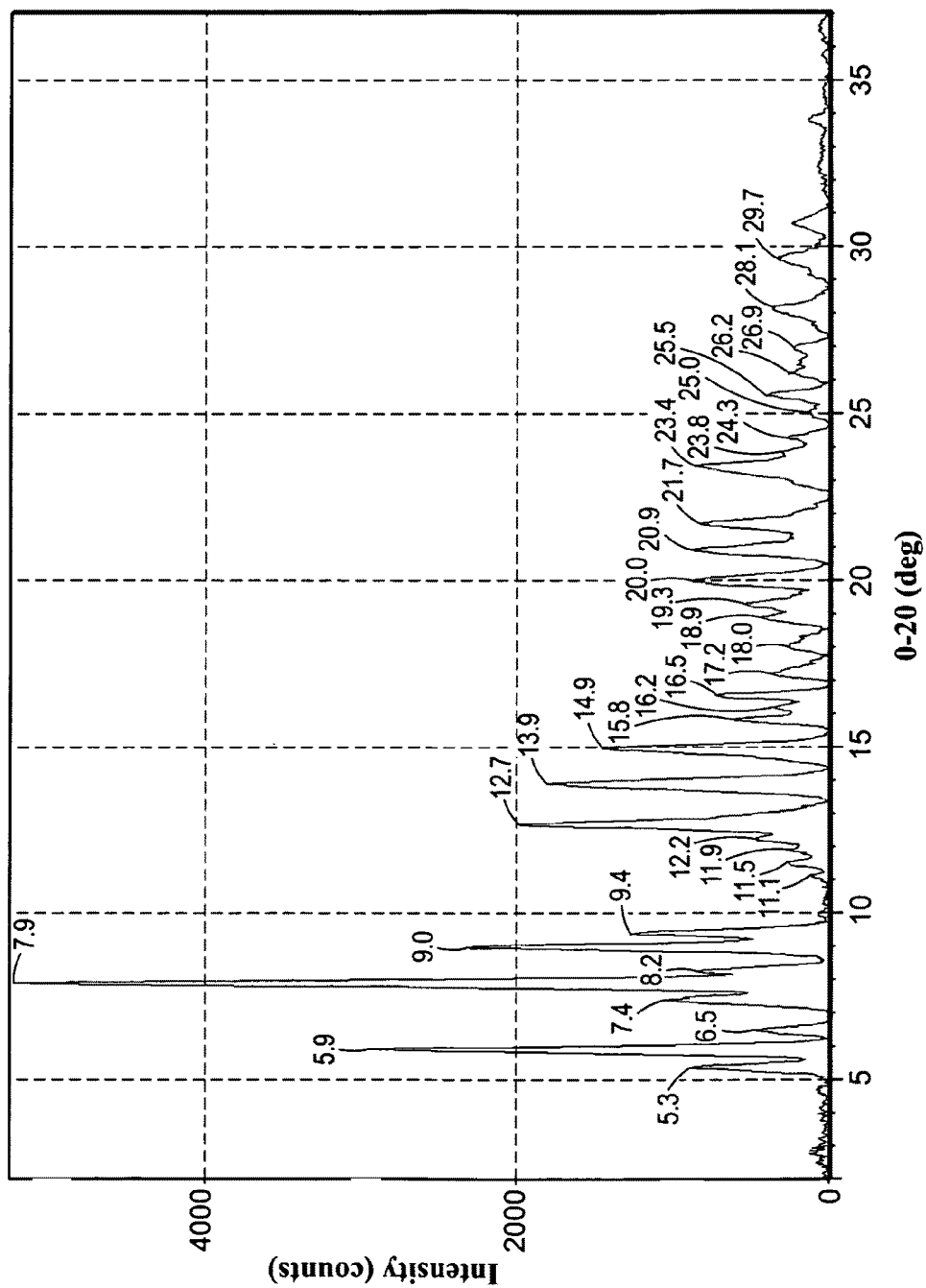
FIG. 48 depicts list of observed peaks for rifaximin, Form Iota. Note that the peak labels are meant as a visual aid. Consult FIG. 49 for accurate 2θ positions.

In one embodiment, Form Iota of rifaximin comprises an XRPD pattern substantially similar to FIG. 46.

In one embodiment, Form Iota of rifaximin exhibits an X-ray powder diffraction pattern comprising peaks expressed in degrees 2θ at two or more of about 5.9, about 7.9, and about 9.0; or about 12.7, about 13.9, and about 14.9; or about 5.9, about 7.9, and about 12.7; or about 5.9, about 9.0, and about 12.7; or about 5.9, about 13.9, and about 14.9±0.1; or about 5.9, about 7.9, and about 14.9; or about 9.0, about 12.7, and about 14.9; or about 5.9, about 7.9, about 9.0, and about 14.9; or about 5.9, about 7.9, about 9.0, and about 12.7; or about 5.9, about 7.9, about 9.0, about 12.7, about 13.9, and about 14.9.

In one embodiment, Form Iota of rifaximin exhibits an X-ray powder diffraction pattern comprising peaks expressed in degrees 2θ at two or more of about 5.9, about 7.4, about 7.9, and about 9.4.

In one embodiment, Form Iota of rifaximin exhibits an X-ray powder diffraction pattern comprising peaks expressed in degrees 2θ at two or more of about 7.4, about 20.0, and about 20.9.

In one embodiment, Form Iota of rifaximin exhibits an X-ray powder diffraction pattern comprising peaks expressed in degrees 2θ at two or more of about 5.9, about 13.9, and about 14.9.

In one embodiment, Form Iota of rifaximin exhibits an X-ray powder diffraction pattern comprising peaks expressed in degrees 2θ at two or more of about 20.0, about 20.9, and about 23.4.

In one embodiment, Form Iota of rifaximin exhibits an X-ray powder diffraction pattern comprising peaks expressed in degrees 2θ at two or more of about 5.9, about 13.9, about 14.9, about 20.0, and about 20.9.

In one embodiment, Form Iota of rifaximin exhibits an X-ray powder diffraction pattern comprising peaks expressed in degrees 2θ at two or more of about 7.4, about 12.7, about 13.9, and about 23.4.

In one embodiment, Form Iota of rifaximin exhibits an X-ray powder diffraction pattern comprising peaks expressed in degrees 2θ at two or more of about 5.9, about 7.4, about 7.9, about 12.7, about 13.9, about 14.9, about 20.0, about 20.9, and about 23.4.

In one embodiment, Form Iota of rifaximin exhibits an X-ray powder diffraction pattern comprising peaks expressed in degrees 2θ at two or more of about 5.9, about 7.4, about 7.9, about 9.0, about 9.4, about 12.7, about 13.9, about 14.9, about 20.0, about 20.9, and about 23.4.

In one embodiment, Form Iota of rifaximin exhibits an X-ray powder diffraction pattern comprising peaks expressed in degrees 2θ at two or more of about 5.9, about 13.9, about 14.9, about 20.0, and about 20.9; or about 5.9, about 13.9, and about 14.9; or about 7.4, about 12.7, about 13.9, and about 23.4; or about 20.0, about 20.9, and about 23.4; or about 5.9, about 7.4, about 7.9, about 12.7, about 13.9, about 14.9, about 20.0, about 20.9, and about 23.4; or about 5.9, about 7.4, about 7.9, and about 9.4; or about 7.4, about 20.0, and about 20.9; or about 5.9, about 7.4, about 7.9, about 9.0, about 9.4, about 12.7, about 13.9, about 14.9, about 20.0, about 20.9, and about 23.4.

In one embodiment, Form Iota exhibits an X-ray powder diffraction pattern comprising peaks expressed in degrees 2θ at two or more of about 5.9, about 7.9, about 9.0, about 12.7, about 13.9, and about 14.9.

In one embodiment, Form Iota of rifaximin exhibits an X-ray powder diffraction pattern comprising peaks expressed in degrees 2θ at two or more of about 5.9, about 7.9, and about 9.0.

In one embodiment, Form Iota of rifaximin exhibits an X-ray powder diffraction pattern comprising peaks expressed in degrees 2θ at two or more of about 12.7, about 13.9, and about 14.9.

In one embodiment, Form Iota of rifaximin exhibits an X-ray powder diffraction pattern comprising peaks expressed in degrees 2θ at two or more of about 5.9, about 7.9, and about 12.7.

In one embodiment, Form Iota of rifaximin exhibits an X-ray powder diffraction pattern comprising peaks expressed in degrees 2θ at two or more of about 5.9, about 9.0, and about 12.7.

In one embodiment, Form Iota of rifaximin exhibits an X-ray powder diffraction pattern comprising peaks expressed in degrees 2θ at about 5.9, about 13.9, and about 14.9.

In one embodiment, Form Iota of rifaximin exhibits an X-ray powder diffraction pattern comprising peaks expressed in degrees 2θ at two or more of about 5.9, about 7.9, and about 14.9.

In one embodiment, Form Iota of rifaximin exhibits an X-ray powder diffraction pattern comprising peaks expressed in degrees 2θ at about 9.0, about 12.7, and about 14.9.

In one embodiment, Form Iota of rifaximin exhibits an X-ray powder diffraction pattern comprising peaks expressed in degrees 2θ at two or more of about 5.9, about 7.9, about 9.0, and about 14.9.

In one embodiment, Form Iota of rifaximin exhibits an X-ray powder diffraction pattern comprising peaks expressed in degrees 2θ at two or more of about 5.9, about 7.9, about 9.0, and about 12.7.

Figure 50:
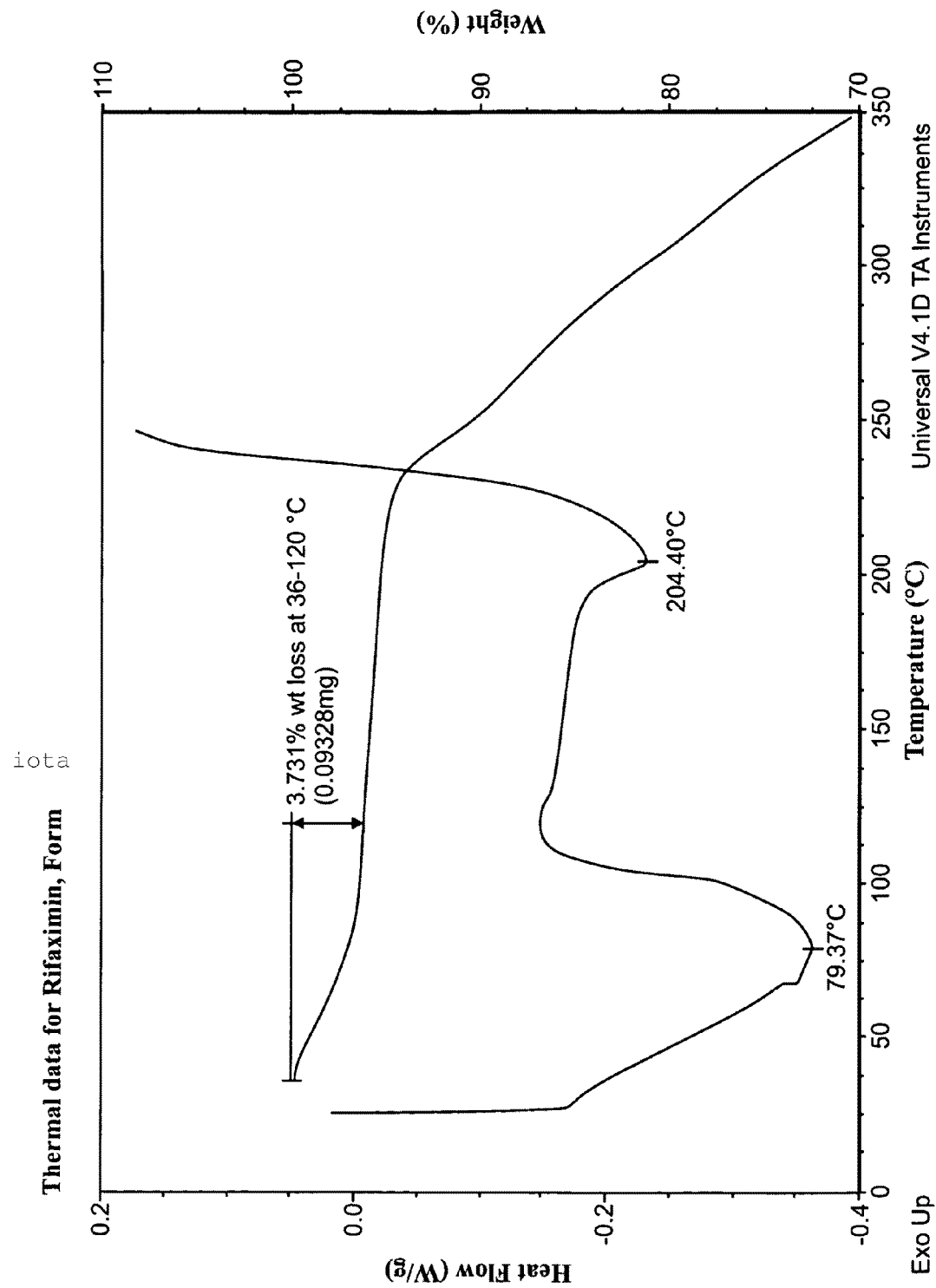
FIG. 50 depicts exemplary results of DSC and TGA thermograms for rifaximin, Form Iota.
Figure 52:
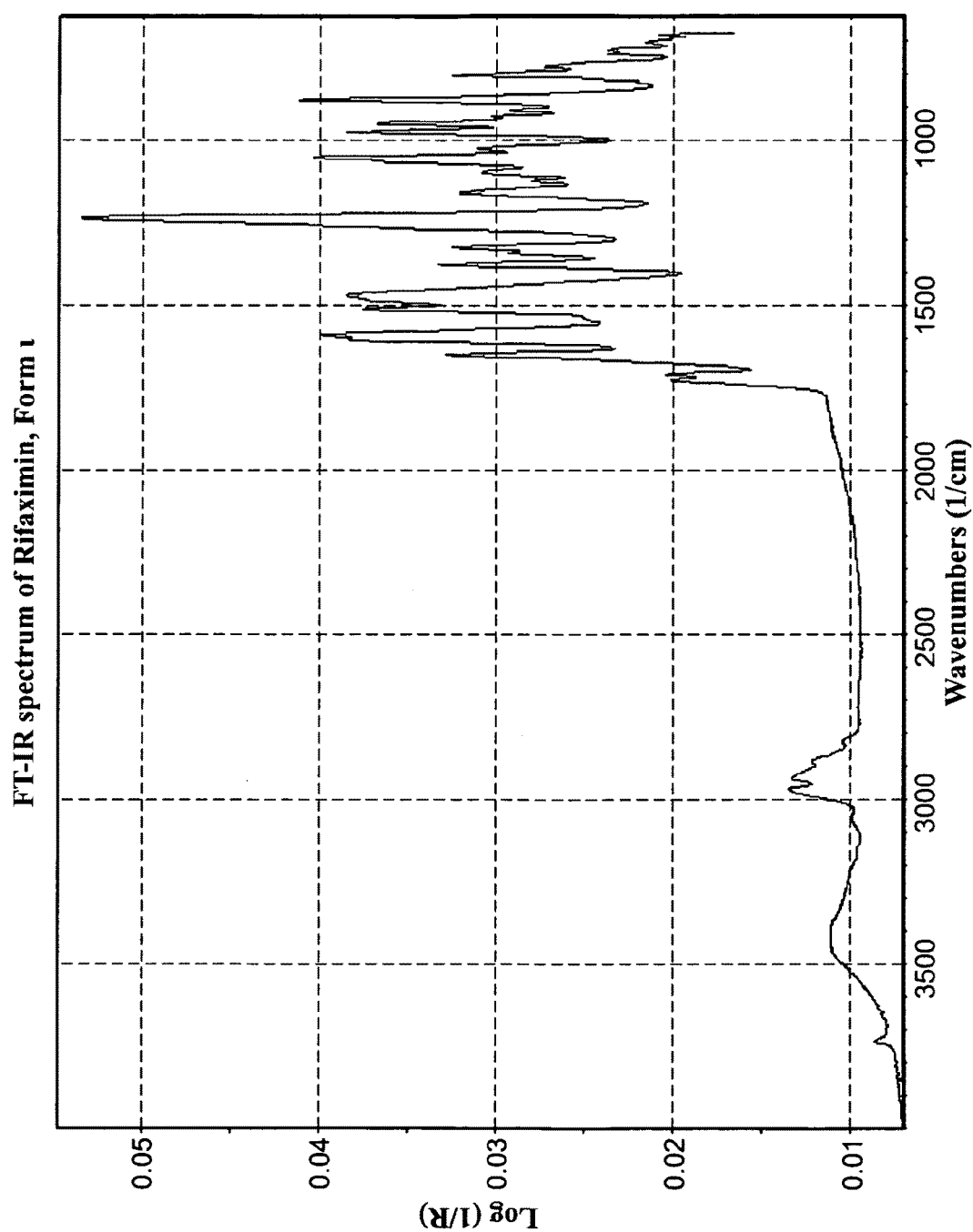
FIG. 52 depicts a FT-IR spectrum of rifaximin, Form Iota.

In one embodiment, Form Iota of rifaximin comprises DSC and TGA thermograms substantially similar to FIG. 50.

Figure 53:
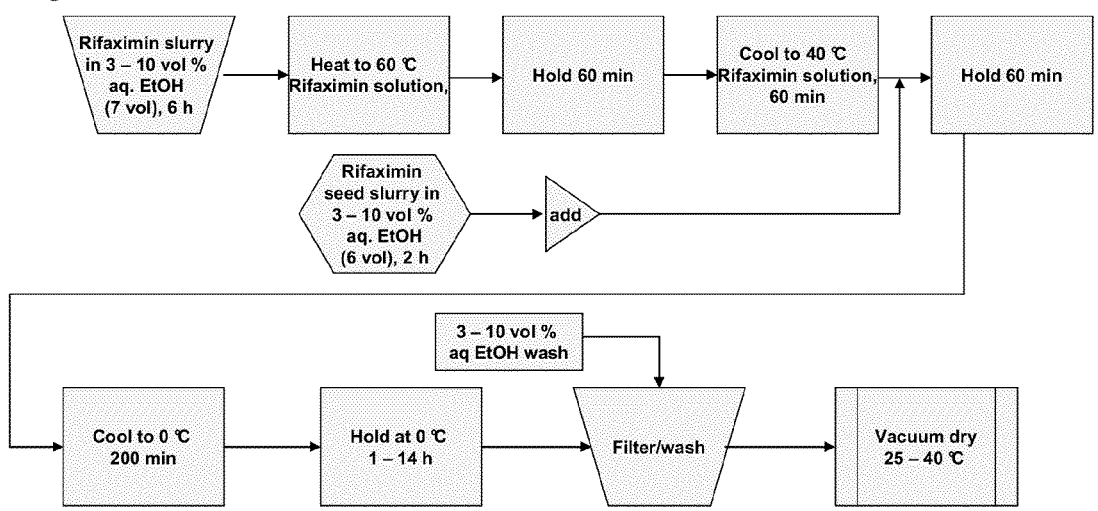
FIG. 53 shows an exemplary process for preparing rifaximin Forms Iota and Eta.

In one embodiment, Form Iota of rifaximin comprises solution proton NMR spectrum substantially similar to FIG. 53.

In one embodiment, provided herein are mixtures of the disclosed polymorphic forms of rifaximin. For example, provided herein is Form Xi, which is a mixture of Form Omicron and Form Pi.

In one embodiment, the Form mu, Form pi, Form Omicron, Form Xi, Form zeta, Form eta, Form iota, or salt form of rifaximin contain less than 5% by weight total impurities.

In one embodiment, the Form Mu, Form Pi, Form Omicron, Form Xi, Form Zeta, Form Eta, Form Iota, or salt form of rifaximin are at least 50% pure, or at least 75% pure, or at least 80% pure, or at least 90% pure, or at least 95% pure, or at least 98% pure.

In one embodiment, the pharmaceutical composition comprises one or more of Form Mu, Form Pi, Form Omicron, Form Xi, Form Zeta, Form Eta, Form Iota, or salt form of rifaximin and a pharmaceutically acceptable carrier.

In one embodiment, the composition further comprises one or more pharmaceutically acceptable excipients. The excipients may be one or more of a diluting agent, binding agent, lubricating agent, disintegrating agent, coloring agent, flavoring agent or sweetening agent.

In one embodiment, the pharmaceutical composition may be formulated as coated or uncoated tablets, hard or soft gelatin capsules, sugar-coated pills, lozenges, wafer sheets, pellets or powders in a sealed packet. In a related embodiment, the pharmaceutical composition may also be formulated for topical use.

In one embodiment, provided herein are methods of treating, preventing or alleviating a bowel related disorder comprising administering to a subject in need thereof an effective amount of one or more of Form Mu, Form Pi, Form Omicron, Form Xi, Form Zeta, Form Eta, Form Iota, or salt form of rifaximin.

In one embodiment, provided herein are methods for treating irritable bowel syndrome in a subject. Irritable bowel syndrome (IBS) is a disorder that affects the motility (muscle contractions) of the colon. Sometimes called "spastic colon" or "nervous colitis," IBS is not characterized by intestinal inflammation. IBS is a functional bowel disorder characterized by chronic abdominal pain, discomfort, bloating, and alteration of bowel habits. IBS may begin after an infection (post-infectious, IBS-PI) or without any other medical indicators.

In one embodiment, the subject is suffering from at least one bowel related disorder. Bowel related disorders include, for example, one or more of irritable bowel syndrome (IBS), diarrhea, microbe associated diarrhea, infectious diarrhea, *Clostridium, Clostridium difficile* disease, travelers' diarrhea, small intestinal bacterial overgrowth (SIBO), Crohn's disease, diverticular disease, pancreatitis (including chronic), pancreatic insufficiency, enteritis, colitis (including, ulcerative colitis), antibiotic associated colitis, hepatic encephalopathy (or other diseases which lead to increased ammonia levels), gastric dyspepsia, cirrhosis, polycystic liver disease, pouchitis, peritonitis, inflammatory bowel disease, *H. pylori* infection.

In one embodiment, the subject is suffering from at least one bowel related disorder selected from the group consisting of irritable bowel syndrome, travelers' diarrhea, small intestinal bacterial overgrowth, Crohn's disease, chronic pancreatitis, pancreatic insufficiency, enteritis and colitis.

The length of treatment for a particular bowel disorder will depend in part on the disorder. For example, travelers' diarrhea may only require treatment duration of from about 12 to about 72 hours, while Crohn's disease may require treatment durations from about 2 days to 3 months. Dosages of rifaximin will also vary depending on the diseases state.

The identification of those subjects who are in need of prophylactic treatment for bowel disorder is well within the ability and knowledge of one skilled in the art. Certain of the methods for identification of subjects which are at risk of developing a bowel disorder which can be treated by the subject method are appreciated in the medical arts, such as family history, travel history and expected travel plans, the presence of risk factors associated with the development of that disease state in the subject. A clinician skilled in the art can readily identify such candidate subjects, by the use of, for example, clinical tests, physical examination and medical/family/travel history.

In one embodiment, provided herein are methods of treating, preventing, or alleviating bowel related disorders in a subject suffering from hepatic insufficiency. Such methods include administering to a subject in need thereof an effective amount of one or more of Form Mu, Form Pi, Form Omicron, Form Xi, Form Zeta, Form Eta, Form Iota, or salt form, or a pharmaceutically acceptable salt, solvate or hydrate thereof. A subject "suffering from hepatic insufficiency" as used herein includes subjects diagnosed with a clinical decrease in liver function, for example, due to hepatic encephalopathy, hepatitis, or cirrhosis. Hepatic insufficiency can be quantified using any of a number of scales including a model end stage liver disease (MELD) score, a Child-Pugh score, or a Conn score.

In one embodiment, provided herein are methods for treating or preventing traveler's diarrhea in a subject. Traveler's diarrhea refers to gastrointestinal illness common amongst travelers. According to the CDC, travelers' diarrhea (TD) is the most common illness affecting travelers. Each year between 20%-50% of international travelers, an estimated 10 million persons, develop diarrhea. The onset of travelers' diarrhea usually occurs within the first week of travel but may occur at any time while traveling, and even after returning home. Risk is often dependent on destination though other risk factors are possible. For examples of the use of rifaximin to treat Travelers' diarrhea, see Infante R M, et al. Clinical Gastroenterology and Hepatology. 2004, 2:135-138 and Steffen R, M. D. et al. The American Journal of Gastroenterology. May 2003, Volume 98, Number 5, each of which is incorporated herein by reference in its entirety.

The illness usually results in increased frequency, volume, and weight of stool. Altered stool consistency also is common. A traveler may experience, for example, four to five loose or watery bowel movements each day. Other commonly associated symptoms are nausea, vomiting, diarrhea, abdominal cramping, bloating, fever, urgency, and malaise. Most cases are benign and resolve in 1-2 days without treatment, and TD is rarely life-threatening. The natural history of TD is that 90% of cases resolve within 1 week, and 98% resolve within 1 month.

Infectious agents are the primary cause of TD. The majority of cases are caused by bacterial, viral or protozoan infection. Bacterial enteropathogens cause approximately 80% of TD cases. The most common causative agent isolated in countries surveyed has been enterotoxigenic *Escherichia coli* (ETEC). ETEC produce watery diarrhea with associated cramps and low-grade or no fever. Besides ETEC and other bacterial pathogens, a variety of viral and parasitic enteric pathogens also are potential causative agents. In some embodiments, the traveler's diarrhea is caused by exposure to *E. Coli*.

In some embodiments, provided herein are methods for treating or preventing hepatic encephalopathy in a subject. Hepatic encephalopathy (portal-systemic encephalopathy, liver encephalopathy, hepatic coma) is a deterioration of brain function that occurs because toxic substances normally removed by the liver build up in the blood and reach the brain. Substances absorbed into the bloodstream from the intestine pass through the liver, where toxins are normally removed. In hepatic encephalopathy, toxins are not removed because liver function is impaired. Once in brain tissue, the compounds produce alterations of neurotransmission that affect consciousness and behavior. There are 4 progressive stages of impairment associated with HE that are defined by using the West Haven criteria (or Conn score) which range from Stage 0 (lack of detectable changes in personality) to Stage 4 (coma, decerebrate posturing, dilated pupils). In the earliest stages, the person's mood may change, judgment may be impaired, and normal sleep patterns may be disturbed. As the disorder progresses, the person usually becomes drowsy and confused, and movements become sluggish. Symptoms of hepatic encephalopathy can include impaired cognition, reduced alertness and confusion, a flapping tremor (asterixis), and a decreased level of consciousness including coma (e.g., hepatic coma), cerebral edema, and, possibly, death. Hepatic encephalopathy is commonly called hepatic coma or portal-systemic encephalopathy in the literature.

In one embodiment, provided herein are methods for alleviating the symptoms of bloating, gas or flatulence in a subject. In another embodiment the symptoms of bloating, gas or flatulence are caused by bacterial exposure. In other embodiments, the symptoms of bloating, gas or flatulence are not caused by bacterial exposure.

In some embodiments, provided herein are methods of treating or preventing a pathology in a subject suspected of being exposed to a biological warfare agent.

A method of assessing the efficacy of the treatment in a subject includes determining the pre-treatment level of intestinal bacterial overgrowth by methods well known in the art (e.g., hydrogen breath testing, biopsy, sampling of the intestinal bacteria, etc.) and then administering a therapeutically effective amount of a rifaximin polymorph to the subject. After an appropriate period of time (e.g., after an initial period of treatment) from the administration of the compound, e.g., about 2 hours, about 4 hours, about 8 hours, about 12 hours, or about 72 hours, the level of bacterial overgrowth is determined again. The modulation of the bacterial level indicates efficacy of the treatment. The level of bacterial overgrowth may be determined periodically throughout treatment. For example, the bacterial overgrowth may be checked every few hours, days or weeks to assess the further efficacy of the treatment. A decrease in bacterial overgrowth indicates that the treatment is efficacious. The method described may be used to screen or select subjects that may benefit from treatment with a rifaximin polymorph.

In yet another aspect, a method of treating a subject suffering from or susceptible to a bowel disorder comprises administering to a subject in need thereof a therapeutically effective amount of a rifaximin polymorph or co-crystal as described herein, to thereby treat the subject. Upon identification of a subject suffering from or susceptible to a bowel disorder, for example, IBS, one or more rifaximin polymorphs are administered.

Described herein are methods of using one or more of the Forms of rifaximin described herein to treat vaginal infections, ear infections, lung infections, periodontal conditions, rosacea, and other infections of the skin and/or other related conditions.

Provided herein are vaginal pharmaceutical compositions to treat vaginal infection, particularly bacterial vaginosis, to be administered topically, including vaginal foams and creams, containing a therapeutically effective amount of one for more polymorphic Forms of rifaximin described herein, such as between about 25 mg and about 2500 mg.

Pharmaceutical compositions known to those of skill in the art for the treatment of vaginal pathological conditions by the topical route may be advantageously used with one or more of the Forms of rifaximin described herein. For example, vaginal foams, ointments, creams, gels, ovules, capsules, tablets and effervescent tablets may be effectively used as pharmaceutical compositions containing one or more of the Forms of rifaximin described herein, which may be administered topically for the treatment of vaginal infections, including bacterial vaginosis.

Also provided herein are methods of using one for more polymorphic Forms of rifaximin described herein to treat gastric dyspepsia, including gastritis, gastroduodenitis, antral gastritis, antral erosions, erosive duodenitis and peptic ulcers. These conditions may be caused by the *Helicobacter pylori* microorganism. Pharmaceutical formulations known by those of skill in the art with the benefit of this disclosure to be used for oral administration of a drug may be used.

Provided herein are methods of treating ear infections with one for more polymorphic Forms of rifaximin described herein. Ear infections include external ear infection, or a middle and inner ear infection. Also provided herein are methods of using one for more polymorphic Forms of rifaximin described herein to treat or prevent aspiration pneumonia and/or sepsis, including the prevention of aspiration pneumonia and/or sepsis in patients undergoing acid suppression or undergoing artificial enteral feedings via a Gastrostomy/Jejunostomy or naso/oro gastric tubes; prevention of aspiration pneumonia in patients with impairment of mental status, for example, for any reason, for subjects undergoing anesthesia or mechanical ventilation that are at high risk for aspiration pneumonia. Provided herein are methods to treat or to prevent periodontal conditions, including plaque, tooth decay and gingivitis. Provided herein are methods of treating rosacea, which is a chronic skin condition involving inflammation of the cheeks, nose, chin, forehead, or eyelids.

In one aspect, methods of assessing the efficacy of treatment with a rifaximin polymorph in a subject comprise determining the pre-treatment level of bacterial overgrowth, administering a therapeutically effective amount of a rifaximin polymorph to the subject, and determining the bacterial overgrowth after an initial period of treatment with a rifaximin polymorph, wherein the modulation of the bacterial overgrowth indicates efficacy of an anti-bacterial treatment.

Efficacy of a treatment may be measured for example, as reduction of bacterial overgrowth. Efficacy may also be measured in terms of a reduction of symptoms associated with the bowel disorder, a stabilization of symptoms, or a cessation of symptoms associated with a bowel disorder, for example, a reduction of nausea, bloating, diarrhea, and the like.

In one aspect, methods of monitoring the progress of a subject being treated with one or more rifaximin polymorphs comprise: determining the pre-treatment level of bacterial overgrowth; administering a therapeutically effective amount of a rifaximin polymorph described herein to the subject; and determining the post-level of bacterial overgrowth after an initial period of treatment with one or more of the rifaximin polymorphs described herein.

In one embodiment, the modulation of the bacterial overgrowth indicates efficacy of an anti-bacterial treatment.

In another embodiment, a decrease in bacterial overgrowth indicates that the treatment is efficacious.

In another embodiment, the modulation of the bacterial overgrowth is an indication that the subject is likely to have a favorable clinical response to the treatment.

Provided herein is the use of one or more of the Forms of rifaximin described herein as a medicament.

Embodiments also provide pharmaceutical compositions, comprising an effective amount of a rifaximin polymorph (e.g., Form Mu, Form Pi, Form Omicron, Form Xi, Form Zeta, Form Eta, Form Iota, or salt form) described herein and a pharmaceutically acceptable carrier. In a further embodiment, the effective amount is effective to treat a bacterial infection, e.g., small intestinal bacterial overgrowth, Crohn's disease, hepatic encephalopathy, antibiotic associated colitis, and/or diverticular disease.

For examples of the use of rifaximin to treat Travelers' diarrhea, see Infante R M, Ericsson C D, Zhi-Dong J, Ke S, Steffen R, Riopel L, Sack D A, DuPont, H L. Enteroaggregative *Escherichia coli* Diarrhea in Travelers: Response to Rifaximin Therapy. *Clinical Gastroenterology and Hepatology.* 2004; 2:135-138; and Steffen R, M.D., Sack D A, M.D., Riopel L, Ph.D., Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. The American Journal of Gastroenterology. May 2003, Volume 98, Number 5, all of which are incorporated herein by reference in their entirety.

Embodiments also provide pharmaceutical compositions comprising one or more of a Form Mu, Form Pi, Form Omicron, Form Xi, Form Zeta, Form Eta, Form Iota, or salt form of rifaximin, and a pharmaceutically acceptable carrier. That is, formulations may contain only one polymorph or may contain a mixture of more than one polymorph. Mixtures may be selected, for example on the basis of desired amounts of systemic adsorption, dissolution profile, desired location in the digestive tract to be treated, and the like. Embodiments of the pharmaceutical composition further comprise excipients, for example, one or more of a diluting agent, binding agent, lubricating agent, disintegrating agent, coloring agent, flavoring agent or sweetening agent. One composition may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, the rifaximin polymorph is administered to the subject using a pharmaceutically-acceptable formulation, e.g., a pharmaceutically-acceptable formulation that provides sustained delivery of the rifaximin polymorph to a subject for at least about 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those rifaximin polymorphs, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is preferably "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifaximin forms as disclosed herein include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred %, this amount will range from about 1% to about ninety-nine % of active ingredient, from about 5% to about 70%, and from about 10% to about 30%.

Methods of preparing these compositions include the step of bringing into association a rifaximin polymorph(s) with the carrier and, optionally, one or more accessory ingredients. In general, the formulations are prepared by uniformly and intimately bringing into association a rifaximin polymorph with liquid carriers, or finely divided solid carriers, or both, and then, if necessary, shaping the product.

Compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifaximin polymorph(s) as an active ingredient. A compound may also be administered as a bolus, electuary or paste.

Form μ, Form π, Form o, Form Xi, Form ζ, Form η, Form ι, or salt forms can be advantageously used in the production of medicinal preparations having antibiotic activity, containing rifaximin, for both oral and topical use. The medicinal preparations for oral use will contain rifaximin Form Mu, Form Pi, Form Omicron, Form Xi, Form Zeta, Form Eta, Form Iota, or salt forms together with the usual excipients, for example diluting agents such as mannitol, lactose and sorbitol; binding agents such as starches, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; colouring, flavouring and sweetening agents.

In one embodiment, the composition is formulated for selected coated and uncoated tablets, hard and soft gelatine capsules, sugar-coated pills, lozenges, wafer sheets, pellets and powders in sealed packets.

Embodiments of the disclosure include solid preparations administrable by the oral route, for instance coated and uncoated tablets, of soft and hard gelatin capsules, sugar-coated pills, lozenges, wafer sheets, pellets and powders in sealed packets or other containers.

Medicinal preparations for topical use can contain rifaximin Form Mu, Form Pi, Form Omicron, Form Xi, Form Zeta, Form Eta, Form Iota, or salt form together with excipients, such as white petrolatum, white wax, lanoline and derivatives thereof, stearylic alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxymethyl propylcellulose, sodium carboxymethylcellulose, colloidal aluminium and magnesium silicate, sodium alginate.

Embodiments of the disclosure relate to all of the topical preparations, for instance ointments, pomades, creams, gels and lotions.

In one embodiment, the compositions described herein are formulated for topical use.

In solid dosage forms of rifaximin for oral administration (capsules, tablets, pills, dragees, powders, granules and the like), the active ingredient is typically mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) colouring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the rifaximin polymorph(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active rifaximin polymorph(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions for rectal or vaginal administration may be presented as a suppository, which may be prepared by mixing one or more rifaximin polymorph(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams or spray formulations containing such carriers as are known in the art to be appropriate.

Dosage forms for the topical or transdermal administration of a rifaximin polymorph(s) include powders, sprays, ointments, pastes, creams, lotions, gels, solutions, patches and inhalants. The active rifaximin polymorph(s) may be mixed under sterile conditions with a pharmaceutically-acceptable carrier, and with any preservatives, buffers, or propellants which may be required.

Ointments, pastes, creams and gels may contain, in addition to rifaximin polymorph(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a rifaximin polymorph(s), excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

The rifaximin polymorph(s) can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

An aqueous aerosol is made, for example, by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a rifaximin polymorph(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions suitable for parenteral administration may comprise one or more rifaximin polymorph(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to alter the absorption of the drug. This may be accomplished by the use of a liquid suspension of crystalline or salt material having poor water solubility. The rate of absorption of the drug may then depend on its rate of dissolution which, in turn, may depend on crystal size and crystalline form. Alternatively, delayed absorption of a drug form is accomplished by dissolving or suspending the drug in an oil vehicle.

Injectable depot forms are made by forming microencapsule matrices of rifaximin polymorph(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the rifaximin polymorph(s) are administered as pharmaceuticals, to humans and animals, they can be given per se or as a pharmaceutical composition containing, for example, from about 0.1 to about 99.5% (for example, from about 0.5 to about 90%) of active ingredient in combination with a pharmaceutically-acceptable carrier.

Regardless of the route of administration selected, the rifaximin polymorph(s), which may be used in a suitable hydrated form, and/or the pharmaceutical compositions can be formulated into pharmaceutically-acceptable dosage forms by methods known to those of skill in the art.

Actual dosage levels and time course of administration of the active ingredients in the pharmaceutical compositions may be varied so as to obtain an amount of the active ingredient which is effective to achieve the desired therapeutic response for a particular subject, composition, and mode of administration, without being toxic to the subject. An exemplary dose range is from about 25 to about 3000 mg per day.

In one embodiment, the dose of rifaximin polymorph is the maximum that a subject can tolerate without developing serious side effects. In one embodiment, the rifaximin polymorph is administered at a concentration of about 1 mg to about 200 mg per kilogram of body weight, about 10-about 100 mg/kg or about 40 mg-about 80 mg/kg of body weight. Ranges intermediate to the above-recited values are also intended to be part.

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound of this invention is less than its effective amount in case the other therapeutic agent is not administered. In another embodiment, the effective amount of the conventional agent is less than its effective amount in case the compound of this invention is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than about 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same subject's visit.

In certain embodiments, one or more compounds and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds may be repeated and the administrations may be separated by at least about 1 day, 2 days, 3 days, 5 days, 10 days, 15 days, 30 days, 45 days, 2 months, 75 days, 3 months, or at least about 6 months. In other embodiments, the administration of the same therapy (e.g., prophylactic or therapeutic agent) other than a rifaximin polymorph may be repeated and the administration may be separated by at least about 1 day, 2 days, 3 days, 5 days, 10 days, 15 days, 30 days, 45 days, 2 months, 75 days, 3 months, or at least about 6 months.

Certain indications may require longer treatment times. For example, travelers' diarrhea treatment may only last from between about 12 hours to about 72 hours, while a treatment for Crohn's disease may be from between about 1 day to about 3 months. A treatment for hepatic encephalopathy may be, for example, for the remainder of the subject's life span. A treatment for IBS may be intermittent for weeks or months at a time or for the remainder of the subject's life.

Another embodiment includes articles of manufacture that comprise, for example, a container holding a pharmaceutical composition suitable for oral or topical administration of rifaximin in combination with printed labeling instructions providing a discussion of when a particular dosage form can be administered with food and when it should be taken on an empty stomach. Exemplary dosage forms and administration protocols are described infra. The composition will be contained in any suitable container capable of holding and dispensing the dosage form and which will not significantly interact with the composition and will further be in physical relation with the appropriate labeling. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect is an article of manufacture that comprises a container containing a pharmaceutical composition comprising rifaximin wherein the container holds preferably rifaximin composition in unit dosage form and is associated with printed labeling instructions advising of the differing absorption when the pharmaceutical composition is taken with and without food.

Packaged compositions are also provided, and may comprise a therapeutically effective amount of rifaximin. Rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

Kits are also provided herein, for example, kits for treating a bowel disorder in a subject. The kits may contain, for example, one or more of Form Mu, Form Pi, Form Omicron, Form Xi, Form Zeta, Form Eta, Form Iota, or salt Form of rifaximin and instructions for use. The instructions for use may contain proscribing information, dosage information, storage information, and the like.

Packaged compositions are also provided, and may comprise a therapeutically effective amount of one or more of a polymorph of rifaximin as described herein and a pharmaceutically acceptable carrier or diluent, wherein the composition is formulated for treating a subject suffering from or susceptible to a bowel disorder, and packaged with instructions to treat a subject suffering from or susceptible to a bowel disorder.

Exemplary methods of producing polymorphic forms of rifaximin are set forth below.

Embodiments are also directed to processes for producing one or more of Form Mu, Form Pi, Form Omicron, Form Xi, Form Zeta, Form Eta, Form Iota, or salt Form of rifaximin. Methods are outlined in the Examples and in the Tables infra.

In some embodiments, the rifaximin Forms are dried by air-drying at ambient conditions. In some embodiments, the rifaximin Forms are dried with a nitrogen bleed. In some embodiments, the rifaximin Forms are dried by vacuum drying at temperatures ranging from ambient temperature (about 25° C.) to about 60° C. In some embodiments, the rifaximin Forms are dried with agitation.

In some embodiments, the rifaximin Forms are obtained by drying the rifaximin with ethanol under various drying conditions described herein. In some embodiments, the rifaximin Forms are obtained by recrystallization from ethanol followed by one or more of the various drying conditions described herein.

In some embodiments, the water content of the ethanol described in the processes herein is less than about 10% (w/w), such as, less than about 5% (w/w), less than about 2% (w/w), and less than about 1% (w/w). In some embodiments, the ethanol is absolute.

In some embodiments, the method or process described herein include stirring at ambient temperatures.

In some embodiments, the method or process described herein include collecting solids by filtration.

In some embodiments, the method or process described herein include drying the collected solids.

Other embodiments and aspects are disclosed infra.

Rifaximin Form π can be prepared by drying absolute ethanol-damp Rifaximin Form Omicron, or by a mixture of Form Omicron and Form Zeta.

Rifaximin Form Omicron can be prepared by slurrying Form Eta or Form Gamma in ethanol to generate a slurry, which may be shaken and subsequently filtered.

Rifaximin Form Eta and Iota can be prepared by the process according to FIG. 53. For example, provided herein is a least one method of preparing From Eta, comprising:

dissolving a Form of rifaximin to form a first mixture;
cooling the first mixture to a seeding temperature;
adding a slurry of rifaximin Form Zeta to form a second mixture;
cooling the second mixture to sub-ambient temperature; and
filtering the second mixture to obtain Form Eta, which is optionally washed and dried.

In one aspect, the Form of rifaximin comprises a solid form. In another aspect, the Form of rifaximin is selected from Form Mu, Form Pi, Form alpha, Form beta, Form Xi, Form Nu, Form Theta, Form Gamma, Form Omicron, Form Zeta, or a salt, or mixtures thereof. In another aspect, the Form of rifaximin is Form Zeta.

In one aspect, the first mixture comprises ethanol. In another aspect, the water content of the first mixture is higher than approximately 3 wt %. In another aspect, the water content of the first mixture ranges from about 3 wt % to about 10 wt %.

Rifaximin Form μ can be prepared by fast evaporation from a 1:1 (v/v) ethanol/heptane solution at room temperature. In an exemplary embodiment, approximately 3 grams of as-received material can be dissolved in about 60 mL ethanol. The solution can then be diluted with equal volume of heptane and filtered into an open beaker or crystallization dish. The filtered solution can then be left at ambient conditions in a fume hood for fast evaporation.

Rifaximin Form Mu can also be generated through the hydration of rifaximin Form Theta (which, in turn, is generated through the desolvation of rifaximin Form Zeta).

Rifaximin Form Theta can convert to rifaximin Form μ upon exposure to 75% RH. Additionally, rifaximin Form μ can be generated at 51% RH. A slightly disordered Form μ (as a mixture with Form ι) can be generated at 44% RH. Rifaximin Form μ can irreversibly dehydrate to Form γ.

Rifaximin Form gamma can be prepared by slurrying rifaximin in a solvent, e.g. ethanol, in a suitable reactor or flask that is equipped with stirring, mechanical or magnetic, a thermometer and a reflux condenser. The suspension is heated to a temperature of between about 40° C. to about 80° C., e.g. between about 45° C. to about 70° C. or between about 55° C. to about 65° C., with stirring until complete dissolution of the solid. While maintaining this temperature, a second solvent, e.g. water, is added over a period of about 1 minute to about 120 minutes, e.g. about 10 minutes to about 60 minutes or about 20 minutes to about 40 minutes. At the end of the addition of the second solvent the temperature is brought to between about 10° C. to about −50° C., e.g. from about 20° C. to about 40° C. or from about 25° C. to about 35° C., over a period of time lasting between about 10 minutes to about 120 minutes, e.g. about 20 minutes to about 60 minutes or about 30 minutes to about 50 minutes, and is kept at this value until crystallization is observed. Subsequently, the temperature is lowered to between about −10° C. to about 10° C., e.g. between about −7° C. to about 7° C. or between about −5° C. to about 5° C., over a period of time lasting between about 0.5 hour to about 5 hours, e.g. about 1 hour to about 4 hours or about 1.5 hours to about 3 hours, and kept at this temperature for between about 1 hour to about 24 hours, e.g. about 2 hours to about 12 hours or about 4 hours to about 8 hours. The suspension is then filtered and the solid is washed with the second solvent, e.g. water. The filter cake is dried under vacuum at room temperature until a constant weight is observed.

Rifaximin Form Zeta can be prepared by suspending rifaximin in a mixture of solvents, e.g. ethanol and water, with a ratio of about 4:1, at temperatures ranging from about 15° C. to about 35° C., e.g. from about 20° C. to about 30° C. or from about 22° C. to about 27° C. for a period of time ranging from about 1 hour to about 10 hours, e.g. about 2 hours to about 8 hours or about 4 hours to about 6 hours. The solids can be isolated, e.g. via decantation or filtration, and the solids can be stored in a refrigerator.

In one embodiment, the process for producing Form ζ of rifaximin comprises forming an EtOH slurry of an initial Form α-dry of rifaximin at ambient temperature and crystallizing rifaximin from the slurry. In one embodiment, the method further comprises crash cooling the slurry prior to crystallization. In another embodiment, the EtOH slurry comprises an ethanol/water slurry in the ratio of from between 1 to 0.02-0.45.

Rifaximin Form Theta can be prepared by drying Form ζ under vacuum at ambient temperature for approximately 6 hours. Form Theta can be an ethanolate based on $^1$H-NMR results. In an exemplary embodiment, one sample can contain about two moles of ethanol per mole of rifaximin by $^1$H-NMR, but the volume estimated from the tentative XRPD indexing solution indicates the unit cell is able to accommodate up to about 4 moles of ethanol per mole of rifaximin. XRPD patterns of Form Theta were indexed successfully. Successful indexing of the powder diffraction pattern exhibited by this form provides supports an indication that Form Omicron is a single crystalline phase. Rifaximin Form Theta can be obtained at large scale by vacuum drying of Form Zeta. In an exemplary embodiment, about 58.96 g of rifaximin can be added to about 300 mL of ethanol with stirring at ambient conditions. The rifaximin can dissolve almost completely in the initial stirring and yield a very dark red solution. With continuous stirring, the solution can become lighter in color, and the turbidity can increase until an orange/red paste is formed. At that point, an aliquot of about 100 mL of ethanol can be added, producing a total volume of ethanol of about 400 mL. The slurry sample can then be vacuum filtered through a filter paper under nitrogen environment (21% RH, 22° C.) to produce a red-orange paste. Once the filtrate stops dripping from the end of funnel, the filter cake can be broken loose on the filter paper with a spatula while vacuum and nitrogen remain on. In the exemplary embodiment, the total drying time of the sample on filter paper is approximately 30 minutes. The resulting solid can be identified as Form Zeta by XRPD. This solid sample can later be dried under vacuum for approximately 6 hours at ambient temperature, and the post XRPD pattern can be used to confirm that the solid has been converted to Form Theta after vacuum drying.

Rifaximin Form iota, can be prepared by precipitating rifaximin from ethanol; drying the precipitated rifaximin under nitrogen; and maintaining the rifaximin at ambient temperature. In some embodiments, the rifaximin can be maintained under vacuum for about 6 or more hours. In some embodiments, the rifaximin can be maintained at between about 22% and 50% humidity. In some embodiments, the rifaximin is dried for about 10 minutes or less.

In one embodiment, methods for producing rifaximin Form Eta, comprise:
obtaining a rifaximin slurry in absolute ethanol;
heating the slurry to about 60° C. while stirring;
cooling the slurry to 40° C. while stirring;
adding a seed slurry of rifaximin to make a rifaximin mixture and stirring at 40° C.;
cooling the mixture to 0° C.;
holding the mixture at 0° C.;
vacuum filtering the mixture; and
vacuum oven drying,
thereby producing rifaximin Form Eta.

In a related embodiment, the stirring is at 300 RPM. In another related embodiment, the mixture is cooled to about 0° C. over a time of about 200 minutes. In another related embodiment, the mixture is held at about 0° C. for about 15 hours. In another related embodiment, the rifaximin seed mass is 1.5 weight % of the rifaximin slurry; the seed slurry concentration is 3 times lower than the rifaximin slurry; the seed slurry concentration of approximately 50 mg/ml; or rifaximin slurry has 20 times more ethanol than the rifaximin mass.

In yet another related embodiment, the vacuum oven drying is at about 40° C. for about 24 hours.

In yet another related embodiment, the seed slurry comprises a concentration of approximately 5 mg/ml rifaximin.

In one embodiment, processes for producing a mixture of polymorphs Zeta and gamma comprise humidifying Form Zeta.

In one embodiment, processes for producing Form 11 of rifaximin comprise drying Form Zeta.

Figure 11:
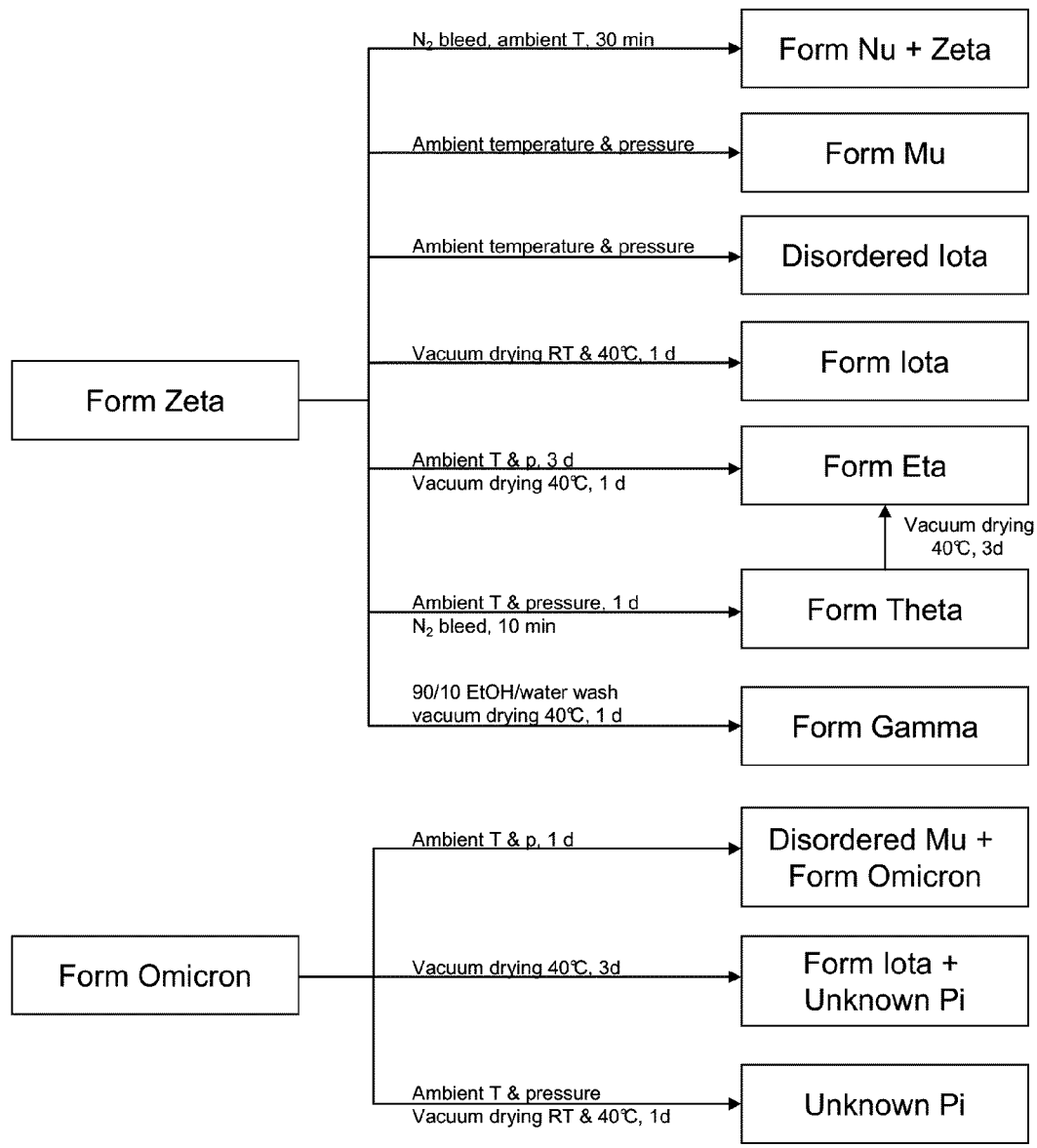
FIG. 11 is a schematic of how the different polymorphs of rifaximin, including Form Pi, can be formed.

In one embodiment, Form 11 and Iota are produced by the process disclosed in FIG. 11.

In one embodiment, processes of producing Zeta and mixtures of Zeta and Gamma comprise precipitating the initial rifaximin forms.

In one embodiment, processes of producing mixtures of Form Gamma, including but not limited to, Form Gamma and Form Eta mixtures and Form Gamma and Form Zeta mixtures comprise precipitating the initial forms.

In one embodiment, processes for producing rifaximin form Eta and mixtures of rifaximin forms η and γ comprise precipitating the initial rifaximin forms in the manner set forth in Table 22.

In one embodiment, processes for producing Form Eta, Form Zeta, Form Gamma, Form Xi and Form Gamma mixtures and Form Gamma and Form Eta mixtures of rifaximin comprise precipitating the initial forms in the manner set forth in Tables 24 and 25.

In one embodiment, processes for producing Form Iota comprise the conditions set forth in Table 28.

Some features of polymorph Form ζ include, for example: Form Zeta was observed by XRPD analysis of solids in solution (FIGS. 42 and 43). These solids were removed and stressed under various relative humidity (RH) conditions. XRPD analysis after three days showed conversion to Form γ under 43% RH, though form conversion was likely initiated upon removal of the solids from solution.

Some features of polymorph Form Eta include, for example:
Form η was generated by drying Form Zeta under vacuum for one day (FIG. 44). The material of Form Zeta (after formation) remained unchanged when dried under vacuum at 40° C. for one day.

Other exemplary protocols for making the disclosed polymorphic forms of rifaximin can be found in the Examples as well as in U.S. Pat. No. 7,045,620; U.S. Patent Publication No. 2009-0130201; U.S. Patent Publication No. 2011-0160449; U.S. Patent Publication No. 2010-0010028; U.S. Patent Publication No. 2011-0105550; and U.S. Patent Publication No. 2010-0174064, each of which is incorporated herein by reference in its entirety.

Further embodiments will now be described by the following non-limiting examples. It will be appreciated that the invention should not be construed to be limited to any of the foregoing examples, which are now described.

EXAMPLES

Materials

Samples were stored in a dessicator. Solvents and other reagents used were purchased from commercial suppliers and used as received. Solvents were either HPLC or ACS grade.

Example 1

Preparation of Form Xi

To prepare rifaximin Form Xi, 33.5 g rifaximin was first dried in vacuo at 40° C. for 16 hours and then dissolved in 150 mL absolute ethanol in a 500 mL jacketed reactor. With stirring, the mixture was heated 60° C., held for 15 minutes and then cooled at 0.4° C./min to 40° C. Precipitation was visually observed at 43° C. The sample was heated back up to 60° C. to dissolve the solid and then cooled at 0.4° C./min to 45° C. The solution was seeded with a slurry of (500 mg) Form η in 10 mL ethanol, that was pre-slurried for 4 hours. The mixture was heated at 45° C. for 1 hour, then cooled to 0° C. over 200 minutes. The slurry was held at 0° C. and continued stirring for 14 hours. The material was filtered, washed by 50 mL cold ethanol, and split equally into two lots. One lot was dried by rotary evaporation for 10 hours and the other lot was vacuum dried for 20 hours.

The material was analyzed by x-ray powder diffractometry (XRPD). In addition, the material was characterized by differential scanning calorimetry (DSC), thermogravimetric analysis (TGA), moisture sorption (also known as dynamic vapor sorption, DVS), Karl-Fischer titration (KF), solution proton ($^1$H) and solid-state (SS) nuclear magnetic resonance (NMR), and attenuated total reflectance infrared (ATR-IR) and Raman spectroscopy.

Figure 22:
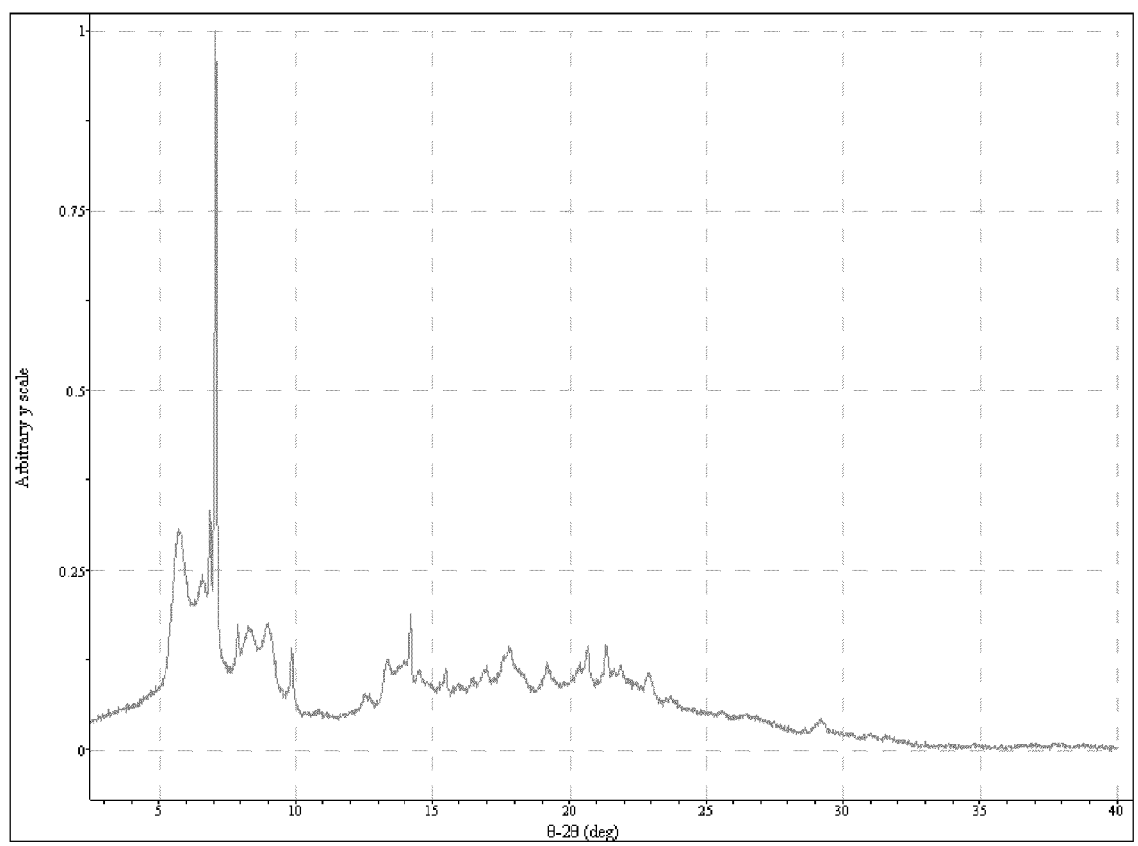
FIG. 22 shows a XRPD pattern of rifaximin Form Xi.
Figure 23:
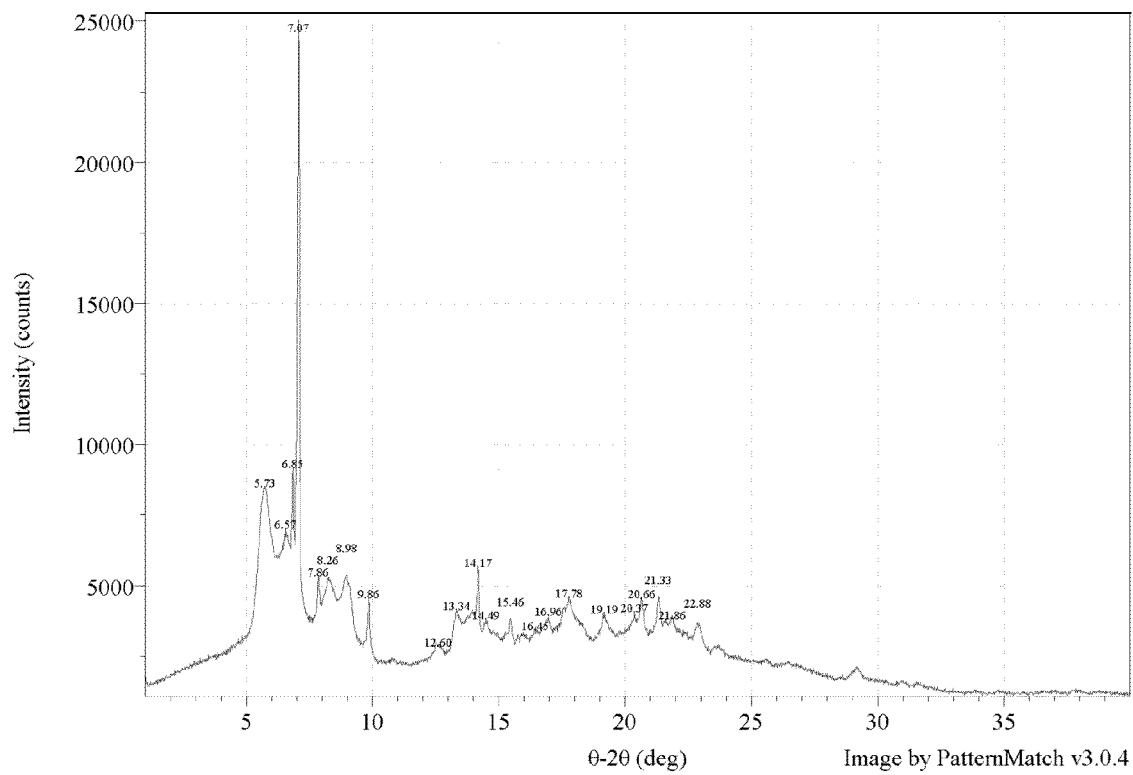
FIG. 23 shows a XRPD pattern of rifaximin Form Xi with Observed Peaks listed.
Figure 24:
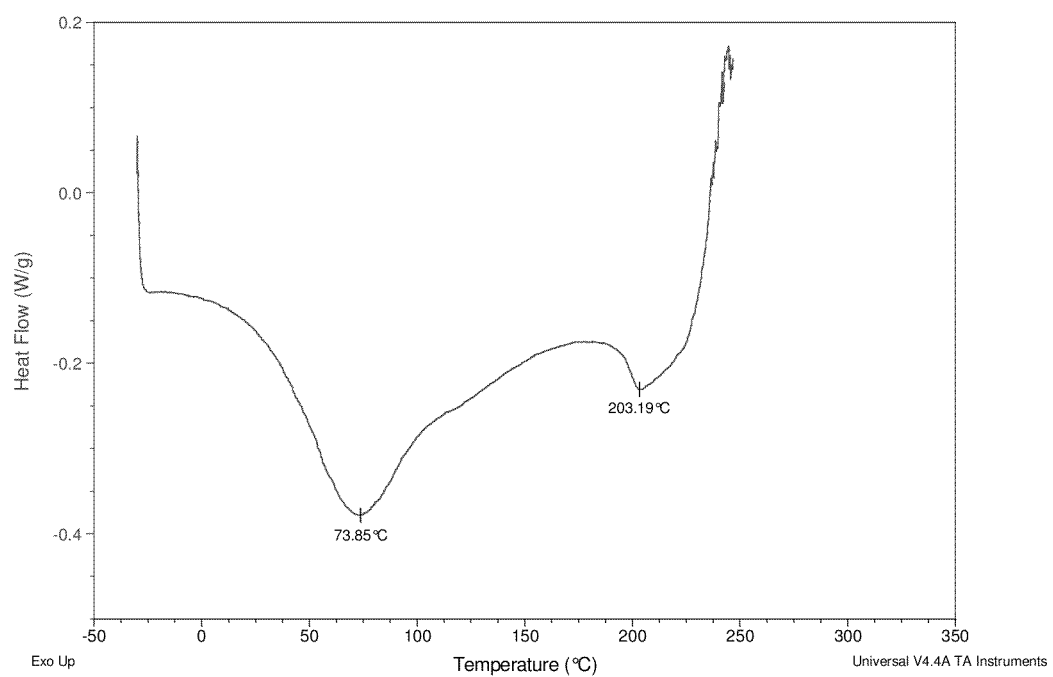
FIG. 24 shows a DSC thermogram of rifaximin Form Xi.
Figure 25:
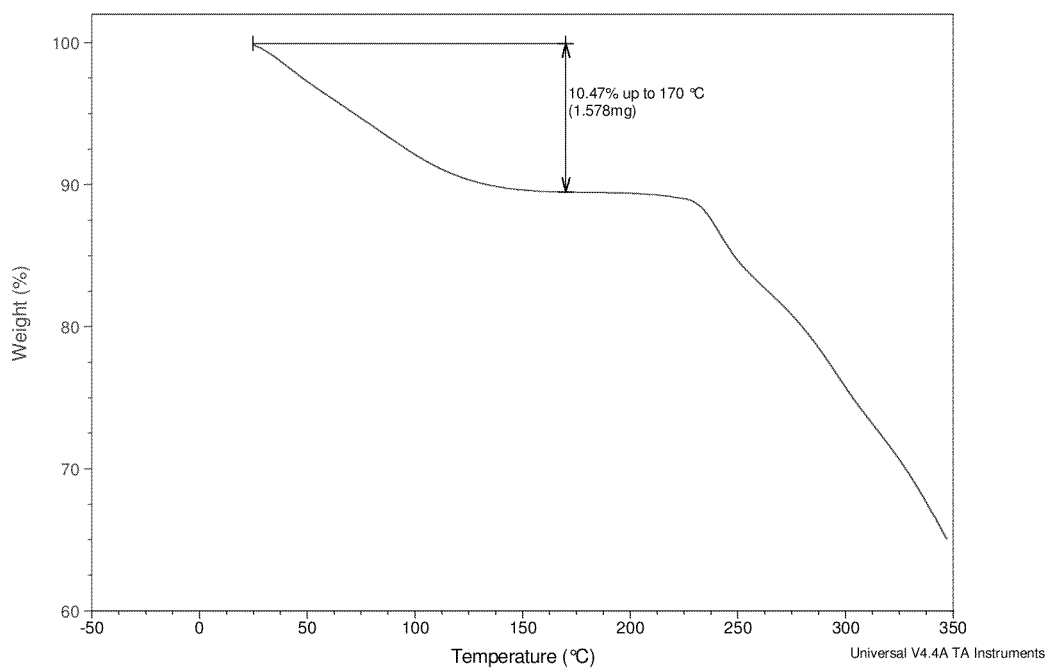
FIG. 25 shows a TGA thermogram of rifaximin Form Xi.

The XRPD pattern of Rifaximin Form Xi is shown in FIGS. 22 and 23 Observed and prominent peak lists are included.

One Panalytical pattern was analyzed. Observed peaks are shown in FIG. 23

Additional characterization data for rifaximin Form Xi by DSC, TGA, DVS and XRPD before and after DVS are presented in FIG. 24 through FIG. 27.

DSC results show two broad endotherms with signal maxima at approximately 73.9° C. and 203.2° C. TGA of the same sample indicates a weight loss of approximately 10.5% when heated up to 170° C. (FIG. 25. Thermal events above 230° C. are likely due to decomposition.

Rifaximin Form Xi contains 0.24 wt % of water by Karl-Fischer analysis. Solution $^1$H-NMR shows that the sample contains approximately 2.1 mole of ethanol per mole of rifaximin.

Figure 26:
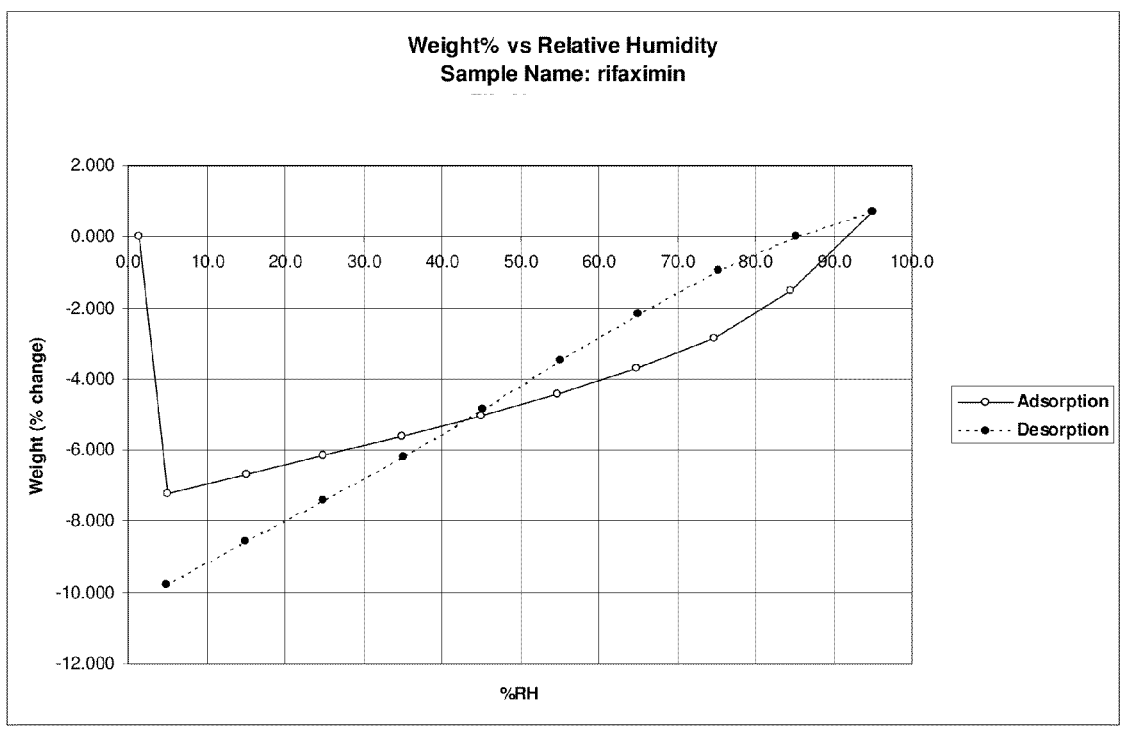
FIG. 26 shows moisture sorption (DVS) data of rifaximin Form Xi.
Figure 27:
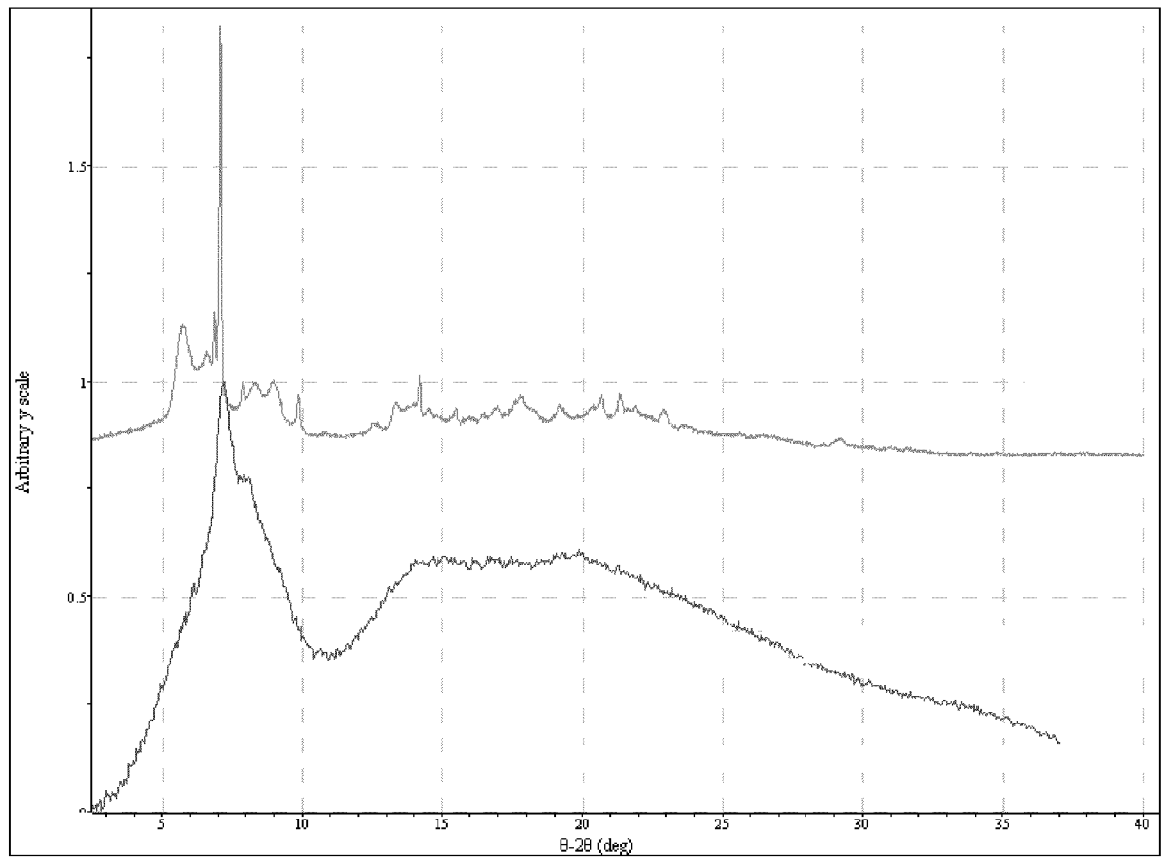
FIG. 27 shows a XRPD pattern of rifaximin Form Xi before and after the DVS experiment.
Figure 28:
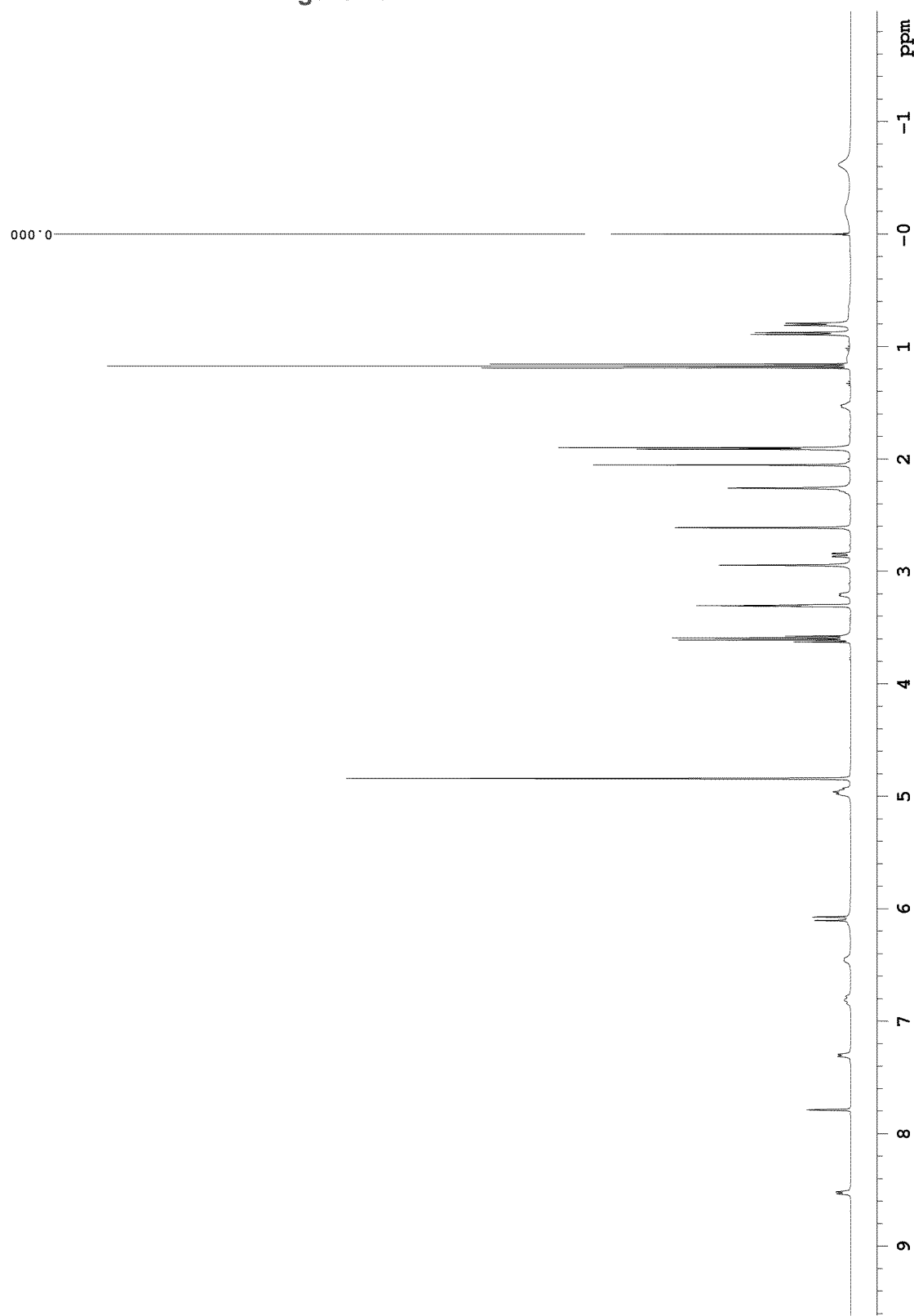
FIG. 28 shows a solution proton NMR spectrum of rifaximin Form Xi.
Figure 29:
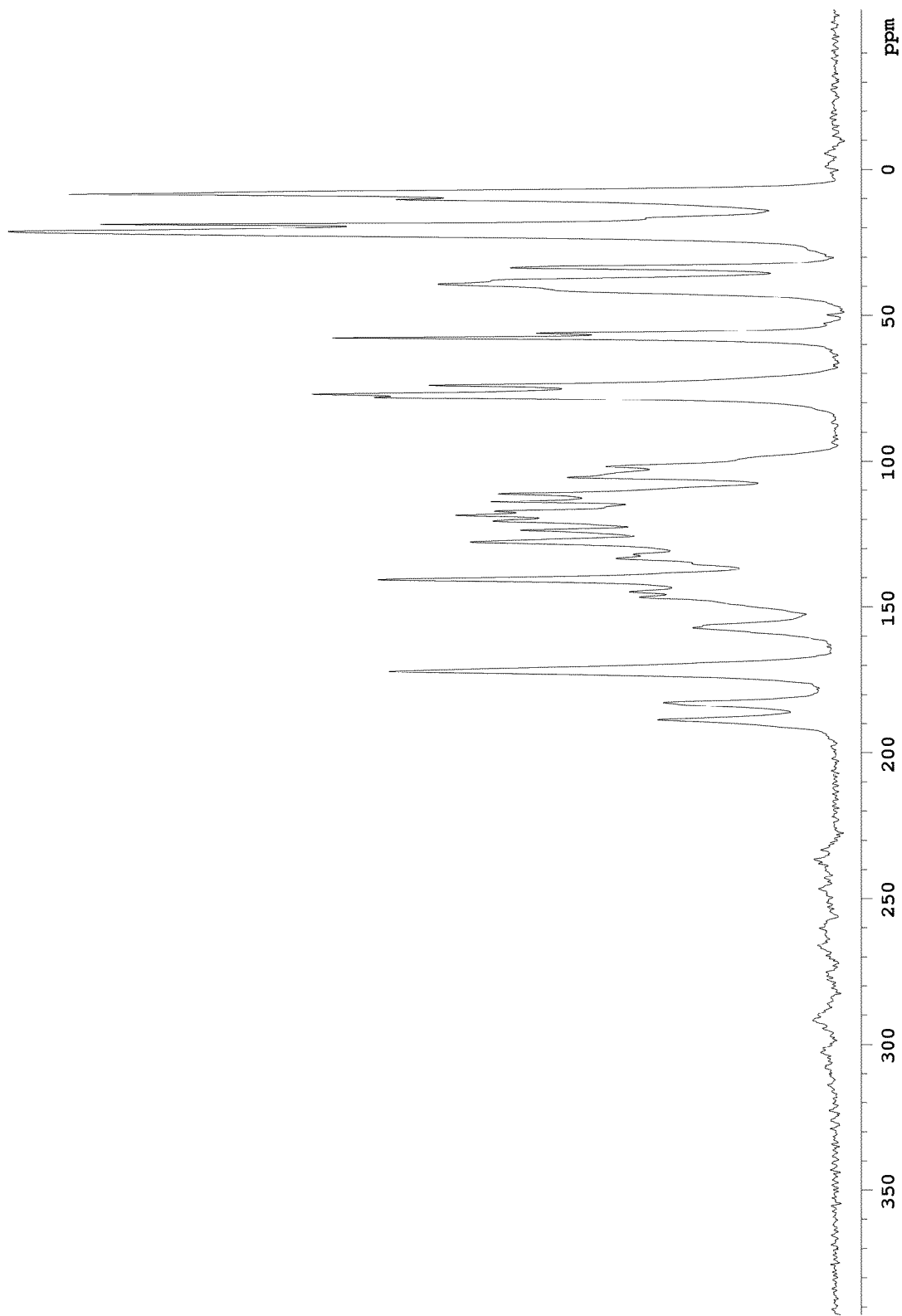
FIG. 29 shows a solid state carbon NMR spectrum of rifaximin Form Xi.
Figure 30:
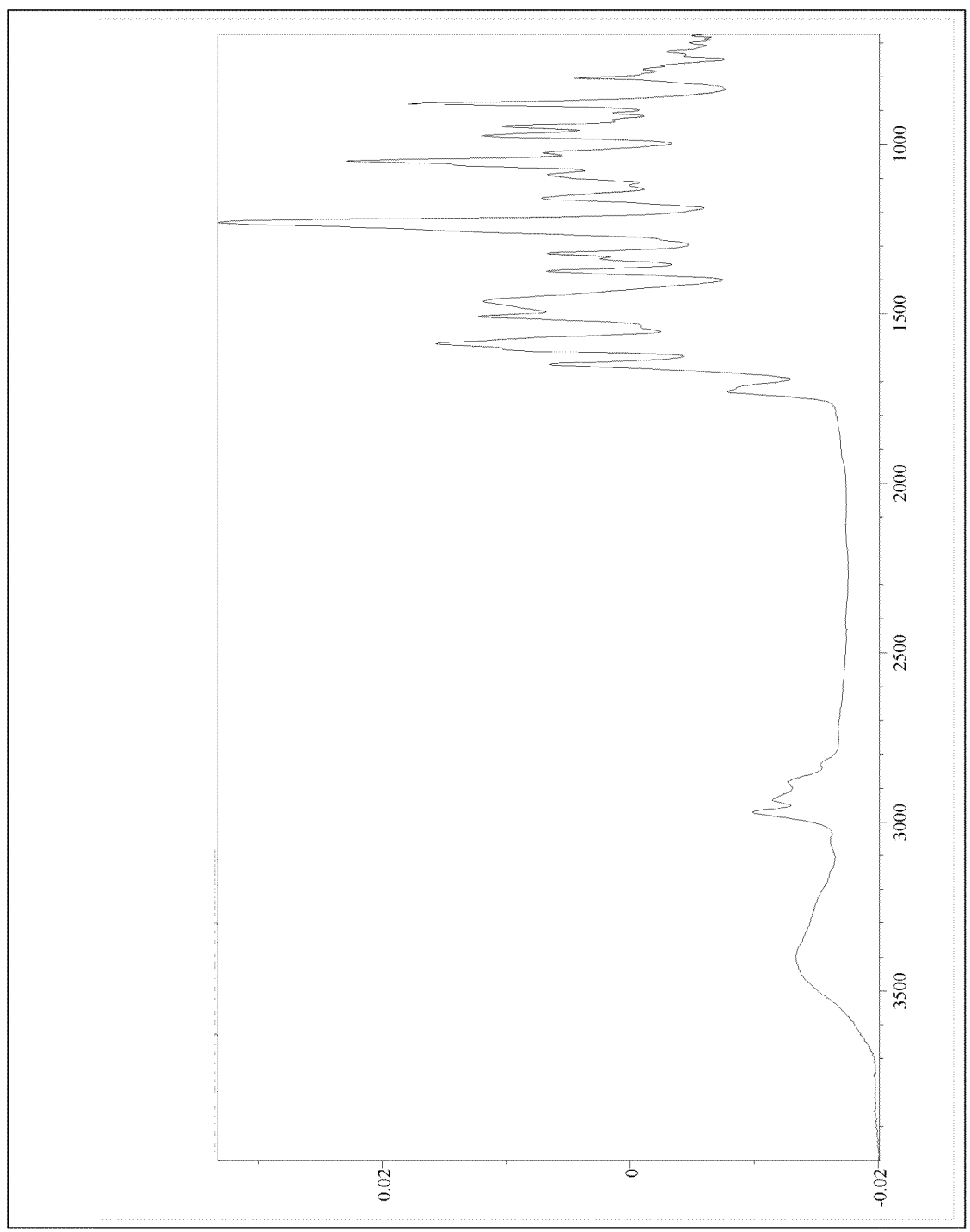
FIG. 30 shows an Infrared spectrum of rifaximin Form Xi.
Figure 31:
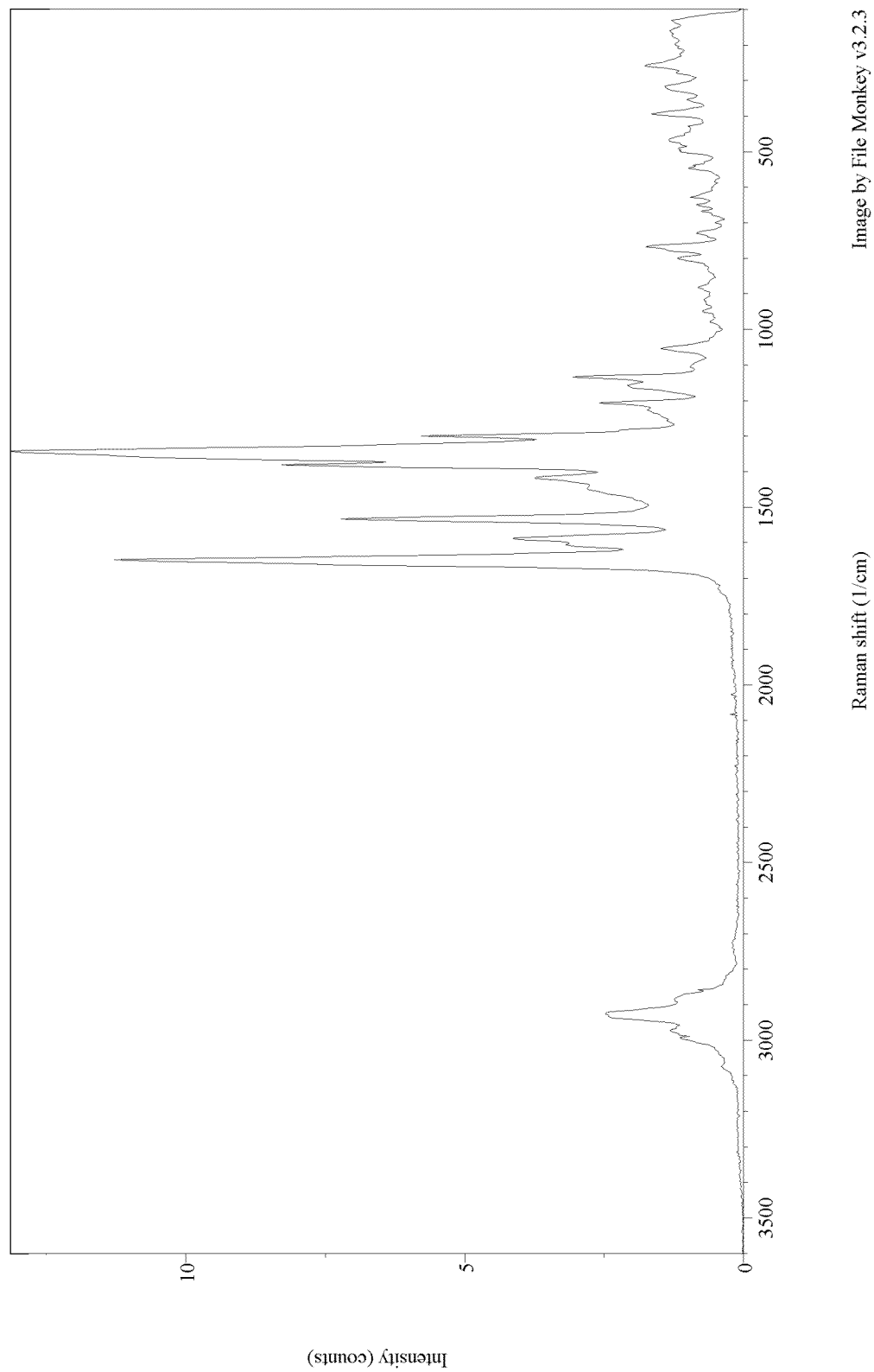
FIG. 31 shows a Raman spectrum of rifaximin Form Xi.

Moisture sorption data for rifaximin Form Xi are shown in FIG. 26. An initial weight loss of 7.2% is observed upon equilibration at 5% RH. The material exhibits a 7.9% weight gain from 5 to 95% RH and a 10.5% weight loss from 95 to 5% RH. The XRPD pattern of the specimen post-moisture sorption (FIG. 27) indicates the material became disordered.

Example 2

Preparation of Form Omicron

Rifaximin Form Omicron was prepared by three methods as described below. The sample generated by Method 1 was further characterized by DSC, TGA, DVS, Raman and ATR-IR spectroscopy, KF, and solution proton and solid state carbon NMR spectrometry.

Method 1:

A slurry of Rifaximin Form Xi in absolute ethanol at 524 mg/mL concentration was prepared and stirred at ambient temperature for approximately one day. The slurry was filtered and characterized while damp with mother liquor by XRPD as Form Omicron.

Method 2:

A slurry of approximately equal masses of Rifaximin Form Xi and Form Eta was prepared in absolute ethanol at 230 mg/mL concentration. The mixture was shaken at ~1° C. for approximately seven days. The slurry was filtered and characterized while damp with mother liquor by XRPD as Form Omicron.

Method 3:

A slurry of approximately equal masses of Rifaximin Form Xi and Form Gamma was prepared in absolute ethanol at 209 mg/mL concentration. The mixture was shaken at ~1° C. for approximately seven days. The slurry was filtered and characterized while damp with mother liquor by XRPD as Form Omicron.

Rifaximin Form Omicron was characterized by high resolution XRPD, DSC, TGA, DVS, Raman and ATR-IR spectroscopy, KF analysis and solution $^1$H— and solid state $^{13}$C NMR spectrometry. FIG. 33 shows the indexing solution and the unit cell parameters for Form Omicron.

A list of XRPD peak positions for one XRPD pattern of Rifaximin Form Omicron is described. Observed and prominent peak lists are included, while representative and characteristic peak lists are not included. One Panalytical XRPD pattern was analyzed. Observed peaks are shown in Table 2, and prominent peaks are listed in Table 3.

The DSC thermogram shows one major broad endotherm at approximately 81.3° C. (peak maximum) and a minor broad endotherm at 135.0° C. (peak maximum) (see FIG. 35). TGA of the same sample indicates two weight loss steps of approximately 18.6 wt % between 26 and 90° C. and approximately 4.0 wt % between 90 and 135° C. The thermal events above 200° C. are likely due to decomposition.

DVS analysis on a moisture balance of the Rifaximin Form Omicron shows an initial weight loss of ~15 wt % at 5% RH upon equilibration (see FIG. 36). The material exhibited a weight gain of 6.2 wt % from 5 to 95% RH and a weight loss of 9.5 wt % from 5 to 95% RH. The sample post-DVS was characterized by XRPD as Form Iota with a significant amount of disorder (see FIG. 37).

The Form Omicron sample contained 4.74 wt % water by KF analysis which may be approximately equivalent to two moles of water. Solution $^1$H NMR specrtroscopy indicated that the sample contained one mole of ethanol per mole of Rifaximin. The weight percentages of water and ethanol content as indicated by KF analysis and the solution $^1$H NMR spectrum, are significantly lower than the weight loss that is indicated in the TG thermogram. This may be a result of surface solvent loss from the sample between analyses as the TGA test was performed 14 days prior to the $^1$H NMR test.

TABLE 1

Characterization of Rifaximin Form Omicron

| Sample ID | Analysis | Result |
|---|---|---|
| 1 | XRPD | Form Omicron |
| 2 | XRPD | Form Omicron |
| 3 | XRPD | Form Omicron |
|  | DSC | Broad major endo @ 81.3° C. (peak max) |
|  |  | Broad endo @ 135.0° C. (peak max) |
|  | TGA | 18.7 wt % loss from 26 to 90° C. (~4 mol EtOH equivalent) |
|  |  | 4.0 wt % loss from 90 to 135° C. (~2 mol water equivalent) |
|  | DVS | −15.0 wt % change on equilibration at 5% RH |
|  |  | 6.2 wt % gain from 5 to 95% RH |
|  |  | 9.5 wt % lost from 95 to 5% RH |
|  | KF | 4.74 wt % water (~2 mol equivalent) |
|  | Post-DVS XRPD | Form Iota |
|  | ATR-IR | Spectrum acquired |
|  | Raman | Spectrum acquired |
|  | $^1$H NMR | 6.0 wt % EtOH (~1 mol equivalent) |
|  | SS $^{13}$C NMR | Spectrum acquired |

TABLE 2

Observed Peaks for Rifaximin Form Omicron

| °2θ | d space (Å) | Intensity (%) |
|---|---|---|
| 5.87 ± 0.20 | 15.063 ± 0.531 | 100 |
| 6.99 ± 0.20 | 12.652 ± 0.372 | 39 |
| 7.77 ± 0.20 | 11.375 ± 0.300 | 8 |
| 8.31 ± 0.20 | 10.644 ± 0.262 | 23 |
| 8.47 ± 0.20 | 10.434 ± 0.252 | 10 |
| 9.13 ± 0.20 | 9.691 ± 0.217 | 20 |
| 9.58 ± 0.20 | 9.235 ± 0.197 | 8 |
| 9.74 ± 0.20 | 9.077 ± 0.190 | 8 |
| 10.86 ± 0.20 | 8.144 ± 0.152 | 5 |
| 12.35 ± 0.20 | 7.166 ± 0.117 | 9 |
| 13.27 ± 0.20 | 6.672 ± 0.102 | 13 |
| 13.69 ± 0.20 | 6.469 ± 0.095 | 17 |
| 14.01 ± 0.20 | 6.323 ± 0.091 | 10 |
| 14.44 ± 0.20 | 6.134 ± 0.086 | 10 |
| 14.79 ± 0.20 | 5.989 ± 0.082 | 10 |
| 15.19 ± 0.20 | 5.832 ± 0.077 | 7 |
| 15.33 ± 0.20 | 5.782 ± 0.076 | 6 |
| 15.68 ± 0.20 | 5.653 ± 0.073 | 8 |
| 15.94 ± 0.20 | 5.559 ± 0.070 | 5 |
| 16.04 ± 0.20 | 5.524 ± 0.069 | 5 |
| 16.31 ± 0.20 | 5.434 ± 0.067 | 5 |
| 16.66 ± 0.20 | 5.321 ± 0.064 | 10 |
| 17.00 ± 0.20 | 5.217 ± 0.062 | 6 |
| 17.35 ± 0.20 | 5.112 ± 0.059 | 7 |
| 17.67 ± 0.20 | 5.021 ± 0.057 | 20 |
| 18.08 ± 0.20 | 4.906 ± 0.054 | 8 |
| 19.04 ± 0.20 | 4.662 ± 0.049 | 12 |
| 19.24 ± 0.20 | 4.614 ± 0.048 | 7 |
| 19.52 ± 0.20 | 4.548 ± 0.047 | 10 |
| 19.85 ± 0.20 | 4.472 ± 0.045 | 8 |
| 20.17 ± 0.20 | 4.402 ± 0.044 | 9 |
| 20.42 ± 0.20 | 4.349 ± 0.043 | 18 |
| 20.76 ± 0.20 | 4.279 ± 0.041 | 7 |
| 21.07 ± 0.20 | 4.216 ± 0.040 | 16 |
| 21.28 ± 0.20 | 4.176 ± 0.039 | 11 |
| 21.61 ± 0.20 | 4.113 ± 0.038 | 15 |
| 21.83 ± 0.20 | 4.072 ± 0.037 | 11 |
| 22.14 ± 0.20 | 4.014 ± 0.036 | 7 |
| 22.36 ± 0.20 | 3.976 ± 0.035 | 7 |
| 22.65 ± 0.20 | 3.927 ± 0.035 | 13 |
| 22.93 ± 0.20 | 3.879 ± 0.034 | 7 |
| 23.20 ± 0.20 | 3.835 ± 0.033 | 6 |
| 23.46 ± 0.20 | 3.791 ± 0.032 | 8 |
| 23.71 ± 0.20 | 3.752 ± 0.031 | 7 |
| 24.15 ± 0.20 | 3.685 ± 0.030 | 7 |
| 24.35 ± 0.20 | 3.655 ± 0.030 | 5 |
| 24.67 ± 0.20 | 3.609 ± 0.029 | 7 |
| 25.07 ± 0.20 | 3.552 ± 0.028 | 8 |
| 25.40 ± 0.20 | 3.506 ± 0.027 | 5 |
| 25.80 ± 0.20 | 3.453 ± 0.027 | 4 |
| 26.22 ± 0.20 | 3.399 ± 0.026 | 9 |
| 26.54 ± 0.20 | 3.359 ± 0.025 | 4 |
| 26.76 ± 0.20 | 3.332 ± 0.025 | 5 |
| 27.17 ± 0.20 | 3.282 ± 0.024 | 7 |
| 27.78 ± 0.20 | 3.212 ± 0.023 | 4 |
| 28.69 ± 0.20 | 3.111 ± 0.021 | 5 |
| 28.88 ± 0.20 | 3.092 ± 0.021 | 6 |
| 29.21 ± 0.20 | 3.057 ± 0.021 | 4 |
| 29.46 ± 0.20 | 3.032 ± 0.020 | 4 |
| 23.71 ± 0.20 | 3.752 ± 0.031 | 100 |
| 24.15 ± 0.20 | 3.685 ± 0.030 | 39 |
| 24.35 ± 0.20 | 3.655 ± 0.030 | 8 |
| 24.67 ± 0.20 | 3.609 ± 0.029 | 23 |
| 25.07 ± 0.20 | 3.552 ± 0.028 | 10 |
| 25.40 ± 0.20 | 3.506 ± 0.027 | 20 |
| 25.80 ± 0.20 | 3.453 ± 0.027 | 8 |
| 26.22 ± 0.20 | 3.399 ± 0.026 | 8 |
| 26.54 ± 0.20 | 3.359 ± 0.025 | 5 |
| 26.76 ± 0.20 | 3.332 ± 0.025 | 9 |
| 27.17 ± 0.20 | 3.282 ± 0.024 | 13 |
| 27.78 ± 0.20 | 3.212 ± 0.023 | 17 |
| 28.69 ± 0.20 | 3.111 ± 0.021 | 10 |
| 28.88 ± 0.20 | 3.092 ± 0.021 | 10 |
| 29.21 ± 0.20 | 3.057 ± 0.021 | 10 |
| 29.46 ± 0.20 | 3.32 0.020 | 7 |

TABLE 3

Prominent Peaks for Rifaximin Form Omicron

| °2θ | d space (Å) | Intensity (%) |
|---|---|---|
| 5.87 ± 0.20 | 15.063 ± 0.531 | 100 |
| 6.99 ± 0.20 | 12.652 ± 0.372 | 39 |
| 8.31 ± 0.20 | 10.644 ± 0.262 | 23 |
| 9.13 ± 0.20 | 9.691 ± 0.217 | 20 |
| 13.27 ± 0.20 | 6.672 ± 0.102 | 13 |
| 13.69 ± 0.20 | 6.469 ± 0.095 | 17 |
| 17.67 ± 0.20 | 5.021 ± 0.057 | 20 |

Example 3

Preparation of Form Pi

Method 1:

A reactor vessel was charged with a slurry of approximately 8.7 g of Rifaximin in 52 mL of absolute ethanol containing 0.9 wt % water (determined by Karl Fisher water analysis), that was prepared in advance by stirring for approximately 45 minutes. Absolute ethanol (9 mL) was used to rinse the slurry preparation container and added to the reactor vessel. The seed slurry was prepared by stirring 135.7 mg of Rifaximin in 1 mL of absolute ethanol for approximately 90 minutes. The seed slurry was added directly to the reactor as required. The slurry was heated to 55° C., cooled to 40° C., and then the seed slurry was added and the reactor was held for stirring for one hour before cooling to 0° C. over 200 min. The slurry was held for approximately 2 hours at 0° C. After the crystallization, the slurry was discharged from the reactor vessel and immediately filtered to dry land using a Buchner filter and funnel and grade 1 filter paper. The wet cake was dried in a vacuum oven at ambient temperature for four days. Typical pressure values for the vacuum oven are about 40 to about 50 mTorr.

Method 2:

Form π was also prepared by drying a mixture of Rifaximin Forms Omicron and Zeta, damp with absolute ethanol, in a vacuum oven at approximately 40° C. for 1 day. Typical pressure values for the vacuum oven are about 40 to about 50 mTorr.

Method 3:

Rifaximin Form Beta was recrystallized from absolute ethanol by dissolving approximately 140 mg/mL in absolute ethanol at 55° C. Detailed methods of forming Beta are known in the art and can be found in U.S. Pat. No. 7,045,620, which is incorporated by reference herein. The solution was then cooled to 40° C., seeded with approximately 1.5 wt % seed (with respect to Rifaximin input mass), that was prepared by dissolving approximately 140 mg/mL Rifaximin Form Eta in absolute ethanol. The slurry was cooled to 0° C. over 200 minutes then held for approximately 2 hours before filtering and drying in a vacuum oven at ambient temperature for approximately 4 days. Typical pressure values for the vacuum oven are about 40 to about 50 mTorr. The dried solid was characterized by XRPD as Form Pi, and shown in FIGS. 9 and 12-14.

Rifaximin Form Pi appeared to be a variable solvate. The unit-cell parameters can expand or contract to accommodate the solvate composition. XRPD peak positions are a direct result of the unit cell parameters, and therefore one single XRPD pattern will not be representative of the crystal form. A list of XRPD peak positions is provided for two XRPD patterns that represent the extremes of the unit-cell volumes for Rifaximin Pi and these two patterns were combined to provide peak position ranges, listed in Table 10 and Table 11. Observed and prominent peak lists are included, while representative and characteristic peak lists are not included. Only one Panalytical XRPD pattern were collected. Observed peaks are shown in Table 6 and Table 8, and prominent peaks are listed in Tables 7 and 9.

To investigate if preferred orientation was present, two XRPD patterns were collected on the same undisturbed specimen from the coarser-grained fraction of the sample. These grains appeared to have faceted surfaces by visual inspection with the unaided eye. XRPD patterns were collected on this specimen using the Bragg-Brentano geometry and the transmission geometry to determine if preferred orientation was affecting the relative intensities of the sharp (Bragg) peaks. FIG. 15 shows considerable variation of the relative intensities and peak positions of the two prominent Bragg peaks. The variation of relative intensity of these closely positioned peaks indicates the presence of preferred orientation in this specimen and suggests specimens with faceted surfaces are likely to display preferred orientation because the facets are from single crystals of Form Pi. These two patterns also had the lowest diffuse background generated by disordered crystalline material compared to all other patterns collected on Form Pi samples.

The DSC thermogram shows one major broad endotherm with a peak maximum at 66.4° C. and a minor endotherm with a peak maximum at 203.4° C. (see FIG. 16). TGA of the sample shows a weight loss of 2.49 wt % between 26 and 80° C. that is likely associated with the first broad endothermic event, and weight loss of 1.56 wt % between 80 and 203° C. The thermal events above 203° C. are likely due to decomposition.

DVS analysis on a moisture balance of the Rifaximin Form Pi sample shows an initial weight loss of 1.3 wt % at 5% RH upon equilibration (see FIG. 17). The material is reversibly hygroscopic and exhibited adsorption of 10.5 wt % from 5 to 95% RH and desorption of 11.3% from 95 to 5% RH. The material post-DVS analysis was characterized by XRPD as Form Pi.

The Form Pi sample was found to contain 1.67 wt % water by KF analysis that is equivalent to approximately 0.75 moles of water per mole Rifaximin. Solution proton NMR spectroscopy of the same sample was consistent with the Rifaximin structure with the presence of approximately 0.67 moles of ethanol per mole of Rifaximin. ATR-IR, Raman spectra and solid-state $^{13}$C CP/MAS NMR spectra were also obtained. The peaks in the solid state $^{13}$C CP/MAS NMR spectra were broader than those in the spectra when compared to known forms of rifaximin, which indicates that Form Pi is disordered.

TABLE 4

Preparation of Rifaximin Pi

| Sample ID | Analysis | Preparation Method |
|---|---|---|
| 1 | Pi (XRPD) | Method 1 |
| 2 | Pi (XRPD) | Method 1 |
| 3 | Pi (XRPD) | Method 3 |
| 4 | Pi (XRPD) | Method 2 |
| 5 | Pi (XRPD) | Method 4 |
| 6 | Pi (XRPD) | Method 4 |
| 7 | Pi (XRPD) | Method 4 |

TABLE 5

Characterization of Rifaximin Pi

| Analysis | Result |
| --- | --- |
| XRPD | Pi |
| XRPD[a] | Pi |
| XRPD[b] | Pi |
| DSC | Broad major endo @ 66.4° C. (peak max) |
| | Broad endo @ 203.4° C. (peak max) |
| TGA | 2.5 wt % loss from 26 to 80° C. |
| | (~0.4 mol EtOH equivalent) |
| | 1.6 wt % loss from 80 to 203° C. |
| | (~0.7 mol water equivalent) |
| DVS | −1.3 wt % change on equilibration at 5% RH |
| | 10.5 wt % gain from 5 to 95% RH |
| | 11.3 wt % lost from 95 to 5% RH |
| KF | 1.67 wt %, ~0.75 mol water |
| Post-DVS XRPD | Pi |
| ATR-IR | Spectrum acquired |
| Raman | Spectrum acquired |
| $^1$H NMR | ~0.67 mol EtOH |
| SS $^{13}$C NMR | Spectrum acquired |

[a] Large particles were preferentially selected from top of sample after horizontal oscillation. Bragg-Brentano geometry.
[b] RH ranged from 24 to 27% during data collection. Transmission geometry.

TABLE 6

Observed peaks for Rifaximin Pi

| °2θ | d space (Å) | Intensity (%) |
| --- | --- | --- |
| 6.91 ± 0.20 | 12.797 ± 0.381 | 93 |
| 7.16 ± 0.20 | 12.350 ± 0.355 | 100 |
| 9.15 ± 0.20 | 9.669 ± 0.216 | 44 |

TABLE 7

Prominent peaks for Rifaximin Pi

| °2θ | d space (Å) | Intensity (%) |
| --- | --- | --- |
| 6.91 ± 0.20 | 12.797 ± 0.381 | 93 |
| 7.16 ± 0.20 | 12.350 ± 0.355 | 100 |

TABLE 8

Observed peaks for Rifaximin Pi

| °2θ | d space (Å) | Intensity (%) |
| --- | --- | --- |
| 7.05 ± 0.20 | 12.532 ± 0.365 | 94 |
| 7.29 ± 0.20 | 12.130 ± 0.342 | 100 |
| 9.33 ± 0.20 | 9.483 ± 0.207 | 52 |

TABLE 9

Prominent peaks for Rifaximin Pi

| °2θ | d space (Å) | Intensity (%) |
| --- | --- | --- |
| 7.05 ± 0.20 | 12.532 ± 0.365 | 94 |
| 7.29 ± 0.20 | 12.130 ± 0.342 | 100 |

TABLE 10

Observed peak ranges for Rifaximin Pi

| °2θ Range | d space (Å) Range | Intensity (%) Range |
| --- | --- | --- |
| (6.91-7.05) ± 0.20 | 12.797 ± 0.381-12.532 ± 0.365 | 93-94 |
| (7.16-7.29) ± 0.20 | 12.350 ± 0.355-12.130 ± 0.342 | 100 |
| (9.15-9.33) ± 0.20 | 9.669 ± 0.216-9.483 ± 0.207 | 44-52 |

TABLE 11

Prominent peak ranges for Rifaximin Pi

| °2θ Range | d space (Å) Range | Intensity (%) Range |
| --- | --- | --- |
| (6.91-7.05) ± 0.20 | 12.797 ± 0.381-12.532 ± 0.365 | 93-94 |
| (7.16-7.29) ± 0.20 | 12.350 ± 0.355-12.130 ± 0.342 | 100 |

Example 4

Preparation of Form Mu

Form Mu was obtained by fast evaporation of rifaximin in 1:1 (v/v) ethanol/heptane at ambient temperature. It was also shown that Form Theta will convert to Form μ upon exposure to 75% RH at ambient temperature. Additionally, Form Zeta converts to Form Mu upon exposure to 51% RH at ambient temperature. Form μ irreversibly desolvates to Form Gamma, when exposed to ~60° C. under vacuum for ~24 hours.

Approximately 3 grams of rifaximin was dissolved in 60 mL ethanol. The solution was then diluted with equal volume of heptane and filtered into an open beaker or crystallization dish. The filtered solution was left at ambient in a fume hood for fast evaporation.

Details of each experiment are presented in Table 12. For example Rifaximin form Mu was prepared by first dissolving 3.2422 g of rifaximin into 60 mL ethanol. A red solution observed. The solution was then diluted 1:1 with 60 mL heptane, mixed and filtered through a 0.2 μm Nylon filter into an open crystallization dish. The crystallization dish was left at ambient in fume hood for fast evaporation of solvent. Solvent evaporation was completed overnight and orange blades with birefringence and extinction was produced.

Rifaximin Form μ is a variable solvated/hydrated crystalline form. It is generated through the hydration of Form Theta (which, in turn, is generated through the desolvation of Form ζ). Its crystal lattice can expand or contract to accommodate changes in solvent and/or water content. The structure, with a calculated range for its volume per formula unit between 1279 and 1293 Å3, contains voids estimated to be between approximately 252 and 266 Å3, respectively, that can be occupied by solvent and/or water.

Characterization of various samples of Form μ is consistent with the known variability in its solvent/water content. For example, approximately 0.6 moles of EtOH (per mole of rifaximin) and 12.7 wt % water was observed in one sample while approximately 0.5 moles of EtOH and 14.1 wt % water was observed in another sample.

Rifaximin Form Theta will convert to Form μ upon exposure to 75% RH. Additionally, Form μ was generated at 51% RH. A slightly disordered Form Mu (as a mixture with Form Iota) was generated at 44% RH. Rifaximin Form μ irreversibly dehydrates to Form Gamma.

Rifaximin Form gamma can be prepared by slurrying rifaximin in a solvent, e.g. ethanol, in a suitable reactor or flask that is equipped with stirring, mechanical or magnetic, a thermometer and a reflux condenser. The suspension is heated at 40-80° C., e.g. 45° C. to 70° C. or 55° C. to 65° C., with stirring until complete dissolution of the solid. While maintaining this temperature a second solvent, e.g. water, is added over 1-120 minutes, e.g. 10-60 minutes or 20-40 minutes. At the end of the addition of the second solvent the temperature is brought to 10-50° C., e.g. 20° C. to 40° C. or 25° C. to 35° C., in 10-120 minutes, e.g. 20-60 minutes or 30-50 minutes, and is kept at this value until crystallization is observed, then the temperature is further lowered to −10-10° C., e.g. −7° C. to 7° C. or −5° C. to 5° C., over 0.5-5 hours, e.g. 1-4 hours or 1.5-3 hours, and kept at this temperature for 1-24 hours, e.g. 2-12 hours or 4-8 hours. The suspension is then filtered and the solid is washed with the second solvent, e.g. water. The filter cake is dried under vacuum at room temperature until a constant weight is observed.

Rifaximin Form Zeta can be prepared by suspending rifaximin in a mixture of solvents, e.g. ethanol and water, with a ratio of 4:1, at 15° C. to 35° C., e.g. 20° C. to 30° C. or 22° C. to 27° C. for 1-10 hours, e.g. 2-8 hours or 466 hours. The solids are isolated, e.g. via decantation or filtration, and the solids are stored in a refrigerator.

Rifaximin Form Theta was can be prepared by drying Form ζ under vacuum at ambient temperature for approximately 6 hours. Form Theta may be an ethanolate based on $^1$H-NMR results. One sample contains two moles of ethanol per mole of rifaximin by $^1$H-NMR, but the volume estimated from the tentative XRPD indexing solution indicates the unit cell is able to accommodate up to 4 moles of ethanol per mole of rifaximin. XRPD patterns of Form Theta were indexed successfully. Successful indexing of the powder diffraction pattern exhibited by this form provides support that Form Theta is a single crystalline phase. Rifaximin Form Theta was obtained at large scale by vacuum drying of Form ζ. In this Example, 58.96 g of rifaximin was added to 300 mL of ethanol with stirring at ambient condition. The rifaximin almost completely dissolved initially and yielded a very dark red solution. With continuous stirring, the solution became lighter in color and turbidity increased until an orange/red paste was formed. At that point, another 100 mL of ethanol was added. The total volume of ethanol was 400 mL. The slurry sample was then vacuum filtered through a filter paper under nitrogen environment (21% RH, 22° C.) and a red-orange paste was obtained. Once filtrate stopped dripping from the end of funnel, the filter cake was broken loose on the filter paper with a spatula while vacuum and nitrogen still remained on. The total drying time of the sample on filter paper was approximately 30 minutes.

The resulting solid was identified as Form Zeta by XRPD. This solid sample was later dried under vacuum for approximately 6 hours at ambient temperature. The post XRPD pattern confirms that the solid converted to Form Theta after vacuum drying.

Additional methods to prepare rifaximin Form Mu (as a pure phase or as mixtures with other forms), which did not utilize 1:1 (v/v) ethanol/heptane, are also known. These experiments are summarized in Table 12A. It was shown that Form Theta will convert at least partially to Form μ upon exposure to 75% RH. Additionally, Form Zeta converts to Form Mu upon exposure to 51% RH at ambient temperature. A slightly disordered Form Mu (as a mixture with Form Iota) was generated from ethanol at 44% RH and ambient temperature.

The material was analyzed by x-ray powder diffractometry (XRPD) and the patterns were indexed. In addition, the material was characterized by differential scanning calorimetry (DSC), thermogravimetric analysis (TGA), dynamic vapor sorption (DVS), Karl-Fischer titration (KF), solution proton ($^1$H—) and solid-state (SS-) nuclear magnetic resonance (NMR), and attenuated total reflectance infrared (ATR-IR) and Raman spectroscopy.

The XRPD patterns of two Form μ samples are shown in FIG. 1. Since Form Mu is a variable system with flexible unit cell structure that may readily expand or contract to accommodate various amounts of solvent, it should be noted that the illustrated patterns are only representations of two discrete examples of a series of peak ranges that may be exhibited by Form μ.

The list of peak positions for each XRPD pattern of rifaximin Form μ illustrated in Table 13 is presented in FIG. 2 and FIG. 3, respectively. Observed and prominent peak lists are included in Tables 13-16. Representative and characteristic peak lists are not included. One PANalytical pattern was analyzed for each sample.

Figure 4:
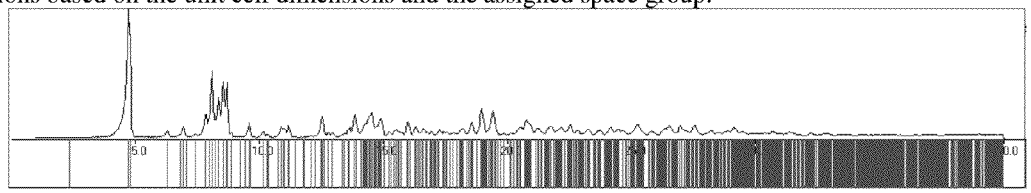
FIG. 4 shows a tentative indexing solution for rifaximin Form Mu.
Figure 5:
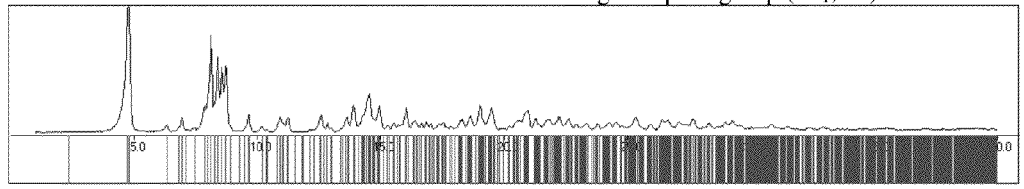
FIG. 5 shows a tentative indexing solution for rifaximin Form Mu.

The XRPD patterns of rifaximin Form Mu were indexed and are illustrated in FIG. 4 and FIG. 5. Indexing is the process of determining the size and shape of the unit cell given the peak positions in a diffraction pattern.

Agreement between the allowed peak positions, marked with bars in FIG. 4 and FIG. 5, and the observed peaks indicates a consistent unit cell determination. Successful indexing of the pattern indicates that each sample is composed primarily of a single crystalline phase. Space groups consistent with the assigned extinction symbol, unit cell parameters, and derived quantities are tabulated in Table 17.

The volume of rifaximin (1027 Å$^3$/molecule) was derived from a previously reported rifaximin hydrate structure. A typical value of 20 Å$^3$/molecule was used for water of hydration. Therefore, given the volume per formula unit from the indexing solution for Form μ of 1293.4 Å$^3$, approximately 226 Å$^3$ are available for water. Up to 13 moles of water per rifaximin are possible in the available volume. A second XRPD pattern of Form μ was also indexed with a volume per formula unit of 1278.5 Å$^3$, and up to 12.5 moles of water per rifaximin are possible in the available volume. Analysis of the actual Form μ samples by KF and $^1$H-NMR shows that sample contains approximately 0.5 mole of ethanol and 7 moles of water per mole of rifaximin, while an additional sample contains approximately 0.6 mole of ethanol and 6 moles of water per mole of rifaximin (Table 20).

The XRPD patterns listed above represent a single phase of rifaximin, designated as Form μ. Because Form μ is a variable solvate, the unit cell parameters may change via expansion or contraction to accommodate the solvent. XRPD peak positions are a direct result of the unit cell parameters. Peak lists are presented for the two patterns above and are combined in Table 18 and Table 19 to provide peak position ranges.

Figure 7:
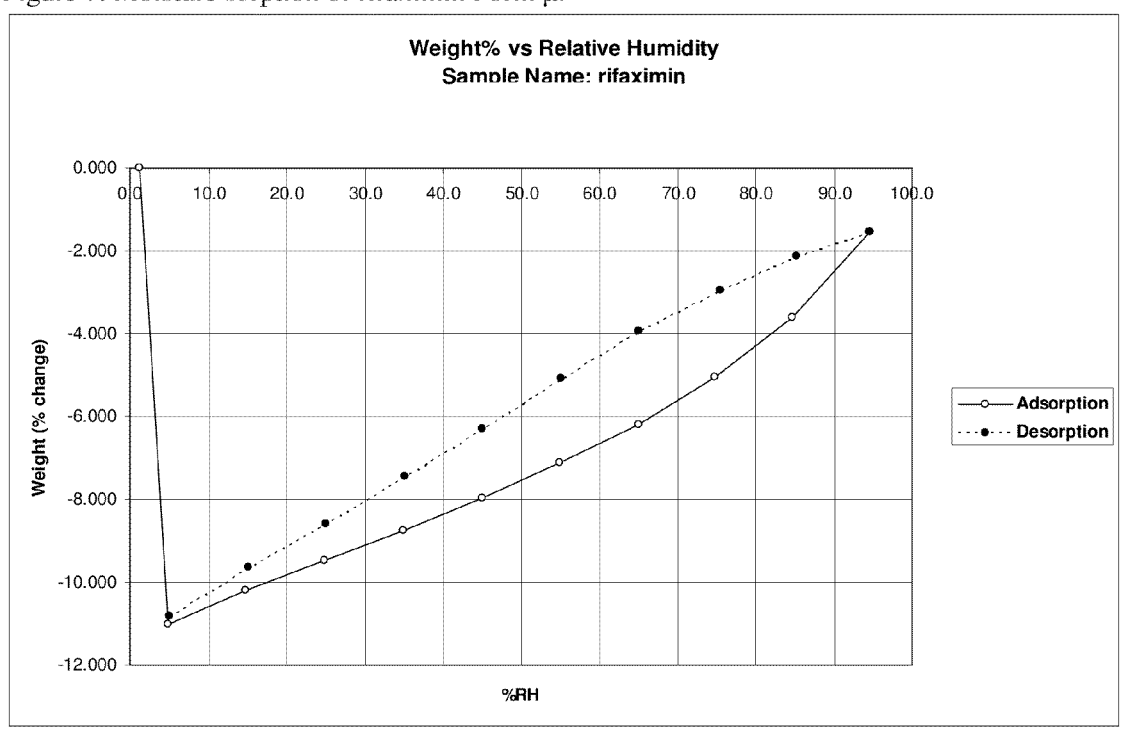
FIG. 7 shows moisture sorption (DVS) data of rifaximin Form Mu.
Figure 8:
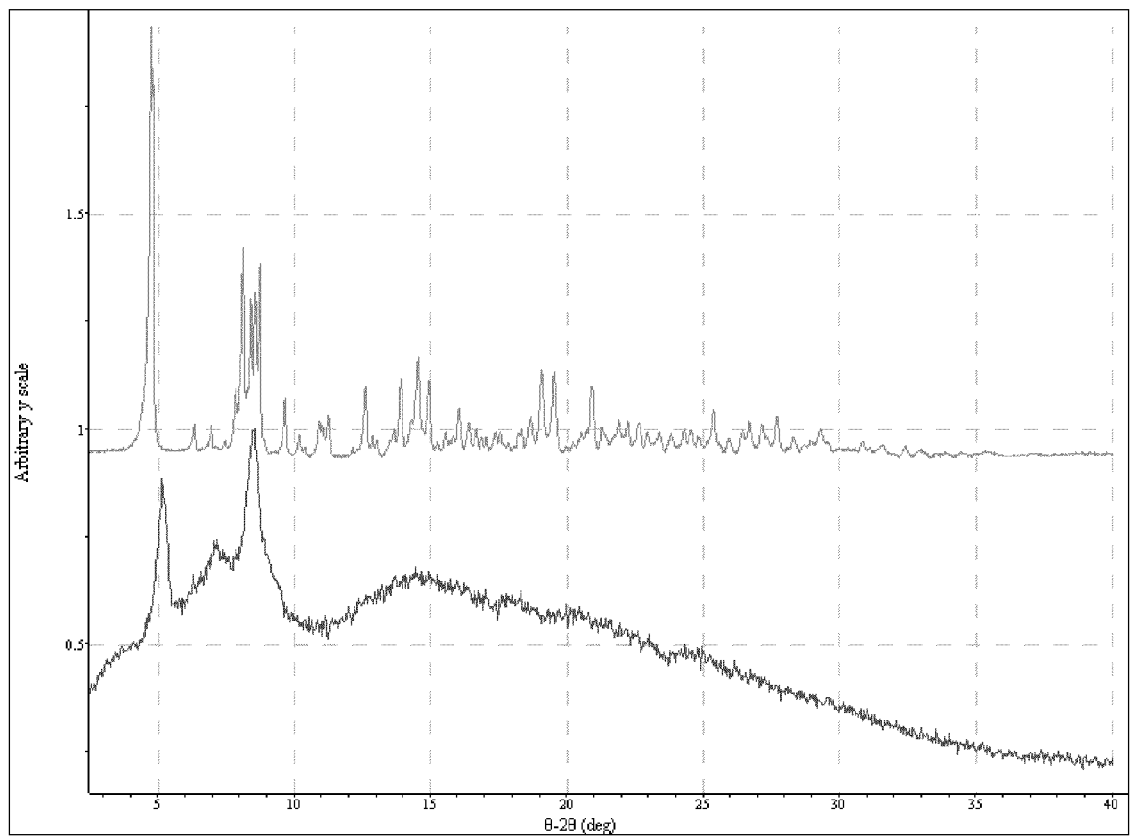
FIG. 8 shows post-DVS XRPD of rifaximin Form Mu.

Additional characterization data for rifaximin Form Mu by DSC, TGA, DVS and XRPD before and after DVS are presented in FIG. 6 through FIG. 8, and are summarized in Table 20.

DSC result shows a broad endotherm with signal maximum at approximately 92° C. and enthalpy change of 443.1 J/g. TGA of the same sample indicates a weight loss of approximately 15.7% when heated up to 100° C. (FIG. 6).

Moisture sorption data for rifaximin Form μ are shown in FIG. 7. An initial weight loss of 11.0% was observed upon equilibration at 5% RH. The material exhibited a 9.5% weight gain from 5 to 95% RH and a 9.3% weight loss from 95 to 5% RH. The XRPD pattern of the specimen post-moisture sorption (FIG. 8) indicates the material has converted to Form Gamma. The chemical composition of the specimen post-moisture sorption was not determined.

Other characterizations, including NMR, KF, ATR-IR, and Raman analysis results are also summarized in Table 20.

Physical stability data is summarized in Table 21. Form μ irreversibly desolvates to Form γ, a highly disordered form, when exposed to ~60° C. under vacuum for ~24 hours; this result was repeated in a separate experiment. Form μ converted to Form Beta when the sample was exposed to 97% RH at ambient temperature for ~16 days.

The XRPD pattern of Form Mu was indexed successfully. Form Mu is identified as a variable system of which the unit cell parameters may change via expansion or contraction to accommodate the solvent. Multiple XRPD patterns obtained on various samples suggest that a range exist for the reflection peaks observed in Form Mu. Indexing solutions were obtained on two representative XRPD patterns of Form Mu but do not necessarily indicate the upper and lower limit of the range. Rather they can be considered two discrete examples of the Form Mu series. Theoretical calculation from the indexing solutions indicates that the two samples may be able to accommodate up to 12.5 or 13 moles of water per mole of rifaximin based on the void space within the unit cell. Karl-Fischer analysis on the two Form μ samples shows that the material contains approximately 6 to 7 moles of water per mole of rifaximin. $^1$H-NMR analysis of the two indexed Form Mu sample shows that they contain 0.5 to 0.6 mole of ethanol per mole of rifaximin.

TABLE 12

Preparation of Rifaximin Form μ

| Rifaximin (g) | EtOH/ Heptane (1:1 v/v, total mL) | Condition[1] | Observation[2] | XRPD result |
|---|---|---|---|---|
| 3.2422 | 120 | FE, RT, 1 day | Orange blades, B/E | μ |
| 3.1467 | 120 | FE, RT, 1 day | Orange blades, B/E | μ |
| 3.2548 | 120 | FE, RT, 1 day | Red blades, B/E | μ |
| 3.2354 | 120 | FE, RT, 4 days | Red blades, B/E | μ |
| 3.1974 | 120 | FE, RT, 1 day | Red blades, B/E | μ |
| 3.2557 | 120 | FE, RT, 1 day | Red blades, B/E | μ |
| 3.1361 | 120 | FE, RT, 1 day | Red blades, B/E | μ |
| 3.2052 | 120 | FE, RT, 1 day | Red blades, B/E | μ |
|  |  |  |  | μ |
| 0.1441 | 6 | FE, RT, 1 day | Blades, B | μ |

[1]FE = fast evaporation; RT = room temperature.
[2]B = birefringent; E = extinction.

TABLE 12A

Attempts to Prepare Rifaximin Form Mu through other Methods

| Method | Observations | Results |
|---|---|---|
| precipitation from EtOH, isolated under 44% RH (RT) | bright orange-red | μ + ι disordered |
| ζ exposed to 51% RH (RT), ~20 min | bright orange | μ |
| θ exposed to 75% RH (RT), 6 hrs | orange | μ + ι |
| θ exposed to 75% RH (40° C.), 6 hrs | orange | μ + η |

TABLE 13

Observed Peaks for Rifaximin Form Mu

| °2θ | d space (Å) | Intensity (%) |
|---|---|---|
| 4.72 ± 0.10 | 18.729 ± 0.405 | 100 |
| 4.79 ± 0.10 | 18.467 ± 0.394 | 84 |
| 6.29 ± 0.10 | 14.054 ± 0.227 | 7 |
| 6.94 ± 0.10 | 12.736 ± 0.186 | 10 |
| 7.44 ± 0.10 | 11.879 ± 0.162 | 5 |
| 7.84 ± 0.10 | 11.272 ± 0.145 | 20 |
| 8.11 ± 0.10 | 10.901 ± 0.136 | 55 |
| 8.36 ± 0.10 | 10.575 ± 0.128 | 32 |
| 8.55 ± 0.10 | 10.348 ± 0.122 | 44 |
| 8.70 ± 0.10 | 10.169 ± 0.118 | 44 |
| 8.88 ± 0.10 | 9.959 ± 0.113 | 5 |
| 9.60 ± 0.10 | 9.215 ± 0.097 | 13 |
| 10.15 ± 0.10 | 8.716 ± 0.087 | 6 |
| 10.32 ± 0.10 | 8.575 ± 0.084 | 3 |
| 10.88 ± 0.10 | 8.128 ± 0.075 | 10 |
| 11.02 ± 0.10 | 8.030 ± 0.073 | 9 |
| 11.20 ± 0.10 | 7.899 ± 0.071 | 11 |
| 12.09 ± 0.10 | 7.322 ± 0.061 | 3 |
| 12.54 ± 0.10 | 7.059 ± 0.057 | 18 |
| 12.79 ± 0.10 | 6.922 ± 0.054 | 6 |
| 12.96 ± 0.10 | 6.833 ± 0.053 | 6 |
| 13.42 ± 0.10 | 6.596 ± 0.049 | 5 |
| 13.63 ± 0.10 | 6.499 ± 0.048 | 9 |
| 13.86 ± 0.10 | 6.390 ± 0.046 | 19 |
| 14.54 ± 0.10 | 6.090 ± 0.042 | 21 |
| 14.90 ± 0.10 | 5.948 ± 0.040 | 16 |
| 15.25 ± 0.10 | 5.811 ± 0.038 | 6 |
| 15.50 ± 0.10 | 5.718 ± 0.037 | 8 |
| 16.00 ± 0.10 | 5.540 ± 0.035 | 14 |
| 16.30 ± 0.10 | 5.438 ± 0.033 | 10 |
| 16.62 ± 0.10 | 5.335 ± 0.032 | 8 |
| 16.78 ± 0.10 | 5.282 ± 0.031 | 6 |
| 16.97 ± 0.10 | 5.226 ± 0.031 | 6 |
| 17.27 ± 0.10 | 5.135 ± 0.030 | 8 |
| 17.47 ± 0.10 | 5.077 ± 0.029 | 6 |
| 17.57 ± 0.10 | 5.048 ± 0.029 | 6 |
| 17.84 ± 0.10 | 4.973 ± 0.028 | 5 |
| 18.20 ± 0.10 | 4.873 ± 0.027 | 9 |
| 18.57 ± 0.10 | 4.778 ± 0.026 | 13 |
| 18.97 ± 0.10 | 4.678 ± 0.025 | 24 |
| 19.42 ± 0.10 | 4.570 ± 0.023 | 22 |
| 19.88 ± 0.10 | 4.467 ± 0.022 | 4 |
| 20.78 ± 0.10 | 4.275 ± 0.020 | 16 |
| 21.76 ± 0.10 | 4.084 ± 0.019 | 10 |
| 22.18 ± 0.10 | 4.008 ± 0.018 | 10 |
| 22.52 ± 0.10 | 3.949 ± 0.017 | 12 |
| 22.83 ± 0.10 | 3.895 ± 0.017 | 7 |
| 23.27 ± 0.10 | 3.823 ± 0.016 | 8 |
| 23.70 ± 0.10 | 3.754 ± 0.016 | 7 |
| 24.17 ± 0.10 | 3.682 ± 0.015 | 9 |
| 24.47 ± 0.10 | 3.638 ± 0.015 | 8 |
| 24.67 ± 0.10 | 3.609 ± 0.014 | 7 |
| 25.26 ± 0.10 | 3.526 ± 0.014 | 12 |
| 25.81 ± 0.10 | 3.452 ± 0.013 | 7 |
| 26.53 ± 0.10 | 3.360 ± 0.012 | 11 |
| 26.98 ± 0.10 | 3.305 ± 0.012 | 11 |
| 27.55 ± 0.10 | 3.238 ± 0.012 | 11 |
| 28.23 ± 0.10 | 3.161 ± 0.011 | 7 |
| 28.50 ± 0.10 | 3.132 ± 0.011 | 6 |
| 28.87 ± 0.10 | 3.093 ± 0.011 | 7 |
| 29.15 ± 0.10 | 3.064 ± 0.010 | 10 |

TABLE 14

Prominent Peaks for Rifaximin Form μ

| °2θ | d space (Å) | Intensity (%) |
|---|---|---|
| 4.72 ± 0.10 | 18.729 ± 0.405 | 100 |
| 4.79 ± 0.10 | 18.467 ± 0.394 | 84 |
| 7.84 ± 0.10 | 11.272 ± 0.145 | 20 |
| 8.11 ± 0.10 | 10.901 ± 0.136 | 55 |

TABLE 14-continued

Prominent Peaks for Rifaximin Form μ

| °2θ | d space (Å) | Intensity (%) |
|---|---|---|
| 8.36 ± 0.10 | 10.575 ± 0.128 | 32 |
| 8.55 ± 0.10 | 10.348 ± 0.122 | 44 |
| 8.70 ± 0.10 | 10.169 ± 0.118 | 44 |
| 9.60 ± 0.10 | 9.215 ± 0.097 | 13 |
| 12.54 ± 0.10 | 7.059 ± 0.057 | 18 |

TABLE 15

Observed Peaks for Rifaximin Form μ

| °2θ | d space (Å) | Intensity (%) |
|---|---|---|
| 4.75 ± 0.10 | 18.597 ± 0.400 | 99 |
| 4.82 ± 0.10 | 18.339 ± 0.388 | 100 |
| 6.32 ± 0.10 | 13.980 ± 0.224 | 8 |
| 6.96 ± 0.10 | 12.705 ± 0.185 | 14 |
| 7.46 ± 0.10 | 11.852 ± 0.161 | 7 |
| 7.86 ± 0.10 | 11.248 ± 0.145 | 23 |
| 8.13 ± 0.10 | 10.879 ± 0.135 | 77 |
| 8.39 ± 0.10 | 10.533 ± 0.127 | 60 |
| 8.56 ± 0.10 | 10.328 ± 0.122 | 53 |
| 8.73 ± 0.10 | 10.130 ± 0.117 | 57 |
| 8.90 ± 0.10 | 9.941 ± 0.113 | 8 |
| 9.65 ± 0.10 | 9.167 ± 0.096 | 17 |
| 10.18 ± 0.10 | 8.687 ± 0.086 | 7 |
| 10.37 ± 0.10 | 8.533 ± 0.083 | 5 |
| 10.92 ± 0.10 | 8.104 ± 0.075 | 14 |
| 11.24 ± 0.10 | 7.875 ± 0.070 | 14 |
| 12.12 ± 0.10 | 7.302 ± 0.061 | 5 |
| 12.59 ± 0.10 | 7.031 ± 0.056 | 15 |
| 12.84 ± 0.10 | 6.895 ± 0.054 | 10 |
| 13.01 ± 0.10 | 6.807 ± 0.053 | 6 |
| 13.66 ± 0.10 | 6.483 ± 0.048 | 15 |
| 13.91 ± 0.10 | 6.367 ± 0.046 | 23 |
| 14.29 ± 0.10 | 6.197 ± 0.043 | 16 |
| 14.54 ± 0.10 | 6.090 ± 0.042 | 33 |
| 14.95 ± 0.10 | 5.928 ± 0.040 | 23 |
| 15.28 ± 0.10 | 5.799 ± 0.038 | 7 |
| 15.55 ± 0.10 | 5.700 ± 0.037 | 10 |
| 16.05 ± 0.10 | 5.523 ± 0.034 | 21 |
| 16.38 ± 0.10 | 5.411 ± 0.033 | 11 |
| 16.67 ± 0.10 | 5.319 ± 0.032 | 10 |
| 16.87 ± 0.10 | 5.256 ± 0.031 | 11 |
| 17.03 ± 0.10 | 5.205 ± 0.031 | 9 |
| 17.35 ± 0.10 | 5.111 ± 0.029 | 9 |
| 17.52 ± 0.10 | 5.062 ± 0.029 | 10 |
| 17.85 ± 0.10 | 4.968 ± 0.028 | 7 |
| 18.27 ± 0.10 | 4.856 ± 0.026 | 12 |
| 18.62 ± 0.10 | 4.765 ± 0.025 | 15 |
| 19.02 ± 0.10 | 4.665 ± 0.024 | 24 |
| 19.49 ± 0.10 | 4.554 ± 0.023 | 22 |
| 20.23 ± 0.10 | 4.390 ± 0.022 | 7 |
| 20.56 ± 0.10 | 4.320 ± 0.021 | 11 |
| 21.26 ± 0.10 | 4.179 ± 0.020 | 12 |
| 21.80 ± 0.10 | 4.077 ± 0.019 | 13 |
| 22.23 ± 0.10 | 3.999 ± 0.018 | 15 |
| 22.63 ± 0.10 | 3.929 ± 0.017 | 12 |
| 22.92 ± 0.10 | 3.881 ± 0.017 | 9 |
| 23.32 ± 0.10 | 3.815 ± 0.016 | 9 |
| 23.79 ± 0.10 | 3.741 ± 0.016 | 9 |
| 24.24 ± 0.10 | 3.672 ± 0.015 | 10 |
| 24.54 ± 0.10 | 3.628 ± 0.015 | 10 |
| 25.34 ± 0.10 | 3.515 ± 0.014 | 14 |
| 25.89 ± 0.10 | 3.441 ± 0.013 | 8 |
| 26.41 ± 0.10 | 3.375 ± 0.013 | 12 |
| 26.61 ± 0.10 | 3.350 ± 0.012 | 11 |
| 27.09 ± 0.10 | 3.291 ± 0.012 | 11 |
| 27.63 ± 0.10 | 3.229 ± 0.012 | 13 |
| 28.30 ± 0.10 | 3.154 ± 0.011 | 9 |

TABLE 15-continued

Observed Peaks for Rifaximin Form μ

| °2θ | d space (Å) | Intensity (%) |
|---|---|---|
| 28.97 ± 0.10 | 3.083 ± 0.010 | 10 |
| 29.25 ± 0.10 | 3.053 ± 0.010 | 11 |

TABLE 16

Prominent Peaks for Rifaximin Form μ

| °2θ | d space (Å) | Intensity (%) |
|---|---|---|
| 4.75 ± 0.10 | 18.597 ± 0.400 | 99 |
| 4.82 ± 0.10 | 18.339 ± 0.388 | 100 |
| 7.86 ± 0.10 | 11.248 ± 0.145 | 23 |
| 8.13 ± 0.10 | 10.879 ± 0.135 | 77 |
| 8.39 ± 0.10 | 10.533 ± 0.127 | 60 |
| 8.56 ± 0.10 | 10.328 ± 0.122 | 53 |
| 8.73 ± 0.10 | 10.130 ± 0.117 | 57 |
| 9.65 ± 0.10 | 9.167 ± 0.096 | 17 |

TABLE 17

Tentative Indexing Solutions and Derived Quantities

| Form/Pattern | Rifaximin, Form μ | |
|---|---|---|
| Family and | Monoclinic | |
| Space Group | $P2_1$ (#4) | |
| Z'/Z | 4/8 | |
| a (Å) | 13.043 | 13.063 |
| b (Å) | 21.040 | 21.144 |
| c (Å) | 37.502 | 37.697 |
| α (deg) | 90 | 90 |
| β (deg) | 96.36 | 96.42 |
| γ (deg) | 90 | 90 |
| Volume (Å³/cell) | 10228.1 | 10346.8 |
| V/Z (Å³/formula unit) | 1278.5 | 1293.4 |

TABLE 18

Observed Peak Ranges for Rifaximin Form Mu

| °2θ Range | d Space Range (Å) | Intensity Range (%) |
|---|---|---|
| (4.72-4.75) ± 0.10 | 18.597 ± 0.400-18.729 ± 0.405 | 99-100 |
| (4.79-4.82) ± 0.10 | 18.339 ± 0.388-18.467 ± 0.394 | 84-100 |
| (6.29-6.32) ± 0.10 | 13.980 ± 0.224-14.054 ± 0.227 | 7-8 |
| (6.94-6.96) ± 0.10 | 12.705 ± 0.185-12.736 ± 0.186 | 10-14 |
| (7.44-7.46) ± 0.10 | 11.852 ± 0.161-11.879 ± 0.162 | 5-7 |
| (7.84-7.86) ± 0.10 | 11.248 ± 0.145-11.272 ± 0.145 | 20-23 |
| (8.11-8.13) ± 0.10 | 10.879 ± 0.135-10.901 ± 0.136 | 55-77 |
| (8.36-8.39) ± 0.10 | 10.533 ± 0.127-10.575 ± 0.128 | 32-60 |
| (8.55-8.56) ± 0.10 | 10.328 ± 0.122-10.348 ± 0.122 | 44-53 |
| (8.70-8.73) ± 0.10 | 10.130 ± 0.117-10.169 ± 0.118 | 44-57 |
| (8.88-8.90) ± 0.10 | 9.941 ± 0.113-9.959 ± 0.113 | 5-8 |
| (9.60-9.65) ± 0.10 | 9.167 ± 0.096-9.215 ± 0.097 | 13-17 |
| (10.15-10.18) ± 0.10 | 8.687 ± 0.086-8.716 ± 0.087 | 6-7 |
| (10.32-10.37) ± 0.10 | 8.533 ± 0.083-8.575 ± 0.084 | 3-5 |
| (10.88-10.92) ± 0.10 | 8.104 ± 0.075-8.128 ± 0.075 | 10-14 |
| (11.20-11.24) ± 0.10 | 7.875 ± 0.070-7.899 ± 0.071 | 11-14 |
| (12.09-12.12) ± 0.10 | 7.302 ± 0.061-7.322 ± 0.061 | 3-5 |
| (12.54-12.59) ± 0.10 | 7.031 ± 0.056-7.059 ± 0.057 | 15-18 |
| (12.79-12.84) ± 0.10 | 6.895 ± 0.054-6.922 ± 0.054 | 6-10 |
| (12.96-13.01) ± 0.10 | 6.807 ± 0.053-6.833 ± 0.053 | 6-6 |
| (13.63-13.66) ± 0.10 | 6.483 ± 0.048-6.499 ± 0.048 | 9-15 |
| (13.86-13.91) ± 0.10 | 6.367 ± 0.046-6.390 ± 0.046 | 19-23 |
| (14.90-14.95) ± 0.10 | 5.928 ± 0.040-5.948 ± 0.040 | 16-23 |
| (15.25-15.28) ± 0.10 | 5.799 ± 0.038-5.811 ± 0.038 | 6-7 |
| (15.50-15.55) ± 0.10 | 5.700 ± 0.037-5.718 ± 0.037 | 8-10 |

TABLE 18-continued

Observed Peak Ranges for Rifaximin Form Mu

| °2θ Range | d Space Range (Å) | Intensity Range (%) |
|---|---|---|
| (16.00-16.05) ± 0.10 | 5.523 ± 0.034-5.540 ± 0.035 | 14-21 |
| (16.30-16.38) ± 0.10 | 5.411 ± 0.033-5.438 ± 0.033 | 10-11 |
| (16.62-16.67) ± 0.10 | 5.319 ± 0.032-5.335 ± 0.032 | 8-10 |
| (16.78-16.87) ± 0.10 | 5.256 ± 0.031-5.282 ± 0.031 | 6-11 |
| (16.97-17.03) ± 0.10 | 5.205 ± 0.031-5.226 ± 0.031 | 6-9 |
| (17.27-17.35) ± 0.10 | 5.111 ± 0.029-5.135 ± 0.030 | 8-9 |
| (17.47-17.52) ± 0.10 | 5.062 ± 0.029-5.077 ± 0.029 | 6-10 |
| (17.84-17.85) ± 0.10 | 4.968 ± 0.028-4.973 ± 0.028 | 5-7 |
| (18.20-18.27) ± 0.10 | 4.856 ± 0.026-4.873 ± 0.027 | 9-12 |
| (18.57-18.62) ± 0.10 | 4.765 ± 0.025-4.778 ± 0.026 | 13-15 |
| (18.97-19.02) ± 0.10 | 4.665 ± 0.024-4.678 ± 0.025 | 24-24 |
| (19.42-19.49) ± 0.10 | 4.554 ± 0.023-4.570 ± 0.023 | 22-22 |
| (21.76-21.80) ± 0.10 | 4.077 ± 0.019-4.084 ± 0.019 | 10-13 |
| (22.18-22.23) ± 0.10 | 3.999 ± 0.018-4.008 ± 0.018 | 10-15 |
| (22.52-22.63) ± 0.10 | 3.929 ± 0.017-3.949 ± 0.017 | 12-12 |
| (22.83-22.92) ± 0.10 | 3.881 ± 0.017-3.895 ± 0.017 | 7-9 |
| (23.27-23.32) ± 0.10 | 3.815 ± 0.016-3.823 ± 0.016 | 8-9 |
| (23.70-23.79) ± 0.10 | 3.741 ± 0.016-3.754 ± 0.016 | 7-9 |
| (24.17-24.24) ± 0.10 | 3.672 ± 0.015-3.682 ± 0.015 | 9-10 |
| (24.47-24.54) ± 0.10 | 3.628 ± 0.015-3.638 ± 0.015 | 8-10 |
| (25.26-25.34) ± 0.10 | 3.515 ± 0.014-3.526 ± 0.014 | 12-14 |
| (25.81-25.89) ± 0.10 | 3.441 ± 0.013-3.452 ± 0.013 | 7-8 |
| (26.53-26.61) ± 0.10 | 3.350 ± 0.012-3.360 ± 0.012 | 11-11 |
| (26.98-27.09) ± 0.10 | 3.291 ± 0.012-3.305 ± 0.012 | 11-11 |
| (27.55-27.63) ± 0.10 | 3.229 ± 0.012-3.238 ± 0.012 | 11-13 |
| (28.23-28.30) ± 0.10 | 3.154 ± 0.011-3.161 ± 0.011 | 7-9 |
| (28.87-28.97) ± 0.10 | 3.083 ± 0.010-3.093 ± 0.011 | 7-10 |
| (29.15-29.25) ± 0.10 | 3.053 ± 0.010-3.064 ± 0.010 | 10-11 |

TABLE 19

Prominent Peak Ranges for Rifaximin Form Mu

| °2θ Range | d Space Range (Å) | Intensity Range (%) |
|---|---|---|
| (4.72-4.75) ± 0.10 | 18.597 ± 0.400-18.729 ± 0.405 | 99-100 |
| (4.79-4.82) ± 0.10 | 18.339 ± 0.388-18.467 ± 0.394 | 84-100 |
| (7.84-7.86) ± 0.10 | 11.248 ± 0.145-11.272 ± 0.145 | 20-23 |
| (8.11-8.13) ± 0.10 | 10.879 ± 0.135-10.901 ± 0.136 | 55-77 |
| (8.36-8.39) ± 0.10 | 10.533 ± 0.127-10.575 ± 0.128 | 32-60 |
| (8.55-8.56) ± 0.10 | 10.328 ± 0.122-10.348 ± 0.122 | 44-53 |
| (8.70-8.73) ± 0.10 | 10.130 ± 0.117-10.169 ± 0.118 | 44-57 |
| (9.60-9.65) ± 0.10 | 9.167 ± 0.096-9.215 ± 0.097 | 13-17 |
| (12.54-12.59) ± 0.10 | 7.031 ± 0.056-7.059 ± 0.057 | 15-18 |

TABLE 20

Characterizations of Rifaximin Form Mu

| Analytical Technique | Results[3] |
|---|---|
| $^1$H-NMR | Chemical structure intact |
| | 0.5 mole of ethanol per mole of API |
| | Chemical structure intact |
| | 0.6 mole of ethanol per mole of API |
| Karl-Fischer | 14.1 wt % of water (approximately 7 moles) |
| | 12.7 wt % of water (approximately 6 moles) |
| DSC | Endo 92° C. (max), ΔH = 443.1 J/g |
| TG | 15.7% wt loss up to 100° C. |
| ATR-IR | Spectrum acquired |
| Raman | Spectrum acquired |
| Solid-State $^{13}$C NMR | Spectrum acquired |

TABLE 20-continued

Characterizations of Rifaximin Form Mu

| Analytical Technique | Results[3] |
|---|---|
| Moisture Balance | −11.0% wt change upon equilibration at 5% RH |
| | 9.5% wt gain from 5%-95% RH |
| | 9.3% wt lost from 95%-5% RH |
| Post-MB XRPD | Form γ |

[3]Endo = endotherm; wt = weight.

TABLE 21

Stress Study of Rifaximin Form μ

| Condition | Observations[4] | XRPD Result |
|---|---|---|
| 60° C./Vacuum, ~24 hours | Dark red blades, B/E | γ |
| 59-62° C./Vacuum, ~24 hours | Dark red solid | γ |
| 97% RH (RT), 16 days | Orange | μ + β |

[4]B = birefringent; E = extinction.

Example 5

Preparation of Form Gamma

Form Gamma is a hygroscopic crystalline mesophase. This form demonstrates 1.2-3.8% weight loss by TGA and an endotherm at approximately 203° C. (Table 4).

Rifaximin Form Gamma was obtained from solution in ethanol/water mixtures. Solids were obtained by crash cooling an ethanol/water (1/0.45) solution in an ice bath and air drying for 45 minutes and from a Form a slurry in ethanol/water (1/0.5). TG analysis demonstrated a 1.2 to 3.8% weight loss corresponding to a broad endotherm at 89° C. in the DSC curve. A minor endotherm, observed in both samples, at 203° C. Moisture balance sorption/desorption showed a 2.4% weight loss upon equilibration at 5% RH. The material is hygroscopic, gaining 10.8% weight under 95% RH. This weight (11.7%) was lost upon desorption to 5% RH. Long-term relative humidity studies of Form γ showed no form conversion when exposed to relative humidities from 11 to 94% for two days. The form remained unchanged by XRPD analysis after drying under vacuum at ambient temperature for one day. Other methods are disclosed infra, for example, in the Tables which follow.

Form Zeta

Form Zeta is a crystalline mesophase. The material was generated by slurrying Form Alpha dry in ethanol/water (1/0.45 at 0° C. and 1/1 at ambient temperature) for two days. Recovered solids were allowed to air dry and stored under ambient conditions for three days. Form Zeta was also formed by storing Form ζ under 58 and 75% RH for three days. Other methods are disclosed infra, for example, in the Tables which follow.

Example 6

Preparation of Form Zeta

Form ζ was observed by XRPD analysis of solids in solution (FIG. 42). These solids were removed and stressed under various RH conditions. XRPD analysis after three days showed conversion to Form γ under 43% RH; Form γ-1 under 58 and 75% RH, and Form β+γ-1 under 94% RH, though form conversion was likely initiated upon removal of the solids from solution. Other methods are disclosed infra, for example, in the Tables which follow.

Example 7

Preparation of Form Eta

Form η was generated according to FIG. 53. Other methods are disclosed infra, for example, in the Tables which follow. For example, as shown by FIG. 53, the Eta crystallization process consists of dissolution of rifaximin in ethanol followed by cooling to a seeding temperature, adding a separately prepared slurry of Form Zeta seeds in ethanol at a seeding temperature, holding for one hour followed by cooling to a sub-ambient temperature to generate a slurry of Form Zeta. The slurry is then filtered, washed and dried.

Example 8

Preparation of Form Iota

Form ι was generated according to FIG. 53. Other methods are disclosed infra, for example, in the Tables which follow. The space group was determined to be $P2_12_12_1$. The packing motif of rifaximin Form Iota is different than the layered arrangement observed in the previous two structures. The crystal structure contained additional residual electron density, typically attributed to highly disordered solvent, in the lattice.

TABLE 22

Form η and Mixtures of Form η

| Initial Form | Conditions | Final Form |
|---|---|---|
| η | vac oven, 40° C., 1 day | η |
| ζ | vac oven, ambient, 1 day | η |
| ζ | vac dry | γ + η |
| ζ | vac oven, 45° C., 2 days | η |

TABLE 23

Crystallization from EtOH and EtOH/Water Mixtures

| Solvents | Conditions[a] | Observations[b] | XRPD Form |
|---|---|---|---|
| EtOH | slurry, ambient, 3 days | orange; fragments; B&E | ζ |
|  | a) SE, 5 days; b) seeded with ε | orange; needle; B&E | ζ |
| EtOH/H$_2$O 1/0.02 mL | slurry, ambient, 3 days | orange; irregular; fragments; B&E | ζ |
| EtOH/H$_2$O 1/0.1 mL | slurry, ambient, 3 days | orange; fragments; B&E | ζ |
| EtOH/H$_2$O 1/0.25 mL | a) SC; refrigerator b) seeded with ε | orange; needle; B&E | ζ |
| EtOH/H$_2$O 2/0.5 mL | slurry, ambient, 5 hours | — | ζ |
| EtOH/H$_2$O 1/0.45 mL | control cooling: 3° C./h, 70-20° C. | in solution | ζ |
|  | crash cool in ice-water | in solution | ζ |
| EtOH/H$_2$O 1/0.5 mL | slurry, 0° C., 2 days; air-dried and stored at ambient 3 days | light orange; small needle; B&E | (ζ) |
|  | slurry, ambient, 2 days; air-dried and stored at ambient 3 days | orange; small needles; B&E | (ζ) |
| H$_2$O | slurry (β-1), ambient, 1 days; air dried 7 h | light orange; fragments; B&E | α + β |

[a] SE = slow evaporation; SC = slow cooling.
[b] B&E = birefringence and extinction.
[c] Samples were determined in solution in a capillary.

TABLE 24

Rifaximin Drying Experiments

| Starting Material | Conditions | Observations a | XRPD Form |
|---|---|---|---|
| ζ | stored in refrigerator 3 weeks | — | ζ |
| ζ | open vial in hood | orange; small fragments; B&E | γ |
| ζ | vac oven, ambient, 1 day | orange; irregular; B&E | η |
| ζ | vac oven, 45° C., 2 days | orange; fragments; B&E | η |
| ζ | air dry 2329-06-02a | dark orange; irregular; B&E | γ |
|  | vac dry 2329-06-02a | dark orange; irregular: B&E | γ + η |
| η | vac oven, 40° C., 1 day | orange; fragment; B&E | η | a. B&E = birefringence and extinction.

TABLE 25

Stressing Under Various Relative Humidities

| Initial Form | Conditions[a] | Observations | XRPD Form |
|---|---|---|---|
| α | P$_2$O$_5$, 4 days | dark orange; irregular particles; B&E | α dry |
| α dry | 58% RH, 2 days | light orange; small irregular particle; B&E | β |
|  | 75% RH, 2 days | light orange; small irregular particle; B&E | β |
|  | 94% RH, 2 days | light orange; small irregular particle; B&E | β |
| ζ | 43% RH, 3 days | Orange; small particle; B&E | γ |
|  | 58% RH, 3 days | Orange; small particle; B&E | ζ |
|  | 75% RH, 3 days | Orange; small particle; B&E | ζ |
|  | 94% RH, 3 days | light orange; small particle; B&E | β + ζ |
| ζ | stability chamber 75% RH@40° C., 1 day | orange; needle; B&E | ζ + γ |

[a]All samples stored at room temperature unless otherwise indicated; RH = relative humidity
b. B = birefringence; E = extinction The following techniques are described below, but are used throughout the examples.

Slow Evaporation (SE)

Solvent was added to weighed amounts of rifaximin in vials. Mixtures were sonicated to achieve complete dissolution of solids. The solutions were then filtered into clean vials. Solvents were slowly evaporated at ambient conditions.

Crash Cool (CC)

A sample of rifaximin in ethanol/water 1/0.45 was prepared and passed through 0.2-μm nylon filter into a clean vial. The vial containing the solution was then rapidly cooled by submersion in an ice bath for several seconds. Solids that precipitate were collected by filtration and dried.

Slurry Experiments

Test solvents were added to rifaximin in vials such that excess undissolved solids were present in solutions. The mixtures were than slurried on a shaker block or rotating wheel at subambient or room temperature.

Stressing Under Various Relative Humidities (RH)

A vial containing rifaximin was placed uncovered within a jar containing phosphorous pentoxide (P2O5) or a saturated salt solution in water. The jar was sealed and stored at either ambient temperature or in an oven at elevated temperature.

Slow Cool (SC)

Saturated solutions of rifaximin were prepared by slurrying excess solids in the test solvent at elevated temperature. The saturated solution was filtered while warm into a clean vial. The sample was allowed to cool to room temperature, and then further cooled to sub-ambient temperature using a refrigerator, followed by a freezer.

Milling

A solid sample of rifaximin was charged to a milling container with a milling ball. Samples were milled for 5 or 15 minute intervals (2×5 minutes, 2×15 minutes, and 3×15 minutes) at 30 Hz using a Retsch MM200 mixer mill. Solids were scraped from the sides of the vial after each interval.

Optical Microscopy

Optical microscopy was performed using a Leica MZ12.5 stereomicroscope. Various objectives typically ranging from 0.8-4× were used with crossed-polarized light to view samples. Samples were viewed in situ.

Thermal Analyses

Differential Scanning Calorimetry (DSC)

Differential scanning calorimetry (DSC) was performed using a TA Instruments differential scanning calorimeter 2920. The sample was placed into an aluminum DSC pan, and the weight accurately recorded. The pan was covered with a lid and then crimped or left uncrimped. The sample cell was equilibrated at 25° C. and heated under a nitrogen purge at a rate of 10° C./min, up to a final temperature of 250 or 350° C. Indium metal was used as the calibration standard. Reported temperatures are at the transition maxima.

Method A: initial equilibration at 25° C., heated to 250° C. at 10° C./min

Method B: initial equilibration at 25° C., heated to 350° C. at 10° C./min

Cyclic Differential Scanning calorimetry

Cyclic DSC was performed using a TA Instruments 2920 differential scanning calorimeter. The sample was placed into a hermetically sealed DSC pan, and the weight accurately recorded. The pan was covered with a lid containing a laser pinhole. The method was as follows:

1. Equilibrate at −50° C.
2. Ramp 20° C./min to 80° C.
3. Isothermal at 80° C. for 1 min
4. Equilibrate at −50° C.
5. Ramp 20° C./min to 220° C.

Indium metal was used as the calibration standard. Reported temperature is at the transition maxima.

Dynamic Vapor Sorption (DVS)

Automated vapor sorption (VS) data were collected on a VTI SGA-100 Vapor Sorption Analyzer. NaCl and PVP were used as calibration standards. Samples were not dried prior to analysis. Sorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Hot-Stage Microscopy

Hot stage microscopy was performed using a Linkam hot stage (FTIR 600) with a TMS93 controller mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20×0.4 N.A. long working distance objective with crossed polarizers and a first order red compensator. Images were captured using SPOT software (v. 4.5.9).

Modulated Differential Scanning Calorimetry (MDSC)

Modulated differential scanning calorimetry (MDSC) data were obtained on a TA Instruments differential scanning calorimeter 2920 equipped with a refrigerated cooling system (RCS). The sample was placed into an aluminum DSC pan, and the weight accurately recorded. The pan was covered with a lid perforated with a laser pinhole to allow for pressure release, and then hermetically sealed. MDSC data were obtained using a modulation amplitude of +/−0.8° C. and a 60 second period with an underlying heating rate of 1° C./min from 25-225° C. The temperature and the heat capacity were calibrated using indium metal and sapphire as the calibration standards, respectively. The reported glass transition temperatures are obtained from the half-height/inflection of the step change in the reversible heat flow versus temperature curve.

Thermogravimetric (TG) Analyses

Thermogravimetric (TG) analyses were performed using a TA Instruments 2950 thermogravimetric analyzer. Each sample was placed in an aluminum sample pan and inserted into the TG furnace. The furnace was first equilibrated at 25° C. or started directly from ambient temperature, then heated under nitrogen at a rate of 10° C./min, up to a final temperature of 350° C. Nickel and Alumel™ were used as the calibration standards. Methods for specific samples are referred to as summarized below Method A: no initial equilibration; analysis started directly from ambient, sample heated to 350° C. at 10° C./min Method B: initial equilibration at 25° C., sample heated to 350° C. at 10° C./min Method C: no initial equilibration; analysis started directly from ambient, sample heated to 300° C. at 10° C./min Spectroscopy Fourier Transform Infrared (FT-IR)

The IR spectra were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. An attenuated total reflectance (ATR) accessory (the Thunderdome™, Thermo Spectra-Tech), with a germanium (Ge) crystal was used for data acquisition. The spectra represent 256 co-added scans collected at a spectral resolution of 4 cm$^{-1}$. A background data set was acquired with a clean Ge crystal. A Log 1/R(R=reflectance) spectrum was acquired by taking a ratio of these two data sets against each other. Wavelength calibration was performed using polystyrene.

Fourier Transform Raman (FT-Raman)

FT-Raman spectra were acquired on a Raman accessory module interfaced to a Magna 860® Fourier transform infrared (FT-IR) spectrophotometer (Thermo Nicolet). This module uses an excitation wavelength of 1064 nm and an indium gallium arsenide (InGaAs) detector. Approximately 0.6-2.0 W of Nd:YVO$_4$ laser power was used to irradiate the sample. The samples were prepared for analysis by placing the material in a glass tube and positioning the tube in a gold-coated tube holder in the accessory A total of 256 or 1024 sample scans were collected from 98-3600 cm$^{-1}$ at a spectral resolution of 4 cm$^{-1}$, using Happ-Genzel apodization. Wavelength calibration was performed using sulfur and cyclohexane.

Peak Picking of IR and Raman Spectra

Peak picking was performed using Omnic version 7.2. Peak position variabilities are given to within ±2 cm$^{-1}$, based on the observed sharpness of the peaks picked and acquisition of data using a 2 cm$^{-1}$ data point spacing (4 cm$^{-1}$ resolution). Third party measurements on independently prepared samples on different instruments may lead to variability which is greater than ±2 cm$^{-1}$.

Automated Moisture Sorption/Desorption

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Karl-Fischer Titration (KF)

Coulometric Karl Fischer (KF) analysis for water determination was performed using a Mettler Toledo DL39 KF titrator. A blank titration was carried out prior to analysis. The sample was prepared under a dry nitrogen atmosphere, where approximately 1 gram of the sample were dissolved in approximately 1 mL dry Hydranal-Coulomat AD in a pre-dried vial. The entire solution was added to the KF coulometer through a septum and mixed for 10 seconds. The sample was then titrated by means of a generator electrode, which produces iodine by electrochemical oxidation: $2I^- \rightarrow I_2 + 2e^-$.

Solution 1D $^1$H NMR Spectroscopy (SSCI)

The solution NMR spectra were acquired with a Varian $^{UNITY}$INOVA-400 spectrometer. The samples were prepared by dissolving approximately 5 to 10 mg of sample in CDCl$_3$ containing TMS.

Solution 1D $^1$H NMR Spectroscopy (SDS, Inc.)

One solution $^1$H NMR spectrum was acquired by Spectral Data Services of Champaign, Ill. at 25° C. with a Varian $^{UNITY}$INOVA-400 spectrometer at a $^1$H Larmor frequency of 399.796 MHz. The samples were dissolved in CDCl$_3$. The spectra were acquired with a $^1$H pulse width of 6.0 µs, a 5 second delay between scans, a spectral width of 10 KHz with 35K data points, and 40 co-added scans. The free induction decay (FID) was processed with 64K points and an exponential line broadening factor of 0.2 Hz to improve the signal-to-noise ratio.

Solid State $^{13}$C Nuclear Magnetic Resonance (NMR)

Samples were prepared for solid-state NMR spectroscopy by packing them into 4 mm PENCIL type zirconia rotors.

The solid-state $^{13}$C cross polarization magic angle spinning (CP/MAS) NMR spectra were acquired at ambient temperature on a Varian $^{UNITY}$INOVA-400 spectrometer (Larmor frequencies: $^{13}$C=100.542 MHz, $^1$H=399.787 MHz). The sample was packed into a 4 mm PENCIL type zirconia rotor and rotated at 12 kHz at the magic angle. The chemical shifts of the spectral peaks were externally referenced to the carbonyl carbon resonance of glycine at 176.5 ppm.

Example 9

Alternative Preparation Methods for Select Rifaximin Forms

Rifaximin Form Zeta

Rifaximin (404.5 mg) was slurried in an ethanol/water mixture (2 mL/0.5 mL) at ambient temperature for approximately 5 hours. Solvent was removed by decantation and the damp solids stored in the refrigerator for less than one day prior to analysis by XRPD. Solids were damp prior to and after XRPD analysis. (FIG. 43)

Rifaximin Form Eta

After a portion of the rifaximin was removed for XRPD analysis the remainder of the sample was dried under vacuum at ambient temperature for approximately one day. Solids were stored in a dessicator prior to analysis by XRPD. (FIG. 45).

The method of forming Eta, shown in FIG. 54, consists of dissolution of Rifaximin (of any solid form) in ethanol followed by cooling to a seeding temperature, adding a separately prepared slurry of Form Zeta seeds in ethanol at the seeding temperature, holding for one hour followed by cooling to sub-ambient temperature to generate a slurry of Form Zeta. The slurry is then filtered, washed and dried. The crystallization process includes the filtration and washing steps. Certain embodiments of the Rifaximin Form Eta processes are to 1) control the solid form of the dried material to Form Eta, and 2) produce a high yield. The following parameters may influence the dried solid form and yield:

Water content in the Rifaximin starting material
Water content in ethanol
Rifaximin concentration
Final temperature
Hold time at final temperature Wash composition Exposure time of filter cake to atmosphere Drying temperature Drying pressure Drying time Seeding and cooling rate parameters do not appear to be involved in controlling the 'wet' form under the conditions investigated.

X-ray Powder Diffraction (XRPD)

Inel XRG-3000 Diffractometer

X-ray powder diffraction (XRPD) analyses were performed using an Inel XRG-3000 diffractometer equipped with a CPS (Curved Position Sensitive) detector with a 2θ range of 120°. Real time data were collected using Cu—Kα radiation. The tube voltage and amperage were set to 40 kV and 30 mA, respectively. The monochromator slit was set at 1-5 mm by 160 μm. The patterns are displayed from 2.5-40°2θ. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard.

PANalytical X'Pert Pro Diffractometer

Samples were also analyzed using a PANalytical X'Pert Pro diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop and a helium purge were used to minimize the background generated by air scattering. Soller slits were used for the incident and diffracted beams to minimize axial divergence. Diffraction patterns were collected using a scanning position-sensitive detector (X'Celerator) located 240 mm from the specimen. to the analysis a silicon specimen (NIST standard reference material 640c) was analyzed to verify the position of the silicon 111 peak.

TABLE 26

XRPD Peak Positions of Rifaximin Form Zeta

| Position (°2θ) | I/Io[a] |
|---|---|
| 4.7 (doublet) | 86 |
| 6.3 | 8 |
| 6.4 | 16 |
| 7.3 | 25 |
| 7.6 (doublet) | 100 |
| 8.2 | 10 |
| 8.6 | 20 |
| 9.5 | 12 |
| 10.2 (triplet) | 6 |
| 10.5 | 4 |
| 11.2 (doublet) | 3 |
| 11.9 (doublet) | 5 |
| 12.2 (weak) | 5 |
| 12.6 (quintet) | 16 |
| 12.9 (doublet) | 7 |
| 13.2 (doublet) | 5 |

[a]I/Io = relative intensity.

TABLE 27

XRPD Peak Positions of Rifaximin Form Eta

| Position (°2θ) | I/Io[a] |
|---|---|
| 5.3 | 28 |
| 6.1 | 71 |
| 7.3 | 24 |
| 7.5 | 28 |
| 7.9 | 100 |
| 8.8 | 76 |
| 12.7 | 34 |

[a]I/Io = relative intensity.

TABLE 28

Form Iota
Methods of Making the Form Iota of Rifaximin

| Solvent | Conditions | Observation | XRPD Result[b] |
|---|---|---|---|
| Methanol | CC | red orange, blades, single and in spherulites, birefringent | ι |
|  | SC | red orange, dendridic formations, birefringent | ι |

Example 10

Crystallization, Isolation & Drying Crystallization to Obtain Form Eta

The process for production of Form eta is set forth in flow chart 1 (FIG. 11).

A slurry of Rifaximin form zeta was prepared by stirring 33.4 g Rifaximin in 150 ml absolute ethanol for approximately 5 h. The seed slurry was prepared by stirring 500 mg of Rifaximin in 10 ml absolute ethanol at ambient for approximately 2 h. The Rifaximin slurry was charged to a 250 ml controlled laboratory reactor and dissolved by heating to 60° C. and holding while stirring at 300 rpm for 15 min. The solution was cooled to 40° C. over 30 min, then the seed slurry was added and held stirring at 40° C. for 60 min. The mixture was, cooled to 0 C at −0.2° C./min (200 min) and held for approximately 14 h. The slurry was then discharged into a Buchner funnel for filtration. Approximately 50 ml of chilled absolute ethanol (chilled over ice) was added to the reactor to rinse out the remaining particles and set aside. The slurry was filtered with vacuum to dry land then reactor rinse was added and filtered to dry land followed by the addition of 1 cake volume of chilled absolute ethanol. Vacuum filtration of the damp filter cake was continued for approximately 30 min. The filter cake was transferred to a crystallizing dish, covered with porous paper and dried in a vacuum oven at 40° C. for approximately 24 h. Yield=88%, LOD=27%, Form Eta (XRPD), 2.0% weight loss (TGA), 1.66% residual ethanol (H NMR). 0.82% water (KF).

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims.

Accordingly, it is to be understood that embodiments have been described by way of illustration and do not limit the scope of the claims.

What is claimed is:

1. A rifaximin polymorph Form Mu, or a salt, or hydrate form thereof, having an X-ray powder diffraction comprising peaks, in terms of 2θ, at
   two or more of about 4.72, about 4.79, and about 6.29; or
   two or more of about 4.72, about 4.79, and about 7.44; or
   two or more of about 4.72, about 4.79, and about 8.11; or
   two or more of about 4.72, about 8.11, and about 10.32; or
   two or more of about 4.72, about 6.94, and about 11.20; or
   two or more of about 4.72, about 4.79, and about 12.09; or
   two or more of about 4.72, about 4.79, about 6.29, about 6.94, about 7.44, about 7.84, about 8.11, about 8.36, about 8.55, about 8.70, about 8.88, and about 9.60; or
   two or more of about 4.72, about 4.79, about 6.29, about 6.94, about 7.44, about 7.84, about 8.11, about 8.36, about 8.55, about 8.70, about 8.88, about 9.60, about 10.15, about 10.32, about 10.88, about 11.02, and about 11.20.

2. A rifaximin polymorph Form Pi, or a salt, or hydrate form thereof, having an X-ray powder diffraction comprising peaks, in terms of 2, at about 6.91, about 7.16, and about 9.15.

3. A rifaximin polymorph Form Omicron, or a salt, or hydrate form thereof, having an X-ray powder diffraction comprising peaks, in terms of 2θ, at
   two or more of about 5.87, about 6.99, and about 7.77; or
   two or more of about 5.87, about 6.99, and about 8.47; or
   two or more of about 5.87, about 6.99, and about 9.13; or
   two or more of about 5.87, about 6.99, and about 9.58; or
   two or more of about 5.87, about 6.99, and about 9.74; or
   two or more of about 5.87, about 6.99, and about 12.35; or
   two or more of about 5.87, about 6.99, and about 13.27; or
   two or more of about 5.87, about 6.99, and about 13.69.

4. The Form Mu of rifaximin according to claim 1, wherein the rifaximin Form contains less than 5% by weight impurities.

5. The Form Mu of rifaximin according to claim 1, wherein one or more of the rifaximin forms is at least 50% pure, at least 75% pure, at least 80% pure, at least 90% pure, at least 95% pure, or at least 98% pure.

6. A pharmaceutical composition comprising the polymorph Form Mu of rifaximin according to claim 1, the polymorph Form Pi of rifaximin according to claim 2, or the polymorph Form Omicron according to claim 3, or a salt, or hydrate form thereof, and a pharmaceutically acceptable carrier.

7. A method of treating a bowel related disorder, comprising administering to a subject in need thereof and effective amount of the polymorph Form Mu of rifaximin according to claim 1, the polymorph Form Pi of rifaximin according to claim 2, or the polymorph Form Omicron according to claim 3, or a salt, or hydrate form thereof.

8. The Form Pi of rifaximin according to claim 2, wherein the rifaximin Form contains less than 5% by weight impurities.

9. The Form Pi of rifaximin according to claim 2, wherein one or more of the rifaximin forms is at least 50% pure, at least 75% pure, at least 80% pure, at least 90% pure, at least 95% pure, or at least 98% pure.

10. The Form Omicron of rifaximin according to claim 3, wherein the rifaximin Form contains less than 5% by weight impurities.

11. The Form Omicron of rifaximin according to claim 3, wherein one or more of the rifaximin forms is at least 50% pure, at least 75% pure, at least 80% pure, at least 90% pure, at least 95% pure, or at least 98% pure.

12. The pharmaceutical composition according to claim 6, wherein one or more of the rifaximin forms are formulated as coated or uncoated tablets, hard or soft gelatin capsules, sugar-coated pills, lozenges, wafer sheets, pellets or powders in a sealed packet.

* * * * *